(12) United States Patent
Fujii et al.

(10) Patent No.: US 6,737,409 B2
(45) Date of Patent: May 18, 2004

(54) DOLASTATIN 10 DERIVATIVES

(75) Inventors: Toshihiko Fujii, Yokohama (JP); Takehiro Okada, Fujisawa (JP); Mikio Taniguchi, Fujisawa (JP); Fumio Watanabe, Kamakura (JP)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/195,698

(22) Filed: Jul. 15, 2002

(65) Prior Publication Data

US 2003/0055002 A1 Mar. 20, 2003

(30) Foreign Application Priority Data

Jul. 19, 2001 (EP) .............................. 01117410

(51) Int. Cl.$^7$ ...................... A61K 38/07; C07D 207/08; C07K 5/103
(52) U.S. Cl. .................. 514/18; 530/330; 530/332; 548/571; 548/572
(58) Field of Search ...................... 514/18, 17; 530/330, 530/332, 337, 338; 548/517, 566, 571, 572

(56) References Cited

FOREIGN PATENT DOCUMENTS

WO    WO 01 18032    3/2001

OTHER PUBLICATIONS

Miyazaki K., et al., Chemical and Pharmaceutical Bulletin, Pharmaceutical Society of Japan, vol. 43, No. 10, pp. 1706–1718 (1995).
Pettit G.R., et al., Anti–Cancer Drug Design, Basingstoke, GB, vol. 13, No. 4, pp. 243–277 (1998).
Exp. Opin. Ther. Patents, 1999, vol. 9(8) pp. 1069–1081.
Curr. Pharm. Des. 1999, vol. 5, pp. 139–162.
Drugs of the Future, 1999, vol. 24(4), pp. 404–409.

*Primary Examiner*—Jeffrey E. Russel
(74) *Attorney, Agent, or Firm*—George W. Johnston; Patricia S. Rocha-Tramaloni

(57) ABSTRACT

Novel anti-tumor compounds of formula,

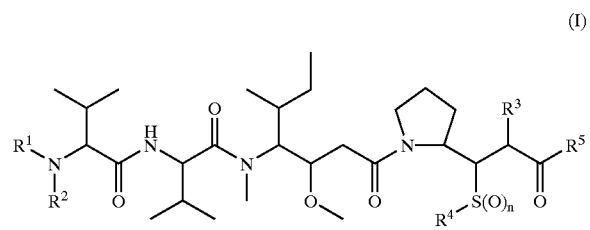

are disclosed. Also disclosed are pharmaceutical compositions comprising compounds of formula (I), the use of compounds of formula (I) for the treatment of cancer, and processes for the preparation of compounds (I).

52 Claims, No Drawings

DOLASTATIN 10 DERIVATIVES

FIELD OF THE INVENTION

The present invention relates to novel dolastatin 10 derivatives having anti-tumor activity and improved side effects, the use of these compounds in the treatment of tumors, pharmaceutical compositions containing those compounds as well as to processes and intermediates for the preparation of these compounds.

BACKGROUND OF THE INVENTION

Microtubules are known to be the main component of spindles in a mitotic apparatus of eucaryotic cells, and are also involved in many other basic and essential cell functions. Tubulin, a component of microtubules, has attracted our attention for many years as a good molecular target for anticancer therapy (*Exp. Opin. Ther. Patents* 1999, 9(8): 1069–1081). In fact, tubulin inhibitors such as taxanes and vinca alkaloids are currently used as important anticancer drugs for the treatment of various solid tumors. However, their efficacy is limited and their toxicity such as myelotoxicity is severe because they lack tumor selective activity. Dolastatin 10 is known to be a potent antimitotic peptide, isolated from the marine mollusk *Dolabella auricularia*, which inhibits tubulin polymerization and is a different chemical class from taxanes and vincas (*Curr. Pharm. Des.* 1999, 5: 139–162). Preclinical studies of dolastatin 10 have demonstrated activities against a variety of murine and human tumors in cell cultures and animal models. Dolastatin 10 and two synthetic dolastatin derivatives, Cemadotin and TZT-1027 (*Drugs of the future* 1999, 24(4): 404–409) are currently in Phase I and II clinical trials. While this new class of compounds has yielded certain new anti-tumor agents, these agents have safety drawbacks, such as myelotoxicity, neurotoxicity and some other adverse events.

SUMMARY OF THE INVENTION

Surprisingly it has been found that certain dolastatin 10 derivatives having various thio-groups at the dolaproine part show significantly improved anti-tumor activity and therapeutic index in human cancer xenograft models.

Accordingly, the present invention relates to novel compounds of formula I

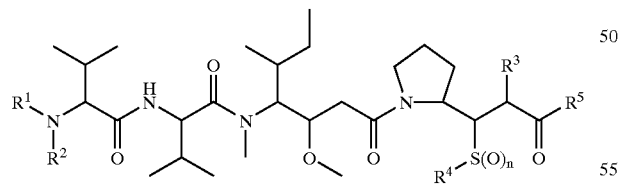

(I)

wherein
R$^1$, R$^2$ and R$^3$ are each independently selected from hydrogen or (C$_1$–C$_4$)-alkyl;
R$^4$ is selected from the group consisting of
hydrogen;
alkyl optionally substituted with one to three substituents selected from the group consisting of hydroxy, alkoxy, amino, mono- or di-alkylamino, carboxy, alkoxycarbonyl, carbamoyl, alkylcarbonyloxy, carbamoyloxy and halogen;
alkenyl;
alkinyl;
(C$_3$–C$_7$)-cycloalkyl;
aryl optionally substituted with one to three substituents selected from the group consisting of halogen, alkoxycarbonyl, carbamoyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino and benzyl;
aralkyl wherein the aryl group optionally substituted with one to three substituents selected from the group consisting of halogen, alkoxycarbonyl, carbamoyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino and benzyl; and
heterocyclylalkyl;
R$^5$ is selected from the group consisting of
(C$_1$–C$_6$)-alkylamino;
hydroxy;
(C$_3$–C$_7$)-cycloalkylamino optionally substituted by phenyl or benzyl;
arylamino;
aralkylamino having (C$_1$–C$_4$)-alkylene and wherein the aryl group optionally may be substituted with one to three substituents selected from the group consisting of halogen, alkoxycarbonyl, sulfamoyl, alkylcarbonyloxy, carbamoyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino and benzyl;
(C$_1$–C$_4$)-alkoxy;
benzhydrazino;
heterocyclyl optionally substituted with one to three substituents selected from the group consisting of benzyl, benzhydryl, alkyl, hydroxy, alkoxy, alkylcarbamoyloxy, amino, mono- or di-alkylamino, acylamino, alkoxy-carbonylamino, phenyl and halogen;
heterocyclylamino;
heterocycloalkylamino wherein the heterocyclyl group optionally may be substituted with one to three substituents selected from the group consisting of benzyl, benzhydryl, alkyl, hydroxy, alkoxy, alkylcarbamoyloxy, amino, dialkylamino, acylamino, alkoxycarbonylamino and halogen;
aralkyloxy and aralkyl, both optionally substituted with one to three substituents from the group consisting of halogen, alkoxycarbonyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino, aminosulfonyl and benzyl;
and
n is 0, 1 or 2;
or a pharmaceutical acceptable salt thereof.

These compounds have an anti-tumor activity and are useful for the treatment of malignant diseases, particularly of colorectal cancer, lung cancer, breast cancer, stomach cancer, cervical cancer and bladder cancer.

DETAILED DESCRIPTION OF THE INVENTION

Unless otherwise indicated the following definitions are set forth to illustrate and define the meaning and scope of the various terms used to described the invention herein.

The term "alkyl" as used herein, alone or in combination, means a straight-chain or branched-chain hydrocarbon group containing a maximum of 12, preferably a maximum of 6, carbon atoms, e.g., methyl, ethyl, n-propyl, 2-methylpropyl (iso-butyl), 1-methylethyl (iso-propyl), n-butyl, and 1,1-dimethylethyl (t-butyl), and more preferably a maximum of 4 carbon atoms. The alkyl group may be unsubstituted or may be substituted with one or more substituents, preferably with one to three substituents, most preferably with one substituent. The substituents are selected from the group consisting of hydroxy, alkoxy, amino, mono- or di-alkylamino, acetoxy, alkylcarbonyloxy, carbamoyloxy, alkoxycarbonyl, carbamoyl or halogen.

The term "alkenyl" as used therein, alone or in combination, refers to a hydrocarbon chain as defined for alkyl having at least one olefinic double bond (including for example, vinyl, allyl and butenyl) and having the general formula $C_mH_{2m-1}$ wherein m is an integer greater than 2, preferably m is an integer of 2 to 7.

The term "alkynyl" refers to a hydrocarbon chain as defined for alkyl having at least one triple bond (including for example propynyl, butyn-(1)-yl, etc) and having the general formula $C_mH_{2m-2}$ wherein m is an integer greater than 2, preferably m is an integer of 2 to 7.

The term "$(C_3-C_7)$-cycloalkyl" signifies a saturated, cyclic hydrocarbon group with 3–7 carbon atoms, i.e. cyclopropyl, cyclobutyl, cyclopentyl and cyclohexyl and the like. The cycloalkyl group may be unsubstituted or substituted with one or more substituents, preferably with one to three substituents, most preferably with one substituent. The substituents are selected from alkyl, phenyl, amino, hydroxy or halogen, preferably is phenyl.

The term "alkylene" refers to a biradical branched or unbranched hydrocarbon chain containing 1 to 4 carbon atoms, such as methylene (—$CH_2$—), ethylene, propylene, isopropylene and butylene.

The term "aryl" refers to an aromatic carbocyclic radical, i.e. a 6 or 10 membered aromatic or partially aromatic ring, e.g. phenyl (i.e. "Ph"), naphthyl or tetrahydro-naphthyl, preferably phenyl or naphthyl, and most preferably phenyl. The aryl moiety is optionally substituted with one or more subsituents, preferably with one to three, most preferably one, selected from the group consisting of halogen, preferably fluorine, chlorine, alkoxycarbonyl, (e.g. methoxycarbonyl), alkylcarbonyloxy (e.g., acetoxy), cyano, alkyl, alkoxy, phenyl, phenoxy, trifluormethyl, trifluormethoxy, alkylthio, hydroxy, carbamoyloxy, alkylcarbonylamino, heterocyclyl, sulfamoyl (i.e. $H_2NSO_2$—), amino, 1,3-dioxolyl, or 1,4-dioxolyl. Especially preferred substituents are alkyl, alkoxy, hydroxy, halogen, amino, alkylamino, dialkylamino, alkylthio, sulfamoyl, benzyl or heterocyclyl.

The term "aralkyl" refers to an aryl group as defined above attached to an alkylene group as defined above. The aryl group of the aralkyl may be substituted with one or more substituents, preferably one to three, more preferably with one to two and most preferably with one substituent selected from the group consisting of halogen, preferably fluorine, chlorine, alkoxycarbonyl, (e.g. methoxycarbonyl), alkylcarbonyloxy (e.g., acetoxy), cyano, alkyl, alkoxy, phenyl, phenoxy, trifluormethyl, trifluormethoxy, alkylthio, hydroxy, carbamoyloxy, alkylcarbonylamino, heterocyclyl, sulfamoyl, amino, 1,3-dioxolyl, or 1,4-dioxolyl. Especially preferred substituents aralkyl, alkoxy, hydroxy, halogen, amino, mono- or di-alkylamino or alkylthio.

The term "heterocyclyl" refers to a saturated, unsaturated or aromatic monovalent cyclic radical having at one to 3 hetero atoms selected from nitrogen, oxygen or sulfur or a combination thereof, examples of such heterocycles are; furyl, piperidine (preferably piperidin-1-yl, piperidin-4-yl), piperazine (preferably piperazine-1-yl), pyridine, thiophene, thiadiazole, thiazole, benzthiazol, imidazole, tetrahydroisoquinoline and the like. The heterocyclyl may be substituted with one or more substituents, preferably one to three, more preferably with one to two and most preferably with one substituent selected from the group consisting of benzyl, benzhydryl, alkyl, hydroxy, alkoxy, alkyl-carbamoyloxy, amino, dialkylamino, acylamino, alkoxycarbonylamino or halogen.

The term "heterocyclyl-amino" refers to a heterocyclic group as defined above attached via an amino radical, i.e., heterocyclyl-NH—.

The term "heterocyclyl-alkyl-amino" refers to a heterocyclic group as defined above attached via an alkylene group as defined above to the amino radical, i.e. heterocyclyl-alkylene-NH—. The heterocyclylamino may be substituted with one or more substituents, preferably one to three, more preferably with one to two and most preferably with one substituent selected from the group consisting of benzyl, benzhydryl, alkyl, hydroxy, alkoxy, alkylcarbamoyloxy, amino, mono- or di-alkylamino, acylamino, alkoxycarbonyl-amino or halogen. Especially preferred substituents are alkyl, hydroxy, alkylcarbamoyloxy, amino, dialkylamino, acylamino, alkylcarbonylamino or halogen.

The term "amino" refers to the group —$NH_2$ and includes amino groups which are further substituted by a lower alkyl group(s), or protected by a group known in the art such as a benzoxycarbonyl group, acetyl group, alkoxycarbonyl group or benzyl group and the like.

The term "cycloalkylamino" refers to cycloalkyl group as defined above attached to a structure via an amino radical, such as cyclopropyl, cyclobutyl, cyclopentyl and cyclohexyl and the like. The cycloalkylamino group may be unsubstituted or substituted with one or more substituents, preferably one to three, more preferably with one to two and most preferably with one substituent. The substituents are preferably phenyl or benzyl.

The term "arylamino" refers to an aryl group as defined above attached to a parent structure via an amino radical, i.e., aryl-NH—.

The term "aralkylamino" refers to an aryl group as defined above attached to a parent structure via an alkylene-amino radical, i.e., aralkyl-NH—. The aralkylamino group may be optionally substituted with a lower alkyl group, preferably a methyl group, i.e., aralkyl-$NCH_3$—.

The term "acetoxy" refers to the group —O—OC—$CH_3$.

The term "carbamoyl" refers to the group —CO—$NH_2$ and the term "carbamoyloxy" to the group —O—CO—NH.

The term "alkylcarbamoyloxy" refers to an alkyl group as defined above attached to a parent structure via a carbymoyloxy radical, i.e., —O—CO—NH-alkyl.

The term "alkylcarbonyloxy" refers to an alkyl group as defined above attached to a parent structure via a carbonyloxy radical, i.e., —O—CO-alkyl.

The term "alkoxy" refers to the group R'—O—, wherein R' is an alkyl group as defined above.

The term "aralkyloxy" refers to the group Y—O—, wherein Y is aralkyl group as defined above.

The term "alkylthio" refers to the group R—S—, wherein R is an alkyl group as defined above.

The term "halogen" refers to fluorine, bromine, iodine and chlorine.

In the present invention, the expression "optionally substituted with" means that substitution can occur at one or more positions, preferably at one to three positions, and, unless otherwise indicated, that the substituents are independently selected from the specified options.

"Pharmaceutically acceptable salt" refers to conventional acid-addition salts or base-addition salts which retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from potassium, sodium, ammonium, and quarternary ammonium hydroxide, such as for example tetramethylammonium hydroxide.

"Pharmaceutically acceptable," such as pharmaceutically acceptable carrier, excipient, prodrug, etc., means pharmacologically acceptable and substantially non-toxic to the subject to which the particular compound is administered.

"Pharmaceutically active metabolite" means a metabolic product of a compound of formula I which is pharmaceutically acceptable and effective.

In one embodiment, the present invention is directed to a compound of formula I

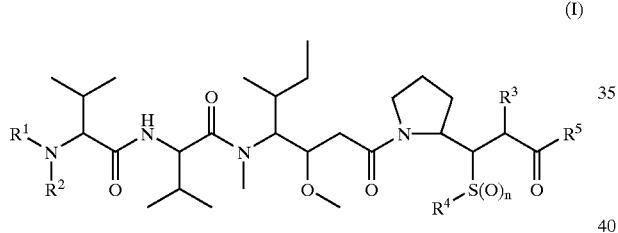

(I)

wherein $R^1$, $R^2$ and $R^3$ are each independently selected from hydrogen or $(C_1–C_4)$-alkyl;

$R^4$ is selected from the group consisting of
  hydrogen;
  alkyl optionally substituted with one to three substituents selected from the group consisting of hydroxy, alkoxy, amino, mono- or di-alkylamino, carboxy, alkoxycarbonyl, carbamoyl, alkylcarbonyloxy and halogen;
  alkenyl;
  alkinyl;
  $(C_3–C_7)$-cycloalkyl;
  aryl optionally substituted with one to three substituents selected from the group consisting of halogen, alkoxycarbonyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino and benzyl;
  aralkyl wherein the aryl group optionally substituted with one to three substituents selected from the group consisting of halogen, alkoxycarbonyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino and benzyl; and
  heterocyclylalkyl;

$R^5$ is selected from the group consisting of
  $(C_1–C_6)$-alkylamino;
  hydroxy;
  $(C_3–C_7)$-cycloalkylamino optionally substituted by phenyl or benzyl;
  arylamino;
  aralkylamino having $(C_1–C_4)$-alkylene and wherein the aryl group optionally may be substituted with one to three substituents selected from the group consisting of halogen, alkoxycarbonyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino and benzyl;
  $(C_1–C_4)$-alkoxy;
  benzhydrazino;
  heterocyclyl optionally substituted with one to three substituents selected from the group consisting of benzyl, benzhydryl, alkyl, hydroxy, alkoxy, alkylcarbamoyloxy, amino, mono- or di-alkylamino, acylamino, alkoxy-carbonylamino, phenyl and halogen;
  heterocyclylamino;
  heterocycloalkylamino wherein the heterocyclyl group optionally may be substituted with one to three substituents selected from the group consisting of benzyl, benzhydryl, alkyl, hydroxy, alkoxy, alkylcarbamoyloxy, amino, dialkylamino, acylamino, alkoxycarbonylamino and halogen;
  aralkyloxy and aralkyl, both optionally substituted with one to three substituents from the group consisting of halogen, alkoxycarbonyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino, aminosulfonyl and benzyl;

and n is 0, 1 or 2;

or a pharmaceutical acceptable salt thereof.

Preferably, the present invention relates to compounds of the above formula (I), wherein $R^4$ is hydrogen; alkyl optionally substituted with one to three substituents selected from the group consisting of hydroxy, amino, mono- or di-alkylamino, carbamoyl, acetoxy, carbamoyloxy or carboxy; alkenyl; alkinyl; $(C_3–C_7)$-cycloalkyl; aryl optionally substituted with one to three substituents selected from the group consisting of alkyl, alkoxy, hydroxy, halogen, amino, mono- or di-alkylamino, alkylthio or alkylcarbonylamino; aralkyl with the aryl group optionally substituted with one to three substituents selected from the group consisting of alkyl, alkoxy, hydroxy, halogen, amino, mono- or di-alkylamino, or alkylthio; or heterocyclylalkyl.

More preferably, the present invention relates to compounds of the above formula (I), wherein $R^4$ is phenyl, methyl, t-butyl, 4-tButylphenyl, 4-methoxyphenyl, 2-aminoethyl, 2-dimethylaminoethyl, ZHNCH$_2$CH$_2$— ("Z" is the group benzyloxycarbonyl), 4-methylthiophenyl, cyclohexyl, 2-, 3-, or 4-hydroxyphenyl, 4-acetoaminophenyl, 4-fluorophenyl, ethyl, i-propyl, benzyl, 2-acetoxyethyl, ethylcarbamoyloxyethyl, diethylcarbamoylmethyl, phenylethyl, allyl, n-pentyl, 2-naphtyl, 4-fluorobenzyl, 2-furylmethyl or 2-hydroxyethyl.

Most preferably, the present invention relates to compounds of the above formula (I), wherein $R^4$ is phenyl; 4-hydroxyphenyl (R); 4-acetoaminophenyl; tertia-butyl; (R); ethyl; isopropyl; t-butyl; benzyl; 3-hydroxyphenyl 2-hydroxyphenyl; 2-acetoxyethyl; allyl; n-pentyl, 2-hydroxyethyl or methyl.

In another preferred embodiment of a compound of formula (I), $R^5$ is $(C_1-C_6)$-alkylamino; hydroxy; $(C_3-C_7)$-cycloalkylamino optionally substituted by phenyl or benzyl; arylamino; aralkylamino having $(C_1-C_4)$-alkylene and the aryl group optionally substituted with one to three substituents selected from the group consisting of $H_2NSO_2$—, hydroxy, alkyl, benzyl, alkoxy, carbamoyloxy or heterocyclyl; $(C_1-C_4)$-alkoxy; benzhydrazino; heterocyclyl optionally substituted by benzyl or benzhydryl; heterocyclylamino; heterocycloalkyamino with the heterocyclyl group optionally substituted with one to three substituents selected from the group consisting of alkyl, hydroxy, alkoxy, alkylcarbamoyloxy, amino, dialkylamino, acylamino, alkoxycarbonylamino or halogen; or aralkyloxy and aralkyl both optionally substituted with one to three substituents from the group consisting of halogen, alkoxycarbonyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino, aminosulfonyl or benzyl.

More preferably, the present invention relates to compounds of the above formula (I), wherein $R^5$ is phenylethylamino; phenylethoxy; benzyloxy; 2-naphtylmethylamino; benzyl-piperazino; 1,2,3,4-tetrahydroisoquinolino; t-butoxy; hydroxy; 4-$H_2NSO_2PhCH_2CH_2$; 2-, 3- or 4-hydroxyphenylethylamino; 2-, 3- or 4-hydroxyphenylethyl-N-methylamino; N-benzylphenethylamino; 4-t-butylbenzylamino; benzylamino; N-methylphenethylamino; 4-benzhydrylpiperazino; 2-phenylcyclopropylamino; thienylethylamino; 2-pyridylethylamino; 5-ethylpyrazol; 4,3-dimethoxyphenylethylamino; benzylhydrazino; benzothiazol-2-ylmethyl-amino; 2-pyridin-4-yl-amino; 3,4-dimethoxy-phenyl-ethyl-methyl-amino;, bezothiazol-2-ylmethyl-amino; 2-pyridin-3-yl-ethylamino; pyridin-4-ylmethyl-amino; thiazol-2-ylamino; naphtalen-2-ylamino; 4-chloro-phenyl-ethylamino; 4-methoxy-phenyl-ethylamino; 4-(1,2,3)thiadiazol-4-yl-benzylamino; 2-cyclohexylamino or 1-benzyl-piperidin-4-ylamino.

Most preferably, the present invention relates to compounds of the above formula (I) wherein $R^5$ is phenylethylamino, 4,3-dimethoxyphenylethylamino, thienylethylamino, 2-pyridylethylamino, 4-hydroxyphenylethylamino, N-methylphenethylamino, 2-hydroxy-phenylethylamino, 3-hydroxyphenylethylamino, 2-hydroxyphenylethyl-N-methylamino, 3-hydroxyphenylethyl-N-methylamino, 4-hydroxyphenylethyl-N-methylamino or benzylhydrazino.

In another preferred embodiment $R^1$ and $R^2$ are each independently selected from $(C_1-C_4)$-alkyl. Most preferably, $R^1$ and $R^2$ are methyl.

Additionally preferred are compounds of formula (I) wherein $R^1$ and $R^2$ are methyl, $R^3$ is hydrogen and n is 0. Examples of such compounds are:

a) N-[1-({1-sec-Butyl-2-methoxy-4-oxo-4-[2-(2-phenethylcarbamoyl-1-phenylsulfanyl-ethyl)-pyrrolidin-1-yl]-butyl}-methyl-carbamoyl)-2-methyl-propyl]-2-dimethylamino-3-methyl-butyramide, b) N-[1-({1-sec-Butyl-2-methoxy-4-[2-(1-methylsulfanyl-2-phenethylcarbamoyl-ethyl)-pyrrolidin-1-yl]-4-oxo-butyl}-methyl-carbamoyl)-2-methyl-propyl]-2-dimethylamino-3-methyl-butyramide, c) N-[1-({1-sec-Butyl-4-[2-(1-(S)-tert-butylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide, d) N-{1-[(1-sec-Butyl-4-{2-[1-(4-tert-butyl-phenylsulfanyl)-2-phenethylcarbabamoyl-ethyl]-pyrrolidin-1-yl}-2-methoxy-4-oxo-butyl)-methyl-carbamoyl]-2-methyl-propyl}-2-dimethylamino-3-methyl-butyramide, e) N-{1-[(1-sec-Butyl-2-methoxy-4-{2-[1-(4-methoxy-phenylsulfanyl)-2-phenethylcarbamoyl-ethyl]-pyrrolidin-1-yl}-4-oxo-butyl)-methyl-carbamoyl]-2-methyl-propyl}-2-dimethylamino-3-methyl-butyramide, f) 3-[1-(4-{[2-(2-Dimethylamino-3-methyl-butyrylamino)-3-methyl-butyryl]-methyl-amino}-3-methoxy-5-methyl-heptanoyl)-pyrrolidin-2-yl]-3-methylsulfanyl-propionic acid phenethyl ester, g) 3-[1-(4-{[2-(2-Dimethylamino-3-methyl-butyrylamino)-3-methyl-butyryl]-methyl-amino}-3-methoxy-5-methyl-heptanoyl)-pyrrolidin-2-yl]-3-methylsulfanyl-propionic acid benzyl ester, h) N-(1-{[1-sec-Butyl-2-methoxy-4-(2-{1-methylsulfanyl-2-[(naphthalen-2-ylmethyl)-carbamoyl]-ethyl}-pyrrolidin-1-yl)-4-oxo-butyl]-methyl-carbamoyl}-2-methyl-propyl)-2-dimethylamino-3-methyl-butyramide, i) N-{1-[(4-{2-[1-(2-Amino-ethylsulfanyl)-2-phenethylcarbamoyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide, j) N-{1-[(4-{2-[3-(4-Benzyl-piperazin-1-yl)-1-methylsulfanyl-3-oxo-propyl]-pyrrolidin-1-yl}-1-sec-butyl-2-methoxy-4-oxo-butyl)-methyl-carbamoyl]-2-methyl-propyl}-2-dimethylamino-3-methyl-butyramide, k) N-{1-[(1-sec-Butyl-4-{2-[3-(3,4-dihydro-1H-isoquinolin-2-yl)-1-methylsulfanyl-3-oxo-propyl]-pyrrolidin-1-yl}-2-methoxy-4-oxo-butyl)-methyl-carbamoyl]-2-methyl-propyl}-2-dimethylamino-3-methyl-butyramide, l) N-{1-[(1-sec-Butyl-4-{2-[1-(2-dimethylamino-ethylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide, m) (2-{1-[1-(4-{[2-(2-Dimethylamino-3-methyl-butyrylamino)-3-methyl-butyryl]-methyl-amino}-3-methoxy-5-methyl-heptanoyl)-pyrrolidin-2-yl]-2-phenethylcarbamoyl-ethylsulfanyl}-ethyl)-carbamic acid benzyl ester, n) N-{1-[(1-sec-Butyl-2-methoxy-4-{2-[1-(4-methylsulfanyl-phenylsulfanyl)-2-phenethylcarbamoyl-ethyl]-pyrrolidin-1-yl}-4-oxo-butyl)-methyl-carbamoyl]-2-methyl-propyl}-2-dimethylamino-3-methyl-butyramide, o) N-[1-({1-sec-Butyl-4-[2-(1-cyclohexylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide, p) N-{1-[(1-sec-Butyl-4-{2-[1-(S)-(4-hydroxy-phenylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide, q) N-{1-[(1-sec-Butyl-4-{2-[1-(R)-(4-hydroxy-phenylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide, r) N-{1-[(4-{2-[1-(4-Acetylamino-phenylsulfanyl)-2-phenethylcarbamoyl-ethyl]-pyrrolidin-1-yl}-1-sec-butyl- 2-methoxy-4-oxo-butyl)-methyl -carbamoyl]-2-methyl-propyl}-2-dimethylamino-3-methyl-butyramide,
s) N-{1-[(1-sec-Butyl-4-{2-[1-(4-fluoro-phenylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide,
t) N-[1-({1-sec-Butyl-4-[2-(1-(R)-tert-butylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide,
u) N-[1-({1-sec-Butyl-4-[2-(1-ethylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide,
v) N-[1-({1-sec-Butyl-4-[2-(1-isopropylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide,
w) N-[1-({1-sec-Butyl-4-[2-(1-tert-butylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide,
x) N-[1-({4-[2-(1-Benzylsulfanyl-2-phenethylcarbamoyl-ethyl)-pyrrolidin-1-yl]-1-sec-butyl-2-methoxy-4-oxo-butyl}-methyl-carbamoyl)-2-methyl-propyl]-2-dimethylamino-3-methyl-butyramide,
y) N-{1-[(1-sec-Butyl-4-{2-[1-(2-hydroxy-phenylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide,
z) N-{1-[(1-sec-Butyl-4-{2-[1-(3-hydroxy-phenylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide,
aa) N-{1-[(1-sec-Butyl-4-{2-[1-(2-hydroxy-ethylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide,
bb) Acetic acid 2-{1-[1-(4-{[2-(2-dimethylamino-3-methyl-butyrylamino)-3-methyl-butyryl]-methyl-amino}-3-methoxy-5-methyl-heptanoyl)-pyrrolidin-2-yl]-2-phenethylcarbamoyl-ethylsulfanyl}-ethyl ester,
cc) 3-[1-(4-{[2-(2-Dimethylamino-3-methyl-butyrylamino)-3-methyl-butyryl]-methyl-amino}-3-methoxy-5-methyl-heptanoyl)-pyrrolidin-2-yl]-3-methylsulfanyl-propionic acid tert-butyl ester,
dd) 3-[1-(4-{[2-(2-Dimethylamino-3-methyl-butyrylamino)-3-methyl-butyryl]-methyl-amino}-3-methoxy-5-methyl-heptanoyl)-pyrrolidin-2-yl]-3-methylsulfanyl-propionic acid,
ee) N-(1-{[1-sec-Butyl-2-methoxy-4-(2-{1-methylsulfanyl-2-[2-(4-sulfamoyl-phenyl)-ethylcarbamoyl]-ethyl}-pyrrolidin-1-yl)-4-oxo-butyl]-methyl-carbamoyl}-2-methyl-propyl)-2-dimethylamino-3-methyl-butyramide,
ff) N-(1-{[1-sec-Butyl-4-(2-{2-[2-(4-hydroxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide,
gg) N-{1-[(1-sec-Butyl-2-methoxy-4-{2-[2-(methyl-phenethyl-carbamoyl)-1-methylsulfanyl-ethyl]-pyrrolidin-1-yl}-4-oxo-butyl)-methyl-carbamoyl]-2-methyl-propyl}-2-dimethylamino-3-methyl-butyramide,
hh) N-{1-[(4-{2-[3-(4-Benzhydryl-piperazin-1-yl)-1-methylsulfanyl-3-oxo-propyl]-pyrrolidin-1-yl}-1–2-methoxy-4-oxo-butyl)-methyl-carbamoyl]-2-methyl-propyl}-2-dimethylamino-3-methyl-butyramide,
ii) N-(1-{[1-sec-Butyl-4-(2-{2-[2-(2-hydroxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide,
jj) N-(1-{[1-sec-Butyl-4-(2-{2-[2-(3-hydroxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide,
kk) N-{1-[(4-{2-[2-(Benzyl-phenethyl-carbamoyl)-1-methylsulfanyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide,
ll) N-{1-[(1-sec-Butyl-2-methoxy-4-{2-[1-methylsulfanyl-2-(2-phenyl-cyclopropylcarbamoyl)-ethyl]-pyrrolidin-1-yl}-4-oxo-butyl)-methyl-carbamoyl]-2-methyl-propyl}-2-dimethylamino-3-methyl-butyramide,
mm) N-{1-[(1-sec-Butyl-4-{2-[2-(4-tert-butyl-benzylcarbamoyl)-1-methylsulfanyl-ethyl]-pyrrolidin-1-yl}-2-methoxy-4-oxo-butyl)-methyl-carbamoyl]-2-methyl-propyl}-2-dimethylamino-3-methyl-butyramide,
nn) N-[1-({4-[2-(2-Benzylcarbamoyl-1-methylsulfanyl-ethyl)-pyrrolidin-1-yl]-1-sec-butyl-2-methoxy-4-oxo-butyl}-methyl-carbamoyl)-2-methyl-propyl]-2-dimethylamino-3-methyl-butyramide,
oo) N-{1-[(4-{2-[2-(N'-Benzyl-hydrazinocarbonyl)-1-methylsulfanyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide,
pp) N-[1-({1-sec-Butyl-2-methoxy-4-oxo-4-[2-(2-phenethylcarbamoyl-1-phenethylsulfanyl-ethyl)-pyrrolidin-1-yl]-butyl}-methyl-carbamoyl)-2-methyl-propyl]-2-dimethylamino-3-methyl-butyramide,
qq) N-[1-({4-[2-(1-Allylsulfanyl-2-phenethylcarbamoyl-ethyl)-pyrrolidin-1-yl]-1-sec-butyl-2-methoxy-4-oxo-butyl}-methyl-carbamoyl)-2-methyl-propyl]-2-dimethylamino-3-methyl-butyramide,
rr) N-{1-[(1-sec-Butyl-2-methoxy-4-{2-[1-methylsulfanyl-2-(2-pyridin-4-yl-ethylcarbamoyl)-ethyl]-pyrrolidin-1-yl}-4-oxo-butyl)-methyl-carbamoyl]-2-methyl-propyl}-2-dimethylamino-3-methyl-butyramide,
ss) N-(1-{[4-(2-{2-[(Benzothiazol-2-ylmethyl)-carbamoyl]-1-methylsulfanyl-ethyl}-pyrrolidin-1-yl)-1-sec-butyl-2-methoxy-4-oxo-butyl]-methyl-carbamoyl}-2-methyl-propyl)-2-dimethylamino-3-methyl-butyramide,
tt) N-{1-[(1-sec-Butyl-2-methoxy-4-{2-[1-methylsulfanyl-2-(2-thiophen-2-yl-ethylcarbamoyl)-ethyl]-pyrrolidin-1-yl}-4-oxo-butyl)-methyl-carbamoyl]-2-methyl-propyl}-2-dimethylamino-3-methyl-butyramide,
uu) N-{1-[(1-sec-Butyl-2-methoxy-4-{2-[1-methylsulfanyl-2-(2-pyridin-3-yl-ethylcarbamoyl)-ethyl]-pyrrolidin-1-yl}-4-oxo-butyl)-methyl-carbamoyl]-2-methyl-propyl}-2-dimethylamino-3-methyl-butyramide,
vv) N-{1-[(1-sec-Butyl-2-methoxy-4-{2-[1-methylsulfanyl-2-(2-pyridin-2-yl-ethylcarbamoyl)-ethyl]-pyrrolidin-1-yl}-4-oxo-butyl)-methyl-carbamoyl]-2-methyl-propyl}-2-dimethylamino-3-methyl-butyramide,
ww) N-(1-{[1-sec-Butyl-2-methoxy-4-(2-{1-methylsulfanyl-2-[(pyridin-4-ylmethyl)-carbamoyl]-ethyl}-pyrrolidin-1-yl)-4-oxo-butyl]-methyl-carbamoyl}-2-methyl-propyl)-2-dimethylamino-3-methyl-butyramide,
xx) N-(1-{[1-sec-Butyl-4-(2-{2-[2-(3H-imidazol-4-yl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide,
yy) N-{1-[(1-sec-Butyl-2-methoxy-4-{2-[1-methylsulfanyl-2-(thiazol-2-ylcarbamoyl)-ethyl]-pyrrolidin-1-yl}-4-oxo-butyl)-methyl-carbamoyl]-2-methyl-propyl}-2-dimethylamino-3-methyl-butyramide, zz) N-{1-[(1-sec-Butyl-2-methoxy-4-{2-[1-methylsulfanyl-2-(naphthalen-2-ylcarbamoyl)-ethyl]-pyrrolidin-1-yl}-4-oxo-butyl)-methyl-carbamoyl]-2-methyl-propyl}-2-dimethylamino-3-methyl-butyramide, aaa) N-[1-({1-sec-Butyl-4-[2-(2-cyclohexylcarbamoyl-1-methylsulfanyl-ethyl)-pyrrolidin-1-yl]-2-methoxy-4-oxo-butyl}-methyl-carbamoyl)-2-methyl-propyl]-2-dimethylamino-3-methyl-butyramide, bbb) N-[1-({1-sec-Butyl-4-[2-(2-{[2-(3,4-dimethoxy-phenyl)-ethyl]-methyl-carbamoyl}-1-methylsulfanyl-ethyl)-pyrrolidin-1-yl]-2-methoxy-4-oxo-butyl}-methyl-carbamoyl)-2-methyl-propyl]-2-dimethylamino-3-methyl-butyramide, ccc) N-(1-{[1-sec-Butyl-4-(2-{2-[2-(3,4-dimethoxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide, ddd) N-(1-{[1-sec-Butyl-4-(2-{2-[2-(4-chloro-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide, eee) N-[1-({1-sec-Butyl-2-methoxy-4-oxo-4-[2-(1-pentylsulfanyl-2-phenethylcarbamoyl-ethyl)-pyrrolidin-1-yl]-butyl}-methyl-carbamoyl)-2-methyl-propyl]-2-dimethylamino-3-methyl-butyramide, fff) N-{1-[(1-sec-Butyl-2-methoxy-4-{2-[1-(naphthalen-2-ylsulfanyl)-2-phenethylcarbamoyl-ethyl]-pyrrolidin-1-yl}-4-oxo-butyl)-methyl-carbamoyl]-2-methyl-propyl}-2-dimethylamino-3-methyl-butyramide, ggg) N-{1-[(1-sec-Butyl-4-{2-[1-(4-fluoro-benzylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide, hhh) N-{1-[(1-sec-Butyl-4-{2-[1-(furan-2-ylmethylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide, iii) N-(1-{[1-sec-Butyl-2-methoxy-4-(2-{2-[2-(4-methoxy-phenyl)-ethylcarbamoyl]-1-methylsulfanyl-ethyl}-pyrrolidin-1-yl)-4-oxo-butyl]-methyl-carbamoyl}-2-methyl-propyl)-2-dimethylamino-3-methyl-butyramide, jjj) N-{1-[(1-sec-Butyl-2-methoxy-4-{2-[1-methylsulfanyl-2-(4-[1,2,3]thiadiazol-4-yl-benzylcarbamoyl)-ethyl]-pyrrolidin-1-yl}-4-oxo-butyl)-methyl-carbamoyl]-2-methyl-propyl}-2-dimethylamino-3-methyl-butyramide, kkk) N-{1-[(4-{2-[2-(1-Benzyl-piperidin-4-ylcarbamoyl)-1-methylsulfanyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide, lll) N-(1-{[1-sec-Butyl-4-(2-{1-tert-butylsulfanyl-2-[2-(4-hydroxy-phenyl)-ethylcarbamoyl]-ethyl}-pyrrolidin-1-yl)-2-methoxy-4-oxo-butyl]-methyl-carbamoyl}-2-methyl-propyl)-2-dimethylamino-3-methyl-butyramide, mmm) N-(1-{[1-sec-Butyl-4-(2-{1-tert-butylsulfanyl-2-[2-(3-hydroxy-phenyl)-ethylcarbamoyl]-ethyl}-pyrrolidin-1-yl)-2-methoxy-4-oxo-butyl]-methyl-carbamoyl}-2-methyl-propyl)-2-dimethylamino-3-methyl-butyramide, nnn) N-(1-{[1-sec-Butyl-4-(2-{1-tert-butylsulfanyl-2-[2-(2-hydroxy-phenyl)-ethylcarbamoyl]-ethyl}-pyrrolidin-1-yl)-2-methoxy-4-oxo-butyl]-methyl-carbamoyl}-2-methyl-propyl)-2-dimethylamino-3-methyl-butyramide, ooo) N-(1-{[1-sec-Butyl-4-(2-{1-dimethylcarbamoylmethylsulfanyl-2-[2-(3-hydroxy-phenyl)-ethylcarbamoyl]-ethyl}-pyrrolidin-1-yl)-2-methoxy-4-oxo-butyl]-methyl-carbamoyl}-2-methyl-propyl)-2-dimethylamino-3-methyl-butyramide, ppp) N-[1-({1-sec-Butyl-4-[2-(1-dimethylcarbamoylmethylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide, and qqq) Ethyl-carbamic acid 2-{1-[1-(4-{[2-(2-dimethylamino-3-methyl-butyrylamino)-3-methyl-butyryl]-methyl-amino}-3-methoxy-5-methyl-heptanoyl)-pyrrolidin-2-yl]-2-phenethylcarbamoyl-ethylsulfanyl}-ethyl ester.

When $R^1$ and $R^2$ are methyl, $R^3$ is hydrogen and n is an integer of 0, preferred compounds of formula (I) are those for which $R^4$ is phenyl, 4-hydroxyphenyl (R), 4-AcNHPh- (i.e., 4-acetoaminophenyl), t-butyl (R), ethyl, i-propyl, , t-butyl, benzyl, 3-hydroxyphenyl, 2-hydroxyphenyl, 2-hydroxyethyl, 2-acetoxyethyl, allyl or n-pentyl and $R^5$ is phenylethylamino. In particular, the following compounds of formula (I) are preferred in the present invention;

N-[1-({1-sec-Butyl-2-methoxy-4-oxo-4-[2-(2-phenethylcarbamoyl-1-phenylsulfanyl-ethyl)-pyrrolidin-1-yl]-butyl}-methyl-carbamoyl)-2-methyl-propyl]-2-dimethylamino-3-methyl-butyramide, N-{1-[(1-sec-Butyl-4-{2-[1-(R)-(4-hydroxy-phenylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide, N-{1-[(4-{2-[1-(4-Acetylamino-phenylsulfanyl)-2-phenethylcarbamoyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide, N-[1-({1-sec-Butyl-4-[2-(1-(R)-tert-butylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide, N-[1-({1-sec-Butyl-4-[2-(1-ethylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide, N-[1-({1-sec-Butyl-4-[2-(1-isopropylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide, N-[1-({1-sec-Butyl-4-[2-(1-tert-butylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide, N-[1-({4-[2-(1-Benzylsulfanyl-2-phenethylcarbamoyl-ethyl)-pyrrolidin-1-yl]-1-sec-butyl-2-methoxy-4-oxo-butyl}-methyl-carbamoyl)-2-methyl-propyl]-2-dimethylamino-3-methyl-butyramide, N-{1-[(1-sec-Butyl-4-{2-[1-(3-hydroxy-phenylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide, N-{1-[(1-sec-Butyl-4-{2-[1-(2-hydroxy-ethylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide, Acetic acid 2-{1-[1-(4-{[2-(2-dimethylamino-3-methyl-butyrylamino)-3-methyl-butyryl]-methyl-amino}-3-methoxy-5-methyl-heptanoyl)-pyrrolidin-2-yl]-2-phenethylcarbamoyl-ethylsulfanyl}-ethyl ester, N-[1-({4-[2-(1-Allylsulfanyl-2-phenethylcarbamoyl-ethyl)-pyrrolidin-1-yl]-1-sec-butyl-2-methoxy-4-oxo-butyl}-methyl-carbamoyl)-2-methyl-propyl]-2-dimethylamino-3-methyl-butyramide, and N-[1-({1-sec-Butyl-2-methoxy-4-oxo-4-[2-(1-pentylsulfanyl-2-phenethylcarbamoyl-ethyl)-pyrrolidin- 1-yl]-butyl}-methyl-carbamoyl)-2-methyl-propyl]-2-dimethylamino-3-methyl-butyramide.

Other preferred compounds of formula (I) are those wherein $R^1$ and $R^2$ are methyl, $R^3$ is hydrogen and n is 0.

Other preferred compounds of formula (I) are those for which $R^4$ is methyl and $R^5$ is selected from 4-hydroxyphenylethylamino; N-methylphenethylamino; 2-hydroxyphenylethylamino; 3-hydroxyphenylethylamino; benzylhydrazino; 4,3-dimethoxyphenylethylamino; thienylethylamino; and 2-pyridylethylamino. Examples of such compounds include:

N-(1-{[1-sec-Butyl-4-(2-{2-[2-(4-hydroxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide, N-{1-[(1-sec-Butyl-2-methoxy-4-{2-[2-(methyl-phenethyl-carbamoyl]-1-methylsulfanyl-ethyl]-pyrrolidin-1-yl}-4-oxo-butyl)-methyl-carbamoyl]-2-methyl-propyl}-2-dimethylamino-3-methyl-butyramide, N-(1-{[1-sec-Butyl-4-(2-{2-[2-(2-hydroxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide, N-(1-{[1-sec-Butyl-4-(2-{2-[2-(3-hydroxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide, N-{1-[(4-{2-[2-(N'-Benzyl-hydrazinocarbonyl)-1-methylsulfanyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide, N-{1-[(1-sec-Butyl-2-methoxy-4-{2-[1-methylsulfanyl-2-(2-thiophen-2-yl-ethylcarbamoyl)-ethyl]-pyrrolidin-1-yl}-4-oxo-butyl)-methyl-carbamoyl]-2-methyl-propyl}-2-dimethylamino-3-methyl-butyramide, N-{1-[(1-sec-Butyl-2-methoxy-4-{2-[1-methylsulfanyl-2-(2-pyridin-3-yl-ethylcarbamoyl)-ethyl]-pyrrolidin-1-yl}-4-oxo-butyl)-methyl-carbamoyl]-2-methyl-propyl}-2-dimethylamino-3-methyl-butyramide, N-{1-[(1-sec-Butyl-2-methoxy-4-{2-[1-methylsulfanyl-2-(2-pyridin-2-yl-ethylcarbamoyl)-ethyl]-pyrrolidin-1-yl}-4-oxo-butyl)-methyl-carbamoyl]-2-methyl-propyl}-2-dimethylamino-3-methyl-butyramide, and N-(1-{[1-sec-Butyl-4-(2-{2-[2-(3,4-dimethoxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide.

Other compounds of interest include compounds of formula (I) wherein $R^1$ and $R^2$ are methyl, $R^3$ is hydrogen and n is 1. An example of such a compound is N-[1-({1-sec-Butyl-4-[2-(1-methanesulfinyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide.

Other compounds of interest include compounds of formula (1) wherein $R^1$ and $R^2$ are methyl, $R^3$ is hydrogen and n is 2. An example of such a compound is the compound N-[1-({1-sec-Butyl-4-[2-(1-methanesulfonyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide.

Another preferred embodiment of the present invention is a compound of formula (I) wherein $R^1$ is methyl, $R^2$ and $R^3$ are hydrogen and n is 0. Examples of such compounds are selected from the group consisting of.

a) N-[1-({1-sec-Butyl-4-[2-(1-ethylsulfanyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide, b) N-[1-({1-sec-Butyl-2-methoxy-4-oxo-4-[2-(2-phenethylcarbamoyl-1-phenylsulfanyl-ethyl)-pyrrolidin-1-yl]-butyl}-methyl-carbamoyl)-2-methyl-propyl]-3-methyl-2-methylamino-butyramide, c) N-[1-({1-sec-Butyl-4-[2-(1-tert-butylsulfanyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide, d) N-[1-({1-sec-Butyl-2-methoxy-4-[2-(1-methylsulfanyl-2-phenethylcarbamoyl-ethyl)-pyrrolidin-1-yl]-4-oxo-butyl}-methyl-carbamoyl)-2-methyl-propyl]-3-methyl-2-methylamino-butyramide, e) N-[1-({1-sec-Butyl-4-[2-(1-isopropylsulfanyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide, f) N-{1-[(1-sec-Butyl-2-methoxy-4-oxo-4-{2-[2-phenethylcarbamoyl-1-(2-methyl-propane-2-sulfonyl)-ethyl]-pyrrolidin-1-yl}-butyl)-methyl-carbamoyl]-2-methyl-propyl}-3-methyl-2-methylamino-butyramide, g) N-(1-{[1-sec-Butyl-4-(2-{2-[2-(3-hydroxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-3-methyl-2-methylamino-butyramide, and h) N-(1-{[1-sec-Butyl-4-(2-{1-tert-butylsulfanyl-2-[2-(3-hydroxy-phenyl)-ethylcarbamoyl]-ethyl}-pyrrolidin-1-yl)-2-methoxy-4-oxo-butyl]-methyl-carbamoyl}-2-methyl-propyl)-3-methyl-2-methylamino-butyramide.

When $R^1$ is methyl, $R^2$ and $R^3$ are hydrogen and n is 0, preferred compounds of formula (I) are those for which $R^4$ is ethyl, phenyl, t-butyl, methyl, i-propyl and $R^5$ is phenyl-ethylamino or 3-hydroxyphenylethylamino. In particular, the following compounds of formula (I) are preferred:

N-[1-({1-sec-Butyl-4-[2-(1-ethylsulfanyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide, N-[1-({1-sec-Butyl-2-methoxy-4-oxo-4-[2-(2-phenethylcarbamoyl-1-phenylsulfanyl-ethyl)-pyrrolidin-1-yl]-butyl}-methyl-carbamoyl)-2-methyl-propyl]-3-methyl-2-methylamino-butyramide, N-[1-({1-sec-Butyl-2-methoxy-4-[2-(1-methylsulfanyl-2-phenethylcarbamoyl-ethyl)-pyrrolidin-1-yl]-4-oxo-butyl}-methyl-carbamoyl)-2-methyl-propyl]-3-methyl-2-methylamino-butyramide, N-[1-({1-sec-Butyl-4-[2-(1-isopropylsulfanyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide, and N-(1-{[1-sec-Butyl-4-(2-{2-[2-(3-hydroxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-3-methyl-2-methylamino-butyramide.

Another preferred embodiment of the present invention concerns compound of formula (I) wherein $R^1$ is methyl, $R^2$ and $R^3$ are hydrogen and n is 2. Examples of such compounds include:

a) N-[1-({1-sec-Butyl-4-[2-(1-ethanesulfonyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide, b) N-[1-({4-[2-(1-Benzenesulfonyl-2-phenethylcarbamoyl-ethyl)-pyrrolidin-1-yl]-1-sec-butyl-2-methoxy-4-oxo-butyl}-methyl-carbamoyl)-2-methyl-propyl]-3-methyl-2-methylamino-butyramide, c) N-[1-({1-sec-Butyl-4-[2-(1-methanesulfonyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide, and d) N-{1-[(1-sec-Butyl-2-methoxy-4-oxo-4-{2-[2-phenethylcarbamoyl-1-(propane-2-sulfonyl)-ethyl]-pyrrolidin-1-yl}-butyl)-methyl-carbamoyl]-2-methyl-propyl}-3-methyl-2-methylamino-butyramide.

When $R^1$ is methyl, $R^2$ and $R^3$ are hydrogen, and n is 2, preferably $R^4$ is methyl and $R^5$ is phenylethylamino. An example of such a compound is N-[1-({1-sec-Butyl-4-[2-(1-methanesulfonyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide.

Another preferred embodiment of the present invention concerns compounds of formula (I) wherein $R^1$ and $R^3$ are methyl, $R^2$ is hydrogen and n is 0. Examples of such compounds are selected from the group consisting of:

a) N-[1-({1-sec-Butyl-2-methoxy-4-[2-(1-methylsulfanyl-2-phenethylcarbamoyl-propyl)-pyrrolidin-1-yl]-4-oxo-butyl}-methyl-carbamoyl)-2-methyl-propyl]-2-methylamino-3-methyl-butyramide, and b) N-[-({1-sec-Butyl-4-[2-(1-tert-butylsulfanyl-2-phenethylcarbamoyl-propyl)-pyrrolidin-1-yl]-2-methoxy-4-oxo-butyl}-methyl-carbamoyl)-2-methyl-propyl]-2-methylamino-3-methyl-butyramide.

Another preferred embodiment of the present invention concerns compound of formula (I) wherein $R^1$, $R^2$ and $R^3$ are methyl and n is 0. Examples of such compounds are selected from the group consisting of:

a) N-[1-({1-sec-Butyl-2-methoxy-4-[2-(1-methylsulfanyl-2-phenethylcarbamoyl-propyl)-pyrrolidin-1-yl]-4-oxo-butyl}-methyl-carbamoyl)-2-methyl-propyl]-2-dimethylamino-3-methyl-butyramide, b) N-[1-({1-sec-Butyl-4-[2-(1-tert-butylsulfanyl-2-phenethylcarbamoyl-propyl)-pyrrolidin-1-yl]-2-methoxy-4-oxo-butyl}-methyl-carbamoyl)-2-methyl-propyl]-2-dimethylamino-3-methyl-butyramide, c) N-{1-[(1-sec-Butyl-4-{2-[1-(2-hydroxy-ethylsulfanyl)-2-phenethylcarbamoyl-propyl]-pyrrolidin-1-yl}-2-methoxy-4-oxo-butyl)-methyl-carbamoyl]-2-methyl-propyl}-2-dimethylamino-3-methyl-butyramide, d) N-{1-[(1-sec-Butyl-4-{2-[1-(4-hydroxy-phenylsulfanyl)-2-phenethylcarbamoyl-propyl]-pyrrolidin-1-yl}-2-methoxy-4-oxo-butyl)-methyl-carbamoyl]-2-methyl-propyl}-2-dimethylamino-3-methyl-butyramide, e) N-{1-[(1-sec-Butyl-4-{2-[1-(3-hydroxy-phenylsulfanyl)-2-phenethylcarbamoyl-propyl]-pyrrolidin-1-yl}-2-methoxy-4-oxo-butyl)-methyl-carbamoyl]-2-methyl-propyl}-2-dimethylamino-3-methyl-butyramide, f) N-{1-[(1-sec-Butyl-4-{2-[1-(2-hydroxy-phenylsulfanyl)-2-phenethylcarbamoyl-propyl]-pyrrolidin-1-yl}-2-methoxy-4-oxo-butyl)-methyl-carbamoyl]-2-methyl-propyl}-2-dimethylamino-3-methyl-butyramide, g) N-(1-{[1-sec-Butyl-4-(2-{2-[2-(4-hydroxy-phenyl)-ethylcarbamoyl]-1-t-butylsulfanyl-propyl}-pyrrolidin-1-yl)-2-methoxy-4-oxo-butyl]-methyl-carbamoyl}-2-methyl-propyl)-2-dimethylamino-3-methyl-butyramide, h) N-(1-{[1-sec-Butyl-4-(2-{2-[2-(3-hydroxy-phenyl)-ethylcarbamoyl]-1-t-butylsulfanyl-propyl}-pyrrolidin-1-yl)-2-methoxy-4-oxo-butyl]-methyl-carbamoyl}-2-methyl-propyl)-2-dimethylamino-3-methyl-butyramide, i) N-(1-{[-sec-Butyl-4-(2-{2-[2-(2-hydroxy-phenyl)-ethylcarbamoyl]-1-t-butylsulfanyl-propyl}-pyrrolidin-1-yl)-2-methoxy-4-oxo-butyl]-methyl-carbamoyl}-2-methyl-propyl)-2-dimethylamino-3-methyl-butyramide, j) N-(1-{[1-sec-Butyl-4-(2-{2-[2-(4-hydroxy-phenyl)-ethylcarbamoyl]-1-methylsulfanyl-propyl}-pyrrolidin-1-yl)-2-methoxy-4-oxo-butyl]-methyl-carbamoyl}-2-methyl-propyl)-2-dimethylamino-3-methyl-butyramide, k) N-(1-{[1-sec-Butyl-4-(2-{2-[2-(3-hydroxy-phenyl)-ethylcarbamoyl]-1-methylsulfanyl-propyl}-pyrrolidin-1-yl)-2-methoxy-4-oxo-butyl]-methyl-carbamoyl}-2-methyl-propyl)-2-dimethylamino-3-methyl-butyramide, l) N-(1-{[1-sec-Butyl-4-(2-{2-[2-(2-hydroxy-phenyl)-ethylcarbamoyl]-1-methylsulfanyl-propyl}-pyrrolidin-1-yl)-2-methoxy-4-oxo-butyl]-methyl-carbamoyl}-2-methyl-propyl)-2-dimethylamino-3-methyl-butyramide, m) N-(1-{[1-sec-Butyl-4-(2-{2-[2-(3-hydroxy-phenyl)-ethylcarbamoyl]-1-pentylsulfanyl-propyl}-pyrrolidin-1-yl)-2-methoxy-4-oxo-butyl]-methyl-carbamoyl}-2-methyl-propyl)-2-dimethylamino-3-methyl-butyramide, n) N-[1-({1-sec-Butyl-4-[2-(2-{[2-(3-hydroxy-phenyl)-ethyl]-methyl-carbamoyl}-1-methylsulfanyl-propyl)-pyrrolidin-1-yl]-2-methoxy-4-oxo-butyl}-methyl-carbamoyl)-2-methyl-propyl]-2-dimethylamino-3-methyl-butyramide, o) N-[1-({1-sec-Butyl-4-[2-(1-ethylsulfanyl-2-{[2-(3-hydroxy-phenyl)-ethyl]-methyl-carbamoyl}-propyl)-pyrrolidin-1-yl]-2-methoxy-4-oxo-butyl}-methyl-carbamoyl)-2-methyl-propyl]-2-dimethylamino-3-methyl-butyramide, p) N-(1-{[1-sec-Butyl-4-(2-{1-ethylsulfanyl-2-[2-(3-hydroxy-phenyl)-ethylcarbamoyl]-propyl}-pyrrolidin-1-yl)-2-methoxy-4-oxo-butyl]-methyl-carbamoyl}-2-methyl-propyl)-2-dimethylamino-3-methyl-butyramide, and q) Ethyl-carbamic acid 3-(2-{3-[1-(4-{[2-(2-dimethylamino-3-methyl-butyrylamino)-3-methyl-butyryl]-methyl-amino}-3-methoxy-5-methyl-heptanoyl)-pyrrolidin-2-yl]-2-methyl-3-methylsulfanyl-propionylamino}-ethyl)-phenyl ester.

Preferably, when $R^1$, $R^2$ and $R^3$ are methyl or ethyl (preferably methyl) and n is 0, $R^4$ is methyl or ethyl and $R^5$ is phenylethylamino, 3-hydroxyphenylethylamino or 3-hydroxyphenylethyl-N-methyamino. An example of such a compound includes N-[1-({1-sec-Butyl-2-methoxy-4-[2-(1-methylsulfanyl-2-phenethylcarbamoyl-propyl)-pyrrolidin-1-yl]-4-oxo-butyl}-methyl-carbamoyl)-2-methyl-propyl]-2-dimethylamino-3-methyl-butyramide, N-(1-{[1-sec-Butyl-4-(2-{2-[2-(3-hydroxy-phenyl)-ethylcarbamoyl]-1-methylsulfanyl-propyl}-pyrrolidin-1-yl)-2-methoxy-4-oxo-butyl]-methyl-carbamoyl}-2-methyl-propyl)-2-dimethylamino-3-methyl-butyramide, N-[1-({1-sec-Butyl-4-[2-(2-{[2-(3-hydroxy-phenyl)-ethyl]-methyl-carbamoyl}-1-methylsulfanyl-propyl)-pyrrolidin-1-yl]-2-.methoxy-4-oxo-butyl}-methyl-carbamoyl)-2-methyl-propyl]-2-dimethylamino-3-methyl-butyramide, N-[1-({1-sec-Butyl-4-[2-(1-ethylsulfanyl-2-{[2-(3-hydroxy-phenyl)-ethyl]carbamoyl}-propyl)-pyrrolidin-1-yl]-2-methoxy-4-oxo-butyl}-methyl-carbamoyl)-2-methyl-propyl]-2-dimethylamino-3-methyl-butyramide, and N-(1-{[1-sec-Butyl-4-(2-{1-ethylsulfanyl-2-[2-(3-hydroxy-phenyl)-ethylcarbamoyl]-propyl}-pyrrolidin-1-yl)-2-methoxy-4-oxo-butyl]-methyl-carbamoyl}-2-methyl-propyl)-2-dimethylamino-3-methyl-butyramide.

All of the stereoisomers in the formula (I) are included in the scope of the invention. However, compounds having the stereostructural formula (I-1),

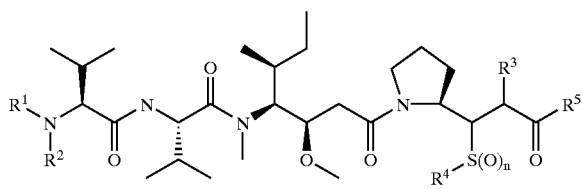

(I-1)

wherein $R^1$, $R^2$, $R^3$, $R^4$, $R^5$ and n are as defined above, as well as pharmaceutically acceptable salts thereof, are preferred.

Compounds of formula (I) and formula (I-1) wherein the $R^4S(O)n$ group has an R-configuration and the $R^3$ group has an S-configuration have particularly advantageous antitumor activity.

The compounds of the invention are effective at inhibiting or preventing the growth of tumors in premalignant and malignant cells and are useful in preventing carcinomas from forming solid tumors. The compounds are particularly useful in the treatment of colorectal cancer, lung cancer, breast cancer, stomach cancer, cervical cancer and bladder cancer. The compounds of this invention can be used to treat such tumors, to retard the development of such tumors, and to prevent the increase in number of tumors.

The anticancer therapeutic activity of compounds of this invention is demonstrated by various standard in vitro assays. The assays described below and in the examples are known to indicate antitumor and anticancer activity and are assays used by those skilled in the art to assess compounds for cancer therapeutics.

Compounds of this invention have the structure depicted in formula I, and anticancer activity as determined by any standard assay, especially assays for apoptosis. The compounds are particularly effective to induce apoptosis in carcinoma cells, causing the death of the cell. Thus a compound has the desired activity if the compound causes carcinoma cells to die when the cells are exposed to the compounds. Carcinoma cells for assays (for example breast, lung, colorectal, etc.) are readily obtained from cell depositories such as the American Type Culture Collection (ATCC) or may be isolated by skilled persons from cancer patients. The type of cancer against which the compound is most active is determined by the type of cell used in the assays.

Carcinoma cells, grown in culture, may be incubated with a specific test compound and changes in cell viability may be determined for example, by dyes which selectively stain dead cells or by optical density (O.D.) measurement. If more than 10% of cells have died, the compound is active in inducing apoptosis. The compounds may not directly kill the cells (cellular toxicity) but may modulate certain intra- or extracellular events which result in apoptosis.

The anticancer activity of the compounds of this invention may also be determined by assays that access the effects of compounds on cell growth and differentiation. Cell growth inhibition may be determined by adding the test compound to carcinoma cells in culture with dyes or radioactive precursors, and determining by microscopic cell counting, scintillation counting, or O.D. measurement whether the number of cells has increased over the incubation period. If the number of cells has not increased, growth has been inhibited and the compound is regarded as having therapeutic activity. Similarly, the proportion of cells which have become differentiated after addition of a test compound may be determined by known methods (ie. measuring oxidative burst in HL-60 cells, an indicator of differentiation, by NBT). If 10% or more cells have differentiated, then the compound is regarded as having therapeutic activity.

In vivo assays are also useful to demonstrate anticancer activity. Compounds of this invention are effective in reducing the size and/or the number of tumors in laboratory animals such as mice in which tumor growth has been induced. The type of tumor indicates the type of cancer against which primary activity is expected. Specific tumors may be induced by perturbing specific tissues with carcinogens, or by injecting specific types of carcinoma cells. The compounds of the present invention show significant prophylactic and therapeutic activity when evaluated against NMU-induced mammary (breast) tumors in rats. Surprisingly the doses and regimens which are effective are free of significant toxicity. The compounds also show efficacy in reducing number of tumors during the course of the experiment (i.e. chemoprevention) at doses and regimens not associated with toxicity. Furthermore, the compounds are therapeutically active, i.e. are able to effect regression of established first primary tumors. The compounds are also preventitive, i.e. able to significantly prevent formation of new tumors.

In Vitro Assay

Antiproliferative activity assay was carried out as follows. A single suspension of tumor cells was inoculated to the serially diluted 96-well microtestplate. Then the testplate was incubated in the 5% $CO_2$ ambience at 37° C. for 4 days ($2-3\times10^3$ cells/well). The degree of cell growth in a monolayer was measured by using WST-8 (Dojindo, Japan). $IC_{50}$ values of drugs against tumor cells were calculated as the concentration of drug yielding 50% OD of the control growth. The results are shown in the following table I.

TABLE I

In vitro antitumor activity of selected compounds

| Compound | HCT 116 $IC_{50}$ (nM) |
|---|---|
| N-[1-({1-sec-Butyl-2-methoxy-4-oxo-4-[2-(2-phenethyl-carbamoyl-1-phenylsulfanyl-ethyl)-pyrrolidin-1-yl]-butyl}-methyl-carbamoyl)-2-methyl-propyl]-2-dimethylamino-3-methyl-butyramide | 0.33 |
| N-[1-({1-sec-Butyl-4-[2-(1-methanesulfonyl-2-phenethyl-carbamoyl-ethyl)-pyrrolidin-1-yl]-2-methoxy-4-oxo-butyl}-methyl-carbamoyl)-2-methyl-propyl]-2-dimethylamino-3-methyl-butyramide | 0.44 |
| N-{1-[(1-sec-Butyl-4-{2-[1-(R)-(4-hydroxy-phenyl-sulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide | 0.6 |
| N-{1-[(4-{2-[1-(4-Acetylamino-phenylsulfanyl)-2-phenethylcarbamoyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide | 0.98 |
| N-[1-({1-sec-Butyl-4-[2-(1-ethylsulfanyl-2-phenethyl-carbamoyl-ethyl)-pyrrolidin-1-yl]-2-methoxy-4-oxo-butyl}-methyl-carbamoyl)-2-methyl-propyl]-3-methyl-2-methyl-amino-butyramide | 0.5 |
| N-[1-({1-sec-Butyl-2-methoxy-4-oxo-4-[2-(2-phenethyl-carbamoyl-1-phenylsulfanyl-ethyl)-pyrrolidin-1-yl]-butyl}-methyl-carbamoyl)-2-methyl-propyl]-3-methyl-2-methyl-amino-butyramide | 0.87 |
| N-[1-({1-sec-Butyl-4-[2-(1-(R)-tert-butylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide | 0.04 |
| N-[1-({1-sec-Butyl-4-[2-(1-ethylsulfanyl-2-phenethyl-carbamoyl-ethyl)-pyrrolidin-1-yl]-2-methoxy-4-oxo-butyl}-methyl-carbamoyl)-2-methyl-propyl]-2-dimethylamino-3-methyl-butyramide | 0.78 |

TABLE I-continued

In vitro antitumor activity of selected compounds

| Compound | HCT 116 IC$_{50}$ (nM) |
|---|---|
| N-[1-({1-sec-Butyl-4-[2-(1-tert-butylsulfanyl-2-phenethyl-carbamoyl-ethyl)-pyrrolidin-1-yl]-2-methoxy-4-oxo-butyl}-methyl-carbamoyl)-2-methyl-propyl]-2-dimethylamino-3-methyl-butyramide | 0.17 |
| N-[1-({4-[2-(1-Benzylsulfanyl-2-phenethylcarbamoyl-ethyl)-pyrrolidin-1-yl]-1-sec-butyl-2-methoxy-4-oxo-butyl}-methyl-carbamoyl)-2-methyl-propyl]-2-dimethylamino-3-methyl-butyramide | 0.52 |
| N-{1-[(1-sec-Butyl-4-{2-[1-(3-hydroxy-phenylsulfanyl)-2-phenethylcarbamoyl-ethyl]-pyrrolidin-1-yl}-2-methoxy-4-oxo-butyl)-methyl-carbamoyl]-2-methyl-propyl}-2-dimethyl-amino-3-methyl-butyramide | 0.3 |
| N-[1-({1-sec-Butyl-2-methoxy-4-[2-(1-methylsulfanyl-2-phenethylcarbamoyl-ethyl)-pyrrolidin-1-yl]-4-oxo-butyl}-methyl-carbamoyl)-2-methyl-propyl]-3-methyl-2-methyl-amino-butyramide | 0.12 |
| N-[1-({1-sec-Butyl-4-[2-(1-methanesulfonyl-2-phenethyl-carbamoyl-ethyl)-pyrrolidin-1-yl]-2-methoxy-4-oxo-butyl}-methyl-carbamoyl)-2-methyl-propyl]-3-methyl-2-methyl-amino-butyramide | 0.77 |
| N-[1-({1-sec-Butyl-4-[2-(1-isopropylsulfanyl-2-phenethyl-carbamoyl-ethyl)-pyrrolidin-1-yl]-2-methoxy-4-oxo-butyl}-methyl-carbamoyl)-2-methyl-propyl]-3-methyl-2-methyl-amino-butyramide | 0.65 |
| N-{1-[(1-sec-Butyl-4-{2-[1-(2-hydroxy-ethylsulfanyl)-2-phenethylcarbamoyl-ethyl]-pyrrolidin-1-yl}-2-methoxy-4-oxo-butyl)-methyl-carbamoyl]-2-methyl-propyl}-2-dimethyl-amino-3-methyl-butyramide | 0.39 |
| Acetic acid 2-{1-[1-(4-{[2-(2-dimethylamino-3-methyl-butyrylamino)-3-methyl-butyryl]-methyl-amino}-3-methoxy-5-methyl-heptanoyl)-pyrrolidin-2-yl]-2-phenethylcarbamoyl-ethylsulfanyl}-ethyl ester | 0.19 |
| N-(1-{[1-sec-Butyl-4-(2-{2-[2-(4-hydroxy-phenyl)-ethyl-carbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide | 0.6 |
| N-{1-[(1-sec-Butyl-2-methoxy-4-{2-[2-(methyl-phenethyl-carbamoyl)-1-methylsulfanyl-ethyl]-pyrrolidin-1-yl}-4-oxo-butyl)-methyl-carbamoyl]-2-methyl-propyl}-2-dimethylamino-3-methyl-butyramide | 0.87 |
| N-(1-{[1-sec-Butyl-4-(2-{2-[2-(2-hydroxy-phenyl)-ethyl-carbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide | 0.64 |
| N-(1-{[1-sec-Butyl-4-(2-{2-[2-(3-hydroxy-phenyl)-ethyl-carbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide | 0.26 |
| N-[1-({1-sec-Butyl-2-methoxy-4-[2-(1-methylsulfanyl-2-phenethylcarbamoyl-propyl)-pyrrolidin-1-yl]-4-oxo-butyl}-methyl-carbamoyl)-2-methyl-propyl]-2-dimethylamino-3-methyl-butyramide | 0.04 |
| N-[1-({4-[2-(1-Allylsulfanyl-2-phenethylcarbamoyl-ethyl)-pyrrolidin-1-yl]-1-sec-butyl-2-methoxy-4-oxo-butyl}-methyl-carbamoyl)-2-methyl-propyl]-2-dimethylamino-3-methyl-butyramide | 0.55 |
| N-{1-[(1-sec-Butyl-2-methoxy-4-{2-[1-methylsulfanyl-2-(2-thiophen-2-yl-ethylcarbamoyl)-ethyl]-pyrrolidin-1-yl}-4-oxo-butyl)-methyl-carbamoyl]-2-methyl-propyl}-2-dimethylamino-3-methyl-butyramide | 0.5 |
| N-{1-[(1-sec-Butyl-2-methoxy-4-{2-[1-methylsulfanyl-2-(2-pyridin-3-yl-ethylcarbamoyl)-ethyl]-pyrrolidin-1-yl}-4-oxo-butyl)-methyl-carbamoyl]-2-methyl-propyl}-2-dimethyl-amino-3-methyl-butyramide | 0.91 |
| N-{1-[(1-sec-Butyl-2-methoxy-4-{2-[1-methylsulfanyl-2-(2-pyridin-2-yl-ethylcarbamoyl)-ethyl]-pyrrolidin-1-yl}-4-oxo-butyl)-methyl-carbamoyl]-2-methyl-propyl}-2-dimethyl-amino-3-methyl-butyramide | 0.9 |
| N-(1-{[1-sec-Butyl-4-(2-{2-[2-(3,4-dimethoxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide | 0.91 |
| N-[1-({1-sec-Butyl-2-methoxy-4-oxo-4-[2-(1-pentylsul-fanyl-2-phenethylcarbamoyl-ethyl)-pyrrolidin-1-yl]-butyl}-methyl-carbamoyl)-2-methyl-propyl]-2-dimethylamino-3-methyl-butyramide | 0.75 |
| N-[1-({1-sec-Butyl-2-methoxy-4-[2-(1-methylsulfanyl-2-phenethylcarbamoyl-propyl)-pyrrolidin-1-yl]-4-oxo-butyl}-methylcarbamoyl)-2-methyl-propyl]-2-methylamino-3-methyl-butyramide | 1.0 |
| N-(1-{[1-sec-Butyl-4-(2-{2-[2-(3-hydroxy-phenyl)-ethyl-carbamoyl]-1-methylsulfanyl-propyl}-pyrrolidin-1-yl)-2-methoxy-4-oxo-butyl]-methyl-carbamoyl}-2-methyl-propyl)-2-dimethylamino-3-methyl-butyramide | 0.19 |
| N-[1-({1-sec-Butyl-4-[2-(2-{[2-(3-hydroxy-phenyl)-ethyl]-methyl-carbamoyl}-1-methylsulfanyl-propyl)-pyrrolidin-1-yl]-2-methoxy-4-oxo-butyl}-methyl-carbamoyl)-2-methyl-propyl]-2-dimethylamino-3-methyl-butyramide | 0.66 |
| N-[1-({1-sec-Butyl-4-[2-(1-ethylsulfanyl-2-{[2-(3-hydroxy-phenyl)-ethyl]-methyl-carbamoyl}-propyl)-pyrrolidin-1-yl]-2-methoxy-4-oxo-butyl}-methyl-carbamoyl)-2-methyl-propyl]-2-dimethylamino-3-methyl-butyramide | 0.11 |
| N-(1-{[1-sec-Butyl-4-(2-{1-dimethylcarbamoylmethylsul-fanyl-2-[2-(3-hydroxy-phenyl)-ethylcarbamoyl]-ethyl}-pyrrolidin-1-yl)-2-methoxy-4-oxo-butyl]-methyl-carbamoyl}-2-methyl-propyl)-2-dimethylamino-3-methyl-butyramide | 1.8 |
| N-(1-{[1-sec-Butyl-4-(2-{1-ethylsulfanyl-2-[2-(3-hydroxy-phenyl)-ethylcarbamoyl]-propyl}-pyrrolidin-1-yl)-2-methoxy-4-oxo-butyl]-methyl-carbamoyl}-2-methyl-propyl)-2-dimethylamino-3-methyl-butyramide | 0.84 |
| Ethyl-carbamic acid 2-{1-[1-(4-{[2-(2-dimethylamino-3-methyl-butyrylamino)-3-methyl-butyryl]-methyl-amino}-3-methoxy-5-methyl-heptanoyl)-pyrrolidin-2-yl]-2-phenethyl-carbamoyl-ethylsulfanyl}-ethyl ester | 0.97 |
| Ethyl-carbamic acid 3-(2-{3-[1-(4-{[2-(2-dimethylamino-3-methyl-butyrylamino)-3-methyl-butyryl]-methyl-amino}-3-methoxy-5-methyl-heptanoyl)-pyrrolidin-2-yl]-2-methyl-3-methylsulfanyl-propionylamino}-ethyl)-phenyl ester | 0.57 |

The maximum tolerated doses (MTD) of the following representative compounds

N-[1-({1-sec-Butyl-2-methoxy-4-[2-(1-methylsulfanyl-2-phenethylcarbamoyl-ethyl)-pyrrolidin-1-yl]-4-oxo-butyl}-methyl-carbamoyl)-2-methyl-propyl]-3-methyl-2-methylamino-butyramide, N-[1-({1-sec-Butyl-4-[2-(1-methanesulfonyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide, N-[1-({1-sec-Butyl-4-[2-(1-isopropylsulfanyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide, N-[1-({1-sec-Butyl-4-[2-(2-{[2-(3-hydroxy-phenyl)-ethyl]-methyl-carbamoyl}-1-methylsulfanyl-propyl)-pyrrolidin-1-yl]-2-methoxy-4-oxo-butyl}-methyl-carbamoyl)-2-methyl-propyl]-2-dimethylamino-3-methyl-butyramide, N-[1-({1-sec-Butyl-4-[2-(1-ethylsulfanyl-2-{[2-(3-hydroxy-phenyl)-ethyl]-methyl-carbamoyl}-propyl)-pyrrolidin-1-yl]-2-methoxy-4-oxo-butyl}-methyl-carbamoyl)-2-methyl-propyl]-2-dimethylamino-3-methyl-butyramide, N-(1-{[1-sec-Butyl-4-(2-{2-[2-(3-hydroxy-phenyl)-ethylcarbamoyl]-1-methylsulfanyl-propyl}-pyrrolidin-1-yl)-2-methoxy-4-oxo-butyl]-methyl-carbamoyl}-2-methyl-propyl)-2-dimethylamino-3-methyl-butyramide, N-(1-{[1-sec-Butyl-4-(2-{1-ethylsulfanyl-2-[2-(3-hydroxy-phenyl)-ethylcarbamoyl]-propyl}-pyrrolidin-1-yl)-2- methoxy-4-oxo-butyl]-methyl-carbamoyl}-2-methyl-propyl)-2-dimethylamino-3-methyl-butyramide of the present invention were examined by i.v. administration in mice. The respective MTD values of the compounds were 14, 18, 10, 8, 8, 2 and 2 mg/kg.

Thus the compounds of the invention are therapeutically active, producing regression or remission of solid tumors.

The present invention concerns also the use of a compound of formula (I) for the preparation of pharmaceutical compositions, preferably for the preparation of pharmaceutical compositions for the treatment of cell proliferative disorders, more preferably for the preparation of pharmaceutical compositions for the treatment of cancer, and most preferably for the treatment of colorectal cancer, lung cancer, breast cancer, stomach cancer, cervical cancer and bladder cancer.

Another aspect of the present invention is a method for treating a cell proliferative disorder comprising administering to a patient in need thereof a therapeutically effective amount of a compound of formula (I).

In accordance with the present invention, treatment of cancers is accomplished by administering a compound of the invention systemically to a patient in an amount effective to treat the cancer. By inhibiting growth of cancer (carcinoma) cells is meant stopping growth, causing apoptosis, or causing differentiation, or otherwise changing the nature of the cell to render it innocuous. The compound may also be administered prophylactically, for example to a person at risk for cancer, or a person who has already undergone effective treatment generally in a lower dosage than for treatment. The amount of compound used is dependent on the type of cancer, the amount and size of the tumors and on the requirements of the patient. In general a daily dosage of about 0.1 mg/kg to about 100 mg/kg of body weight, preferably about 20 mg/kg to about 80 mg/kg is a helpful basic range, which may be varied by the skilled practitioner depending on the characteristics and requirements of the patient and his condition. The treatment is typically carried out for a period of about three months, but this depends on the patient's condition and the practitioner's judgement. In prophylactic administration, the duration of administration again depends on the patients condition and the practitioner's plan, but will generally continue for a longer period of time than three months. For the treatments given above, the compound of the invention is administered systemically as a composition containing the compound of the invention, and a pharmaceutically acceptable carrier compatible with said compounds. In preparing such composition, any conventional pharmaceutically acceptable carrier can be used. Generally the preferred unit dosage form is tablets or capsules, which can be administered once or twice daily depending upon the weight and size of the patient. The compounds of this invention may be administered as the sole treatment, or may be used in conjunction with other chemical or biochemical treatments or with radiation or surgery.

The pharmaceutical compositions of this invention can be made up in any conventional form including: (a) a solid form for oral or suppository administration such as tablets, capsules, pills, powders, granules, and the like; (b) sterile, typically aqueous solution or suspension form for intravenous or parenteral administration and (c) preparations for topical administration such as solutions, suspensions, ointments, creams, gels, micronized powders, aerosols and the like. The pharmaceutical compositions may be sterilized and/or may contain adjuvants such as preservatives, stabilizers, wetting agents, emulsifiers, salts for varying the osmotic pressure, and/or buffers.

The compounds of the invention are especially useful in pharmaceutically acceptable oral modes. These pharmaceutical compositions contain one or more compounds of the invention or its pharmaceutically acceptable salts and its pharmaceutically acceptable hydrolyzable esters in association with a compatible pharmaceutically acceptable carrier material. Any conventional carrier material can be used. The carrier material can be an organic or inorganic inert carrier material suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutical preparations may contain other pharmaceutically active agents. Additional additives such as flavoring agents, preservatives, stabilizers, emulsifying agents, buffers and the like may be added in accordance with accepted practices of pharmaceutical compounding.

The pharmaceutical preparations can be made up in any conventional oral dosage form including a solid form for oral administration such as tablets, capsules, pills, powders, granules, and the like. A preferred oral dosage form comprises tablets, capsules of hard or soft gelatin, methylcellulose or of another suitable material easily dissolved in the digestive tract. The oral dosages contemplated in accordance with the present invention will vary in accordance with the needs of the individual patient as determined by the prescribing physician.

General Synthesis Schemes

The compounds of the present invention may be prepared by a skilled person by condensing an acid of the formula (II),

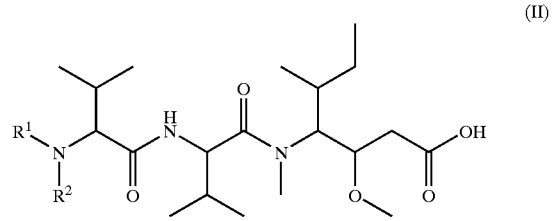

(II)

wherein $R^1$ and $R^2$ are as defined above. Preferably $R^1$ and $R^2$ are each independently alkyl, more preferably $(C_1–C_6)$-alkyl, and most preferably $(C_1–C_4)$-alkyl;

with a compound of the formula (III),

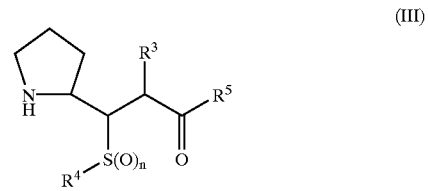

(III)

wherein $R^3$, $R^4$, $R^5$ and n are as defined above.

Compounds of formula (I) may be prepared by condensing an acid of the formula (II) with a compound of formula (III) in the presence of a condensing agent, followed, if necessary, by removal of protecting group(s) and/or a salt formation, if necessary.

Alternatively, compounds of formula (I) can be prepared by condensing an acid of the formula (IV),

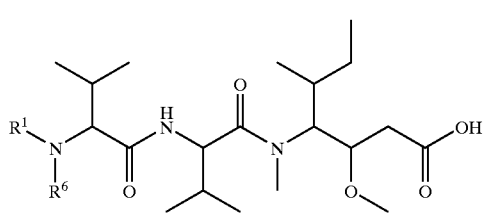

(IV)

wherein $R^1$ is hydrogen or alkyl, preferably ($C_1$–$C_6$)-alkyl, and most preferably ($C_1$–$C_4$)-alkyl; and $R^6$ is a protecting group selected from t-butoxycarbonyl, carbobenzyloxy or 9-fluorenylmethoxycarbonyl (Fmoc), with a compound of the formula (III),

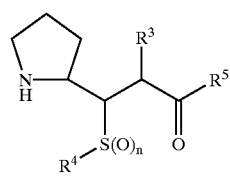

(III)

wherein $R^3$, $R^4$, $R^5$ and n are the same as defined above, in the presence of a condensing agent if necessary, by removal of protecting group(s) and/or a salt formation, if necessary. The condensing agent may be e.g. dicyclohexylcarbodiimide (DCC), diphenyl phosphorylazide (DPPA), diethyl phosphorocyanide (DEPC), benzotriazol-1-yloxy-tris(dimethylamino) phosphonium hexafluorophosphate (BOP reagent), or the like in an inert solvent such as, for example, halogenated aliphatic hydrocarbon such as chloroform and dichloromethane, ethylacetate, tetrahydrofuran (THF), dimethylformamide (DMF) or acetonitrile, if necessary in the presence of an organic base such as, for example, triethylamine or diisopropylethylamine (DIPEA).

The compound of the present invention represented by the formula (I) wherein either $R^1$ or $R^2$ is a hydrogen atom can be prepared by condensing a tripeptide fragment of the following formula (IV)

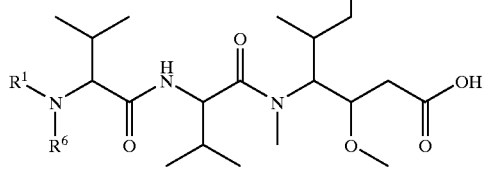

(IV)

wherein $R^1$ is hydrogen or alkyl, preferably ($C_1$–$C_6$)-alkyl, and most preferably ($C_1$–$C_4$)-alkyl; $R^6$ is a protecting group, e.g. selected from t-butoxycarbonyl (Boc), carbobenzyloxy (Z) or 9-fluorenylmethoxycarbonyl (Fmoc) group;

with a fragment of the following formula (III)

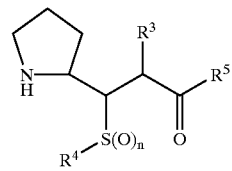

(III)

wherein $R^3$, $R^4$, $R^5$ and n are as defined above by using a condensing agent.

The condensing agent may be, e.g., dicyclohexylcarbodiimide (DCC), diphenyl phosphorylazide (DPPA), diethyl phosphorocyanide (DEPC), BOP reagent, or the like in an inert solvent such as, for example, halogenated aliphatic hydrocarbon such as chloroform and dichloromethane, ethylacetate, tetrahydrofuran (THF), dimethyl-formamide (DMF) or acetonitrile, if necessary in the presence of an organic base such as, for example, triethylamine or diisopropylethylamine (DIPEA) at a temperature between –10° to 50° C., preferably 0° C. to room temperature, and then the coupling product is deprotected by the procedures known to those in the art, e.g. by basic or acidic hydrolysis, hydrogenolysis or treatment with fluoride anion.

Compounds of formula (III) are novel and are also an object of this invention.

Another embodiment of the present invention concerns the preparation of compounds of formula (III).

Compounds of formula (III)

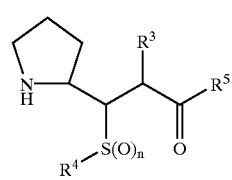

(III)

wherein $R^3$, $R^4$, $R^5$ and n are as defined above, can be prepared according to the following synthetic scheme 1.

scheme 1

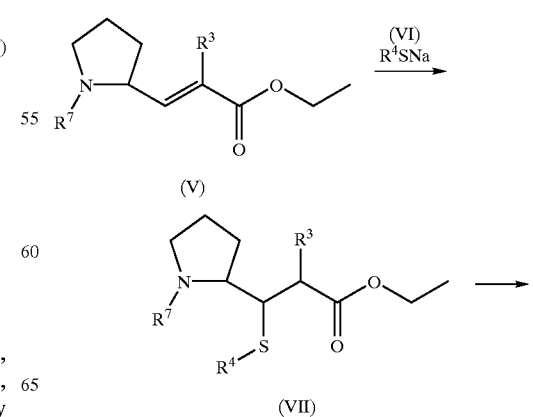

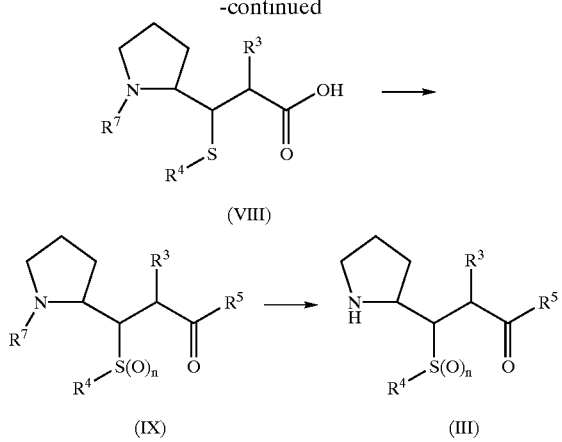

According to scheme 1, compounds of formula (III) are prepared from compound of formula (V), wherein $R^3$ is hydrogen or alkyl, preferably ($C_1$–$C_6$)-alkyl, and most preferably ($C_1$–$C_4$)-alkyl; $R^7$ is a protecting group selected from t-butoxycarbonyl, carbobenzyloxy or Fmoc group, prepared from N-Boc-prolinal by known methods (Heterocycles, 36 (9) 2073–2080, 1993), by reacting with a compound of formula (VI), a commercially available compound as the salt or prepared from the corresponding mercaptane with a base such as sodium hydroxide, sodium hydride, sodium carbonate, sodium hydrogen carbonate, potassium hydroxide, potassium hydride or potassium t-butoxide, lithium hydroxide, lithium hydride, methyl lithium or n-butyl lithium, by conventional methods, conveniently in an inert organic solvent, such as tetrahydrofuran, acetonitrile, methanol, ethanol or DMF, at a temperature from about −40° C. to the reflux temperature of the solvent to form a corresponding intermediate of formula (VII) wherein $R^3$ and $R^4$ are as defined in the present invention; $R^7$ is a protecting group selected from t-butoxycarbonyl, carbobenzyloxy or Fmoc group. Potassium thiomethoxide, in particular, can be alternatively prepared conveniently from the reaction of methyl thioacetate with potassium ethoxide in situ instead of using methylmercaptane gas.

The Michael addition of potassium thioalkoxide in the presence of a proton source such as an alcohol or phenol, preferably phenol, proceeds smoothly at room temperature, giving the desired stereoisomers regarding sulfur group and $R^3$ in good yield and stereoselectivity. For example, the reaction of the compound formula (V), where $R^3$ is methyl, $R^7$ is t-butoxycarbonyl group and the configuration of the proline 2-position is S, with potassium thiomethoxide or thioethoxide in the presence of phenol gives predominantly (2S)-2-[(1R,2S)-2-ethoxycarbonyl-1-methyl or ethyl-sulfanyl-propyl]-pyrrolidine-1-carboxylic acid tert-butyl ester.

The intermediate of formula (VII), wherein $R^3$, $R^4$ and $R^7$ are as defined above, is hydrolyzed, if necessary, by conventional methods and then reacted with an alcohol or an amine, conveniently using an aforementioned condensing agent in an inert organic solvent, such as a halogenated aliphatic hydrocarbon, tetrahydrofuran, acetonitrile, or DMF, at a temperature of from about −20° C. to the reflux temperature of the solvent, preferably from 0° C. to room temperature, to form a corresponding compound of formula (IX) wherein $R^3$, $R^4$ and $R^5$ are as defined in the present invention; $R^7$ is a protecting group selected from t-butoxycarbonyl, carbobenzyloxy or Fmoc group and n is an integer of 0.

The compound of formula (IX), wherein $R^3$, $R^4$ and $R^5$ are as defined above and n is 0; $R^7$ is a protecting group selected from t-butoxycarbonyl, carbobenzyloxy or Fmoc group, can be optionally oxidized with m-chloroperbenzoic acid (mCPBA) by conventional methods, conveniently in an inert organic solvent, such as a halogenated aliphatic hydrocarbon, at a temperature of from about −40° C. to the reflux temperature of the solvent to form a corresponding sulfoxide or sulfone derivative of formula (IX), wherein $R^3$, $R^4$ and $R^5$ are as defined in the present invention and n is an integer of 1 or 2; $R^7$ is a protecting group selected from t-butoxycarbonyl, carbobenzyloxy or Fmoc group.

The compound of formula (I), wherein $R^1$, $R^2$, $R^3$, $R^4$ and $R^5$ are as defined in above and n is 0, can be also optionally oxidized with mCPBA by conventional methods, conveniently in an inert organic solvent, such as a halogenated aliphatic hydrocarbon, at a temperature of from about −40° C. to the reflux temperature of the solvent to form a corresponding sulfoxide or sulfone derivative of formula (I) wherein $R^1$, $R^2$, $R^3$, $R^4$ and $R^5$ are as defined above ad n is 1 or 2.

Alternatively, the compound of formula (I), wherein $R^1$, $R^2$, $R^3$, $R^4$ and $R^5$ are as defined above, provided that either $R^1$ or $R^2$ is hydrogen, and n is 1 or 2, can be also prepared by oxidation of the coupling product obtained from (IV), wherein $R^1$ is alkyl group; $R^6$ is a protecting group selected from t-butoxycarbonyl, carbobenzyloxy or Fmoc group, and (III), wherein $R^3$, $R^4$ and $R^5$ are as defined above and n is 0, with mCPBA followed by deprotection known to those in the art, e.g. by basic or acidic hydrolysis, hydrogenolysis or treatment with fluoride.

The compound of formula (IX), wherein $R^3$, $R^4$, $R^5$, n are as defined above and $R^7$ is a protecting group selected from t-butoxycarbonyl, carbobenzyloxy or Fmoc group, is deprotected with trifluoroacetic acid (TFA) in an inert solvent such as a halogenated aliphatic hydrocarbon or without solvent at a temperature of from about −20° C. to the reflux temperature of the solvent, preferably from 0° C. to room temperature, to form a corresponding compound of formula (III) as the TFA salt.

EXAMPLES

The following Examples are provided to illustrate the invention and are not intended to limit it in any way. The compound data were recorded as a TFA salt of a mixture of diastereomers regarding the chiral center of the carbon atom having the sulfur atom (R:S=4:1 to 10:1) unless otherwise noted. The stereochemistry of the product was determined by NMR analysis of the bicyclic lactam formed after removing Boc group.

The retention time of each compound in HPLC was recorded using the following method unless otherwise noted.

column: Inertsil ODS-3/4.0×33 mm (GL Science Inc.)
mobile phase: 0.05% TFA-water: 0.05% TFA-acetonitrile,
flow rate: 1.0 ml/min
gradient: 10% MeCN at 0 min→95% MeCN at 4 min→95% MeCN at 5.5 min→10% MeCN at 6.0 min Reference Example 1

Preparation of 3-(N-tert-butoxycarbonyl-2'-pyrrolidinyl)-3-methylsulfanylpropanoic acid To a stirred solution of (S)-2-(2-ethoxycarbonyl-vinyl)-pyrrolidine-1-carboxylic acid tert-butyl ester (1 g, 3.71 mmol), prepared by a reported method (Heterocycles, 36 (9)

2073–2080, 1993), in THF (10 ml) was added NaSMe (95%: 781 mg, 11.1 mmol) at 0° C. The mixture was allowed to warm to room temperature and stirred for 16 hr. The mixture was quenched with 1N HCl, extracted with AcOEt, dried (MgSO$_4$) and concentrated in vacuo to give crude 3-(N-tert-butoxycarbonyl-2'-pyrrolidinyl)-3-methylsulfanylpropanoic acid (1.13 g), which was used without further purification in the next step.

Reference Example 2

Preparation of 3-(N-tert-butoxycarbonyl-2'-pyrrolidinyl)-3-methylsulfanyl-N-phenylethylpropanamide To a stirred solution of the crude 3-(N-tert-butoxycarbonyl-2'-pyrrolidinyl)-3-methylsulfanylpropanoic acid (1.13 g) obtained above and phenylethylamine (0.61 ml, 4.83 mmol) in CH$_2$Cl$_2$ (10 ml) were added WSCI monohydrochloride (682 mg, 4.46 mmol), HOBt monohydrate (682 mg, 4.46 mmol) and diisopropylethylamine (1.94 ml, 11.1 mmol) at room temperature. After being stirred at room temperature for 14 hr, the mixture was evaporated in vacuo, extracted with AcOEt, washed with 1N HCl and H$_2$O, dried (MgSO$_4$) and concentrated in vacuo. The residue (ca. 2.0 g) was purified by flash column chromatography (hexane:AcOEt=2:1) to give 3-(N-tert-butoxycarbonyl-2'-pyrrolidinyl)-3-methylsulfanyl-N-phenylethylpropanamide as an oil (1.15 g, 79%) which was the 5:1 (R:S) mixture of the two diastereomers at the newly formed chiral center determined by $^1$H-NMR.
$^1$H NMR (270 MHz, CDCl$_3$): δ1.45 (9H, s), 1.58–2.02(4H, m), 2.07(3H, s), 2.23–2.56(2H, m), 2.84(2H, t, J=6.9Hz), 3.19–3.30(1H, m), 3.30–3.69(4H, m), 3.82–4.00(4/5H, m), 4.03–4.14(1/4H, m), 6.32(1H, brs), 7.08–7.38(5H, m). LC-MS: 393 (MH$^+$), HPLC-RT: 3.90 min.

Reference Example 3

Preparation of 3-(N-tert-butoxycarbonyl-2'-pyrrolidinyl)-3-ethylsulfanyl-N-phenylethylpropanamide To a stirred solution of (S)-2-(2-ethoxycarbonyl-vinyl)-pyrrolidine-1-carboxylic acid tert-butyl ester (103 mg, 0.382 mmol) in THF (2 ml) was added EtSH (85 μl, 1.15 mmol) and NaH (60% in paraffin liquid: 46 mg, 1.15 mmol) at 0° C. The mixture was allowed to warm to room temperature and stirred for 7 hr. The mixture was quenched with 1N HCl, extracted with AcOEt, washed with saturated aqueous NaCl, dried (MgSO$_4$), and concentrated in vacuo to give 2-(2-ethoxycarbonyl-vinyl)-pyrrolidine-1-carboxylic acid tert-butyl ester (136 mg) as a crude oil, which was used without further purification in the next step.

To a stirred suspension of the crude 2-(2-ethoxycarbonyl-vinyl)-pyrrolidine-1-carboxylic acid tert-butyl ester (136 mg) in THF (1 ml) and H$_2$O (1 ml) was added LiOH.H$_2$O (48 mg, 1.14 mmol) at room temperature. The mixture was stirred at room temperature for 17 hr. The mixture was extracted with 1N NaOH and AcOEt. The aqueous layer was acidified with 1N HCl, extracted with AcOEt, washed with saturated aqueous NaCl, dried (MgSO$_4$), and concentrated in vacuo to give 2-(2-carboxy-vinyl)-pyrrolidine-1-carboxylic acid tert-butyl ester as a crude oil (109 mg). To a stirred solution of the crude oil (105 mg) in CH$_3$CN (2 ml) were added BOP reagent (306 mg, 0.692 mmol), phenethylamine (87 μl, 0.693 mmol), and diisopropylethylamine (121 μl, 0.695 mmol) at 0° C. The mixture was allowed to warm to room temperature and stirred for 12 hr. After being evaporated in vacuo, the mixture was dissolved in CH$_2$Cl$_2$. The solution was washed with 10% aqueous citric acid, saturated aqueous NaHCO$_3$, and saturated aqueous NaCl, dried (MgSO$_4$, and concentrated in vacuo. The residual oil was purified by preparative TLC (hexane:AcOEt=1:1) to give 3-(N-tert-butoxycarbonyl-2'-pyrrolidinyl)-3-ethylsulfanyl-N-phenylethylpropanamide (104 mg, 67% ) as an oil which was the 5:1 (R:S) mixture of the two diastereomers at the newly formed chiral center determined by $^1$H-NMR.
$^1$H NMR (270 MHz, CDCl$_3$): δ1.19 (3H, t, J=7.6 Hz), 1.45 (9H, s), 1.61–2.04 (4H, m), 2.07–2.43 (2H, m), 2.53 (2H, q, J=7.6 Hz), 2.84 (2H, t, J=6.9 Hz), 3.20–3.35 (1H, m), 3.36–3.79 (4H, m), 3.80–3.98 (5/6H, m), 3.98–4.10 (1/6H, m), 6.46 (1H, brs), 7.15–7.38 (5H,m). LC-MS: 407 (MH$^+$), HPLC-RT: 3.90 min.

Example 1

N-[1-({1-sec-Butyl-2-methoxy-4-[2-(1-methylsulfanyl-2-phenethylcarbamoyl-ethyl)-pyrrolidin-1-yl]-4-oxo-butyl}-methyl-carbamoyl)-2-methyl-propyl]-2-dimethylamino-3-methyl-butyramide To a stirred solution of 3-(N-tert-butoxycarbonyl-2'-pyrrolidinyl)-3-methylsulfanyl-N-phenylethylpropanamide (30.3 mg, 0.0772 mmol) in CH$_2$Cl$_2$ (0.5 ml) was added TFA (0.5 ml) at 0° C. The mixture was allowed to warm to room temperature and stirred for 4 hr. The mixture was evaporated in vacuo to give 3-methylsulfanyl-N-phenethyl-3-pyrrolidin-2-yl-propionamide TFA salt as a crude oil.

After the crude 3-methylsulfanyl-N-phenethyl-3-pyrrolidin-2-yl-propionamide TFA salt obtained above was dissolved in DMF(2 ml), the solution was added at 0° C. to (3R*,4S*,5S*)-4-[N,N-dimethyl-L-valyl-(N-methyl-L-valinamido)]-3-methoxy-5-methylheptanoic acid which was prepared from (3R*,4S*,5S*)-4-[N,N-dimethyl-L-valyl-(N-methyl-L-valinamido)]-3-methoxy-5-methylheptanoic acid t-Bu ester (34 mg, 0.0700 mmol) by treating with TFA in CH$_2$Cl$_2$ according to the literature method (Chem. Pharm. Bull., 43(10), 1706–1718, 1995). To the solution were added diethyl phosphorocyanidate (95%: 12 μl, 0.0751 mmol) and triethylamine (49 μl, 0.352 mmol) at 0° C. After being stirred at 0° C. for 1 hr, the mixture was allowed to warm to room temperature and stirred for 20 hr. The mixture was quenched with saturated aqueous NaHCO$_3$, extracted with AcOET, washed with saturated aqueous NaCl, dried (MgSO$_4$), and concentrated in vacuo to give the crude oil (90 mg), which was purified by preparative HPLC (column: ODS-80Ts, eluent: 39/31 H$_2$O:CH$_3$CN/0.05% TFA). The appropriate fractions were lyophilized to obtain the title compound as a white amorphous powder (30 mg, 47%).
$^1$H NMR (270 MHz, CDCl$_3$): δ0.65–1.09 (15H, m), 1.12 (3H, d, J=6.3 Hz), 1.30–2.65 (15H, m), 2.06 (3H, s), 2.83 (2H, t, J=7.6 Hz), 2.95 (6H, s), 3.00 (3H, s,), 3.30 (3H, s), 3.35–3.90 (4H, m), 3.95–4.12 (1H, m), 4.14–4.40 (1H, m), 4.60–4.85 (2H, m), 7.05–7.38 (5H, m). LC-MS: 704 (MH$^+$), HPLC-RT: 2.88 min.

The following compounds (Example 2–45) were obtained in a manner analogous to that of Example 1.

Example 2

N-[1-({1-sec-Butyl-4-[2-(1-(S)-tert-butylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide In a similar manner to Example 1, the title compound was obtained from the condensation reaction of (3R*,4S*,5S*)-

4-[N,N-dimethyl-L-valyl-(N-methyl-L-valinamido)]-3-methoxy-5-methylheptanoic acid and 3-tert-butylsulfanyl-N-phenethyl-3-pyrrolidin-2-yl-propionamide.

¹H NMR (270 MHz, CDCl₃):δ0.68–1.00 (15H, m), 1.07 (3H, d, J=6.6 Hz), 1.27 (9H, s), 1.45–2.45 (15H, m), 2.75 (2H, t, J=6.9 Hz), 2.88 (6H, s), 2.94 (3H, s,), 3.32–3.90 (4H, m), 3.92–4.08 (1H, m), 4.22–4.32 (1H, m), 4.50–4.79 (2H, m), 7.05–7.32 (5H, m). LC-MS: 746 (MH⁺), HPLC-RT: 3.20 min. (S-isomer).

Example 3

N-{1-[(1-sec-Butyl-4-{2-[1-(4-tert-butyl-phenylsulfanyl)-2-phenethylcarbamoyl-ethyl]-pyrrolidin-1-yl }-2-methoxy-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-(4-tert-butyl-phenylsulfanyl)-N-phenethyl-3-pyrrolidin-2-yl-propionamide.

¹H NMR (270 MHz, CDCl₃): δ0.70–1.08 (15H, m), 1.13 (3H, d, J=6.6 Hz), 1.28 (9H, s), 1.20–2.55 (15H, m), 2.79 (2H, t, J=7.3 Hz), 2.95 (6H, s), 2.99 (3H, s), 3.26 (3H, s), 3.30–3.82 (4H, m), 3.92–4.10 (1H, m), 4.25–4.38 (1H, m), 4.61–4.82 (2H, m), 7.08–7.33 (5H, m), LC-MS: 822 (MH⁺), HPLC-RT: 3.64 min. (R-isomer)

Example 4

N-{1-[(1-sec-Butyl-2-methoxy-4-{2-[1-(4-methoxy-phenylsulfanyl)-2-phenethylcarbamoyl-ethyl]-pyrrolidin-1-yl}-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-(4-methoxy-phenylsulfanyl)-N-phenethyl-3-pyrrolidin-2-yl-propionamide.

¹H NMR (270 MHz, CDCl₃): δ0.70–1.08 (15H, m), 1.13 (3H, d, J=6.6 Hz), 1.20–2.55 (15H, m), 2.79 (2H, t, J=7.3 Hz), 2.95 (6H, s), 2.99 (3H, s), 3.27 (3H, s), 3.30–3.90 (4H, m), 3.77 (3H, s), 3.90–4.18 (1H, m), 4.20–4.35 (1H, m), 4.60–4.85 (2H, m), 6.79 (2H, d J=8.9 Hz), 7.32 (2H, d, J=8.5Hz), 7.10–7.40 (5H, m). LC-MS: 796 (MH⁺), HPLC-RT: 3.14 min. (R-isomer)

Example 5

N-{1-[(1-sec-Butyl-4-{2-[1-(S)-(4-hydroxy-phenylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-(4-hydroxy-phenylsulfanyl)-N-phenethyl-3-pyrrolidin-2-yl-propionamide.

¹H NMR (270 MHz, CDCl₃): δ0.65–1.18 (18H, m), 1.20–1.40 (2H, m), 1.50–2.90 (15H, m), 2.95 (6H, s), 3.01 (3H, s), 3.25(1H, s), 3.32 (2H, s), 3.35–4.10 (5H, m), 4.12–4.30 (1H,m), 4.50–4.78 (2H, m), 6.75(2/3H, d, J=8.6 Hz), 6.82 (4/3H, d, J=8.6 Hz), 7.08–7.35 (7H,m). LC-MS: 782 (MH⁺), HPLC-RT: 2.87 min. (S-isomer)

Example 6

N-{1-[(1-sec-Butyl-4-{2-[1-(R)-(4-hydroxy-phenylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-(4-hydroxy-phenylsulfanyl)-N-phenethyl-3-pyrrolidin-2-yl-propionamide.

¹H NMR (270 MHz, CDCl₃): δ0.68–1.20 (18H, m), 1.21–1.40 (2H, m), 1.50–2.90 (15H, m), 2.96 (6H, s), 3.03 (3H, s), 3.26 (3H, s), 3.32–3.70 (4H, m), 3.72–4.00 (1H,m), 4.15–4.35 (1H, m), 4.68–4.78 (2H, m), 6.75 (2H, d, J=8.6 Hz), 7.08–7.35 (7H, m). LC-MS: 7.82 (MH⁺), HPLC-RT: 2.88 min. (R-isomer)

Example 7

N-{1-[(4-{2-[1-(4-Acetylamino-phenylsulfanyl)-2-phenethylcarbamoyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-(4-Acetylamino-phenylsulfanyl)-N-phenethyl-3-pyrrolidin-2-yl-propionamide.

¹H NMR (270 MHz, CDCl₃): δ0.70–1.20 (18H, m), 1.21–2.95 (15H, m), 2.16 (3H, s), 2.79 (2H, t, J=7.3 Hz), 2.96 (6H, s), 3.00 (3H, s), 3.25 (3H, s), 3.30–4.08 (5H, m), 4.20–4.35 (1H, m), 4.50–4.80 (2H, m), 7.08–7.40 (7H, m), 7.43 (2H, d, J=8.2 Hz). LC-MS: 823 (MH⁺), HPLC-RT: 2.82 min. (R-isomer)

Example 8

N-{1-[(1-sec-Butyl-4-{2-[1-(4-fluoro-phenylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-(4-fluoro-phenylsulfanyl)-N-phenethyl-3-pyrrolidin-2-yl-propionamide.

¹H NMR (270 MHz, CDCl₃): δ0.67–1.09 (15H, m), 1.13 (3H, d, J=6.6 Hz), 1.20–1.40 (2H, m), 1.42–2.62 (13H, m), 2.80 (2H, t, J=6.9 Hz), 2.96 (6H, s), 2.98 (3H,s), 3.26 (3H, s), 3.27–4.08 (5H, m), 4.20–4.35 (1H, m), 4.60–4.80 (2H, m), 6.95 (2H, t, J=8.6 Hz), 7.08–7.30 (5H, m), 7.36 (2H, dd, J=5.3, 8.9 Hz). LC-MS: 784 (MH⁺), HPLC-RT: 3.17 min. (R-isomer)

Example 9

N-[1-({1-sec-Butyl-4-[2-(1-(R)-tert-butylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide In a similar manner to Example 1, the title compound was obtained from the condensation reaction of (3R*,4S*,5S*)-

4-[N,N-dimethyl-L-valyl-(N-methyl-L-valinamido)]-3-methoxy-5-methylheptanoic acid and 3-tert-butylsulfanyl-N-phenethyl-3-pyrrolidin-2-yl-propionamide.
¹H NMR (270 MHz, CDCl₃): δ0.65–1.00 (15H, m), 1.06 (3H, d, J=6.4 Hz), 1.17 (9H, s), 1.35–2.55 (15H, m), 2.79 (2H, t, J=6.9 Hz), 2.88 (6H, s), 2.94 (3H, s), 3.21 (3H,s), 3.22–3.82 (4H, m), 3.92–4.05 (2H, m), 4.55–4.80 (2H, m), 6.95–7.30 (5H, m). LC-MS: 746 (MH⁺), HPLC-RT: 3.16 min. (R-isomer)

Example 10

N-{1-[(1-sec-Butyl-4-{2-[1-(2-hydroxy-ethylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-(2-hydroxy-ethylsulfanyl)-N-phenethyl-3-pyrrolidin-2-yl-propionamide.
¹H NMR (270 MHz, CDCl₃): δ0.57–1.21(18H, m), 1.20–1.55(2H, m), 1.55–2.30(10H, m), 2.30–2.77(5H, m), 2.73(2H, t, J=6.59 Hz), 2.96(6H, s), 3.05(3H, s), 3.35(3H, s), 3.40–3.92(6H, m), 3.95–4.46(2H, m), 4.56–4.90(2H, m), 6.55(1H, brs), 7.08–7.39(5H, m), 7.92(1H, brs). LC-MS: 734 (MH⁺), HPLC-RT: 2.70 min.

Example 11

Acetic acid 2-{1-[1-(4-{[2-(2-dimethylamino-3-methyl-butyrylamino)-3-methyl-butyryl]-methyl-amino}-3-methoxy-5-methyl-heptanoyl)-pyrrolidin-2-yl]-2-phenethylcarbamoyl-ethylsulfanyl}-ethyl ester In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and acetic acid 2-(2-phenethylcarbamoyl-1-pyrrolidin-2-yl-ethylsulfanyl)-ethyl ester.
¹H NMR (270 MHz, CDCl₃): δ0.57–1.20(18H, m), 1.20–1.45 (2H, m), 1.55–2.31(10H, m), 2.02(3H, s), 2.30–2.67(3H, m), 2.73(2H, t, J=6.11 Hz), 2.83(2H, t, J=6.93 Hz), 2.96(6H, s), 3.03(3H, s), 3.31(3H, s), 3.40–3.95(4H, m), 3.95–4.40(4H, m), 4.52–4.88(2H, m), 6.45(1H, brs), 7.08–7.39(5H, m), 7.79(1H, brs). LC-MS: 776 (MH⁺), HPLC-RT: 2.86 min.

Example 12

3-[1-(4-{[2-(2-Dimethylamino-3-methyl-butyrylamino)-3-methyl-butyryl]-methyl-amino}-3-methoxy-5-methyl-heptanoyl)-pyrrolidin-2-yl]-3-methylsulfanyl-propionic acid tert-butyl ester In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-methylsulfanyl-3-pyrrolidin-2-yl-propionic acid tert-butyl ester.
¹H NMR (270 MHz, CDCl₃): δ0.68–1.20(18H, m), 1.20–1.42 (2H, m), 1.45(9H, s), 1.55–2.29(10H, m), 2.10 (3H, s), 2.30–2.58(3H, m), 2.96(6H, s), 3.01(3H, s), 3.33(3H, s), 3.40–3.90(2H, m), 4.01–4.39(2H, m), 4.59–4.89(2H, m), 7.50(1H, brs). LC-MS: 657 (MH⁺), HPLC-RT:3.10 min.

Example 13

3-[1-(4-{[2-(2-Dimethylamino-3-methyl-butyrylamino)-3-methyl-butyryl]-methyl-amino}-3-methoxy-5-methyl-heptanoyl)-pyrrolidin-2-yl]-3-methylsulfanyl-propionic acid In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-methylsulfanyl-3-pyrrolidin-2-yl-propionic acid.
¹H NMR (270 MHz, DMSO-d6): δ0.76(3H, m), 0.81–1.07 (15H, m), 1.12–1.40 (2H, m), 1.55–2.18(10H, m), 2.01 (3H, s), 2.20–2.66(3H, m), 2.67–2.84(6H, m), 3.01 (3H, s), 3.20(3H, s), 3.24–3.80(2H, m), 3.80–4.37(2H, m), 4.49–4.79(2H, m), 8.93(1H, d, J=7.92 Hz), 9.50(1H, brs). LC-MS: 601 (MH⁺), HPLC-RT: 2.51 min.

Example 14

N-(1-{[1-sec-Butyl-2-methoxy-4-(2-{1-methylsulfanyl-2-[2-(4-sulfamoyl-phenyl)-ethylcarbamoyl]-ethyl}-pyrrolidin-1-yl)-4-oxo-butyl]-methyl-carbamoyl}-2-methyl-propyl)-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-methylsulfanyl-3-pyrrolidin-2-yl-N-[2-(4-sulfamoyl-phenyl)-ethyl]-propionamide.
¹H NMR (270 MHz, CDCl₃): δ0.81(3H, t, J=6.59 Hz), 0.85–1.19(15H, m), 1.20–1.42 (2H, m), 1.62–2.30(10H, m), 2.04(3H, s), 2.30–2.63(3H, m), 2.78–2.99(2H, m), 2.99(6H, s), 3.06(3H, s), 3.12(3H, s), 3.23–3.79(4H, m), 3.80–4.25(4H, m), 4.53–4.81(2H, m), 7.12(1H, brs), 7.32 (2H, d, J=7.92 Hz), 7.79(2H, d, J=7.92 Hz), 7.65–7.82 (3H, m). LC-MS: 783 (MH⁺), HPLC-RT: 2.42 min.

Example 15

N-(1-{[1-sec-Butyl-4-(2-{2-[2-(4-hydroxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and N-[2-(4-hydroxy-phenyl)-ethyl]-3-methylsulfanyl-3-pyrrolidin-2-yl-propionamide.
¹H NMR (270 MHz, CDCl₃): δ0.81(3H, t, J=6.92 Hz), 0.89–1.19(15H, m), 1.20–1.42 (2H, m), 1.59–2.33(10H, m), 2.03(3H, s), 2.30–2.60(3H, m), 2.60–2.82(2H, m), 2.98(6H, s), 3.07(3H, s), 3.23(3H, s), 3.30–3.70(4H, m), 3.70–4.32(4H, m), 4.57–4.81(2H, m), 6.75(2H, d, J=8.57 Hz), 7.00(1H, brs), 7.01(2H, d, J=8.57 Hz), 7.30–8.60 (2H, m). LC-MS: 720 (MH⁺), HPLC-RT: 2.50 min.

Example 16

N-{1-[(1-sec-Butyl-2-methoxy-4-{2-[2-(methyl-phenethyl-carbamoyl)-1-methylsulfanyl-ethyl]-pyrrolidin-1-yl}-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-

4-[N,N-dimethyl-L-valyl-(N-methyl-L-valinamido)]-3-methoxy-5-methylheptanoic acid and N-methyl-3-methylsulfanyl-N-phenethyl-3-pyrrolidin-2-yl-propionamide.
$^1$H NMR (270 MHz, CDCl$_3$): δ0.51–1.19(18H, m), 1.20–1.40 (2H, m), 1.55–2.30(10H, m), 2.01(3H, s), 2.30–2.71(3H, m), 2.71–3.10(14H, m), 3.10–3.88(4H, m), 3.31(3H, s), 3.95–4.40(2H, m), 4.47–4.91(2H, m), 6.99–7.38(5H, m), 7.56(1H, brs). LC-MS: 718 (MH$^+$), HPLC-RT: 2.92 min.

Example 17

N-{1-[(4-{2-[3-(4-Benzhydryl-piperazin-1-yl)-1-methylsulfanyl-3-oxo-propyl]-pyrrolidin-1-yl}-1-sec-butyl-2-methoxy-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 1-(4-benzhydryl-piperazin-1-yl)-3-methylsulfanyl-3-pyrrolidin-2-yl-propane-1-one.
$^1$H NMR (270 MHz, CDCl$_3$): δ0.51–1.19(18H, m), 1.20–1.41 (2H, m), 1.55–2.20(10H, m), 1.99(3H, s), 2.20–2.75(3H, m), 2.75–4.55 (12H, m), 3.02(6H, s), 3.16 (3H, s), 3.34(3H, s), 4.55–5.02(2H, m), 5.09–5.26(1H, m), 7.30–7.48(6H, m), 7.50–7.77(4H, m). LC-MS: 8.35 (MH$^+$), HPLC-RT: 2.57 min.

Example 18

N-(1-{[1-sec-Butyl-4-(2-{2-[2-(2-hydroxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and N-[2-(2-hydroxy-phenyl)-ethyl]-3-methylsulfanyl-3-pyrrolidin-2-yl-propionamide.
$^1$H NMR (270 MHz, CDCl$_3$): δ0.82(3H, t, J=6.59 Hz), 0.87–1.20(15H, m), 1.20–1.42 (2H, m), 1.59–2.34(10H, m), 2.00(3H, s), 2.34–2.65(3H, m), 2.65(2H, t, J=6.60 Hz), 2.97(6H, s), 3.07(3H, s), 3.32(3H, s), 3.37–3.91(4H, m), 3.91–4.35(2H, m), 4.57–4.88(2H, m), 6.10–8.15(3H, m), 6.55–7.17(4H, m). LC-MS: 720 (MH$^+$), HPLC-RT: 2.67 min.

Example 19

N-(1-{[1-sec-Butyl-4-(2-{2-[2-(3-hydroxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and N-[2-(3-hydroxy-phenyl)-ethyl]-3-methylsulfanyl-3-pyrrolidin-2-yl-propionamide.
$^1$H NMR (270 MHz, CDCl$_3$): δ0.81(3H, t, J=6.59 Hz), 0.87–1.20(15H, m), 1.20–1.40 (2H, m), 1.65–2.31(10H, m), 2.04(3H, s), 2.31–2.68(3H, m), 2.78(2H, t, J=6.60 Hz), 2.96(6H, s), 3.09(3H, s), 3.33(3H, s), 3.41–3.79(4H, m), 3.79–4.28(2H, m), 4.35–4.88(2H, m), 6.50–7.21(4H, m), 7.78(1H, brs). LC-MS: 720 (MH$^+$), HPLC-RT: 2.58 min.

Example 20

N-{1-[(4-{2-[2-(Benzyl-phenethyl-carbamoyl)-1-methylsulfanyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and N-benzyl-3-methylsulfanyl-N-phenethyl-3-pyrrolidin-2-yl-propionamide.
$^1$H NMR (270 MHz, CDCl$_3$): δ0.81(3H, t, J=6.93 Hz), 0.87–1.17(15H, m), 1.17–1.40 (2H, m), 150–2.31(10H, m), 2.08(3H, s), 2.31–2.76(3H, m), 2.75–2.89(2H, m), 2.98(6H, s), 3.06(3H, s), 3.32(3H, s), 3.38–4.09(5H, m), 4.13–4.56(3H, m), 4.56–4.82(2H, m), 6.85–7.41(4H, m), 7.81(1H, brs). LC-MS: 794 (MH$^+$), HPLC-RT: 3.43 min.

Example 21

N-{1-[(1-sec-Butyl-2-methoxy-4-{2-[1-methylsulfanyl-2-(2-phenyl-cyclopropylcarmoyl)-ethyl]-pyrrolidin-1-yl}-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-methylsulfanyl-N-(2-phenyl-cyclopropyl)-3-pyrrolidin-2-yl-propionamide.
$^1$H NMR (270 MHz, CDCl$_3$): δ0.50–1.18(18H, m), 1.18–1.45 (2H, m), 155–2.31(10H, m), 2.11(3H, s), 2.31–2.72(3H, m), 2.72–2.95(1H, m), 2.97(6H, s), 3.03 (3H, s), 3.32(3H, s), 3.35–4.09(4H, m), 4.10–4.43(1H, m), 4.50–4.83(2H, m), 6.88–7.40(4H, m), 7.68(1H, brs). LC-MS: 716 (MH$^+$), HPLC-RT: 2.90 min.

Example 22

N-{1-[(1-sec-Butyl-4-{2-[2-(4-tert-butyl-benzylcarbamoyl)-1-methylsulfanyl-ethyl]-pyrrolidin-1-yl}-2-methoxy-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and N-(4-tert-butyl-benzyl)-3-methylsulfanyl-3-pyrrolidin-2-yl-propionamide.
$^1$H NMR (270 MHz, CDCl$_3$): δ0.50–1.20(18H, m), 1.20–2.24 (12H, m), 1.30(9H, s), 2.09(3H, s), 2.25–2.71 (3H, m), 2.95(6H, s), 3.01(3H, s), 3.31(3H, s), 3.33–4.18 (3H, m), 4.19–4.60(3H, m), 4.64–4.83(2H, m), 6.63(1H, brs), 7.23(2H, d, J=8.25 Hz), 7.34(2H, d, J=8.25 Hz), 7.56(1H, brs). LC-MS: 746 (MH$^+$), HPLC-RT: 3.41 min.

Example 23

N-[1-({4-[2-(2-Benzylcarbamoyl-1-methylsulfanyl-ethyl)-pyrrolidin-1-yl]-1-sec-butyl-2-methoxy-4-oxo-butyl}-methyl-carbamoyl)-2-methyl-propyl]-2-dimethylamino-3-methyl-butyramide In a similar manner to Example 1, the title compound was obtained from the condensation reaction of (3R*,4S*,5s*)-

4-[N,N-dimethyl-L-valyl-(N-methyl-L-valinamido)]-3-methoxy-5-methylheptanoic acid and N-benzyl-3-methylsulfanyl-3-pyrrolidin-2-yl-propionamide.

$^1$H NMR (270 MHz, CDCl$_3$): δ0.50–1.20(18H, m), 1.20–1.39 (2H, m), 1.45–2.31(10H, m), 2.08(3H, s), 2.31–2.68(3H, m), 2.96(6H, s), 3.02(3H, s), 3.30(3H, s), 3.33–4.12(3H, m), 4.18–4.62(3H, m), 4.62–4.83(2H, m), 6.79(1H, brs), 7.02–7.39(5H, m), 7.52(1H, brs). LC-MS: 690 (MH$^+$), HPLC-RT: 2.76 min.

Example 24

N-{1-[(4-{2-[2-(N'-Benzyl-hydrazinocarbonyl)-1-methylsulfanyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-methylsulfanyl-3-pyrrolidin-2-yl-propionic acid N'-benzyl-hydrazide.

$^1$H NMR (270 MHz, CD$_3$OD): δ0.76(3H, t, J=7.02 Hz), 0.82–1.10(15H, m), 1.15–1.42 (2H, m), 1.55–2.18(10H, m), 1.98(3H, s), 2.18–2.59(3H, m), 2.80(6H, s), 3.05(3H, s), 3.22(3H, s), 3.34–3.73(3H, m), 3.80–4.38(2H, m), 4.51–4.78(2H, m), 7.25–7.47(5H, m). LC-MS: 7.05 (MH$^+$), HPLC-RT: 2.52 min.

Example 25

N-[1-({1-sec-Butyl-2-methoxy-4-oxo-4-[2-(2-phenethylcarbamoyl-1-phenethylsulfanyl-ethyl)-pyrrolidin-1-yl]-butyl}-methyl-carbamoyl)-2-methyl-propyl]-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and N-phenethyl-3-phenethylsulfanyl-3-pyrrolidin-2-yl-propionamide.

$^1$H NMR (270 MHz, CDCl$_3$): δ0.80–1.10 (18H, m), 1.19–1.35 (2H, m), 1.79–2.50 (14H, m), 2.72–2.82 (4H, m), 2.95 (6H, s), 3.01 (3H, s), 3.22 (3H, s), 3.26–3.36 (4H, m), 3.70–3.82 (1H, m), 4.03 (1H, brs), 4.20 (1H, brs), 4.73 (2H, brs), 6.41 (1H, brs), 7.14–7.30 (10H, m), 7.66 (1H, brs). LC-MS: 794 (MH$^+$), HPLC-RT: 3.25 min.

Example 26

N-[1-({4-[2-(1-Allylsulfanyl-2-phenethylcarbamoyl-ethyl)-pyrrolidin-1-yl]-1-sec-butyl-2-methoxy-4-oxo-butyl}-methyl-carbamoyl)-2-methyl-propyl]-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-allylsulfanyl-N-phenethyl-3-pyrrolidin-2-yl-propionamide.

$^1$H NMR (270 MHz, CDCl$_3$): δ0.79–1.15 (18H, m), 1.22–1.34 (2H, m), 1.66–2.53 (14H, m), 2.83 (2H, t, J=7.9 Hz), 2.95 (6H, s), 3.01 (3H, s), 3.30 (3H, s), 3.35–3.82 (5H, m), 4.06–4.20 (2H, m), 4.73 (2H, t, J=7.4 Hz), 5.03 (1H, d, J=9.6 Hz), 5.10 (1H, d, J=16.8 Hz) 5.62–5.80 (1H, m), 6.58 (1H, br s), 7.19–7.31 (5H, m), 7.60 (1H, brs). LC-MS: 730 (MH$^+$), HPLC-RT: 2.96 min.

Example 27

N-{1-[(1-sec-Butyl-2-methoxy-4-{2-[1-methylsulfanyl-2-(2-pyridin-4-yl-ethylcarbamoyl)-ethyl]-pyrrolidin-1-yl}-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-methylsulfanyl-N-(2-pyridin-4-yl-ethyl)-3-pyrrolidin-2-yl-propionamide.

$^1$H NMR (270 MHz, CDCl$_3$): δ0.82–1.10 (18H, m), 1.23–1.48 (2H, m), 1.86–2.25 (5H, m), 2.05 (3H, s), 2.91–3.0 (2H, m), 2.97 (6H, s), 3.06 (3H, s), 3.30 (3H, s), 3.10–4.07 (7H, m), 4.73 (2H, brs), 7.79 (2H, brs), 8.75 (2H, brs). LC-MS: 705 (MH$^+$), HPLC-RT: 2.01 min.

Example 28

N-(1-{[4-(2-{2-[(Benzothiazol-2-ylmethyl)-carbamoyl]-1-methylsulfanyl-ethyl}-pyrrolidin-1-yl)-1-sec-butyl-2-methoxy-4-oxo-butyl]-methyl-carbamoyl}-2-methyl-propyl)-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and N-benzothiazol-2-ylmethyl-3-methylsulfanyl-3-pyrrolidin-2-yl-propionamide.

$^1$H NMR (270 MHz, CDCl$_3$): δ0.74–1.14 (18H, m), 1.20–1.38 (2H, m), 1.80–2.20 (7H, m), 2.13 (3H, s), 2.32–2.75 (5H, m), 2.94 (6H, brs), 3.33 (3H, s), 3.22–3.38 (2H, m), 3.65–6.79 (1H, m), 3.90–4.11 (1H, m), 4.36 (1H, brs), 4.78–4.92 (4H, m), 7.34–7.51 (2H, m), 7.82–8.00 (2H, m). LC-MS: 747 (MH$^+$), HPLC-RT: 2.73 min.

Example 29

N-{1-[(1-sec-Butyl-2-methoxy-4-{2-[1-methylsulfanyl-2-(2-thiophen-2-yl-ethylcarbamoyl)-ethyl]-pyrrolidin-1-yl}-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-methylsulfanyl-3-pyrrolidin-2-yl-N-(2-thiophen-2-yl-ethyl)-propionamide.

$^1$H NMR (270 MHz, CDCl$_3$): δ0.79–1.13 (18H, m), 1.20–1.33 (2H, m), 1.85–2.58 (14H, m), 2.07 (3H, s), 2.97 (6H, brs), 3.03 (3H, s), 3.31 (3H, s), 3.36–3.69 (4H, m), 4.18–4.32 (1H, m), 4.66–4.80 (2H, m), 6.68 (1H, brs), 6.83–6.88 (1H, in), 6.91–6.94 (1H, m), 7.13–7.15 (1H, m), 7.56 (1H, brs). LC-MS: 710 (MH$^+$), HPLC-RT: 2.74 min.

Example 30

N-{1-[(1-sec-Butyl-2-methoxy-4-{2-[1-methylsulfanyl-2-(2-pyridin-3-yl-ethylcarbamoyl)-ethyl]-pyrrolidin-1-yl}-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-

4-[N,N-dimethyl-L-valyl-(N-methyl-L-valinamido)]-3-methoxy-5-methylheptanoic acid and 3-methylsulfanyl-N-(2-pyridin-3-yl-ethyl)-3-pyrrolidin-2-yl-propionamide.
$^1$H NMR (270 MHz, CDCl$_3$): δ0.82–1.11 (18H, m), 1.20–1.40 (2H, m), 1.85–2.56 (12H, m), 2.04 (3H, s), 2.98 (6H, s), 2.89–3.02 (2H, m), 3.08 (3H, s), 3.32 (3H, s), 3.40–3.55 (4H, m), 3.80–4.50 (3H, m), 4.66–4.80 (2H, m), 7.67–7.88 (2H, brs), 8.26–8.38 (1H, m), 8.67 (1H, brs). LC-MS: 705 (MH$^+$), HPLC-RT: 1.99 min.

Example 31

N-{1-[(1-sec-Butyl-2-methoxy-4-{2-[1-methylsulfanyl-2-(2-pyridin-2-yl-ethylcarbamoyl)-ethyl]-pyrrolidin-1-yl}-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-methylsulfanyl-N-(2-pyridin-2-yl-ethyl)-3-pyrrolidin-2-yl-propionamide.
$^1$H NMR (270 MHz, CDCl$_3$): δ0.81–1.09 (18H, m), 1.20–1.50 (2H, m), 1.70–2.70 (12H, m), 1.97 (3H, s), 2.85–3.12 (2Hm), 3.00 (6H, s), 3.07 (3H, s), 3.29 (3H, s), 3.36–3.86 (6H, m), 4.21 (1H, brs), 4.71 (2H, brs), 7.76 (1H, brs), 7.89 (1H, brs), 8.03 (1H, brs), 8.34 (1H, brs), 8.68 (1H, brs). LC-MS: 705 (MH$^+$), HPLC-RT: 2.00 min.

Example 32

N-(1-{[1-sec-Butyl-2-methoxy-4-(2-{1-methylsulfanyl-2-[(pyridin-4-ylmethyl)-carbamoyl]-ethyl}-pyrrolidin-1-yl)-4-oxo-butyl]-methyl-carbamoyl}-2-methyl-propyl)-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-methylsulfanyl-N-pyridin-4-ylmethyl-3-pyrrolidin-2-yl-propionamide.
$^1$H NMR (270 MHz, CDCl$_3$): δ0.82–1.40 (20H, m), 1.73–2.27 (7H, m), 2.12 (3H, s), 2.35–2.70 (5H, m), 2.96 (6H, brs), 3.08 (3H, s), 3.33 (3H, s), 3.42–4.06 (6H, m), 4.30 (1H, brs), 4.42–4.57 (1H, m), 4.62–4.88 (3H, m), 7.88 (2H, brs), 8.80 (2H, brs). LC-MS: 691 (MH$^+$), HPLC-RT: 2.00 min.

Example 33

N-(1-{[1-sec-Butyl-4-(2-{2-[2-(3H-imidazol-4-yl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and N-[2-(3H-imidazol-4-yl)-ethyl]-3-methylsulfanyl-3-pyrrolidin-2-yl-propionamide.
$^1$H NMR (270 MHz, DMSO-d6): δ0.74–1.01 (18H, m), 1.25–1.28 (2H, m), 1.63–1.88 (7H, m), 1.95 (3H, s), 1.95–2.33 (7H, mn), 2.77 (6H, s), 3.01 (3H, s), 3.21 (3H, s), 3.23–4.12 (7H, m), 4.50–4.71 (2H, m), 7.42 (1H, brs), 8.06 (1H, brs), 8.92–8.99 (1H, m), 9.70 (1H, brs), 14.36 (1H, br s). LC-MS: 694 (MH$^+$), HPLC-RT: 2.06min.

Example 34

N-{1-[(1-sec-Butyl-2-methoxy-4-{2-[1-methylsulfanyl-2-(thiazol-2-ylcarbamoyl)-ethyl]-pyrrolidin-1-yl}-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-methylsulfanyl-3-pyrrolidin-2-yl-N-thiazol-2-yl-propionamide.
$^1$H NMR (270 MHz, CDCl$_3$): δ0.79–1.12 (18H, m), 1.20–1.50 (2H, m), 1.60–2.50 (12H, m), 2.14 (3H, s), 2.97 (6H, brs), 3.11 (3H, s), 3.31 (3H, s), 3.40–3.80 (3H, m), 4.01 (1H, brs), 4.38 (1H, brs), 4.67–4.78 (2H, m), 7.07 (1H, brs), 7.48 (1H, brs), 7.65 (1H,brs), 8.62 (1H, brs). LC-MS: 683 (MH$^+$), HPLC-RT: 2.67 min.

Example 35

N-{1-[(1-sec-Butyl-2-methoxy-4-{2-[1-methylsulfanyl-2-(naphthalen-2-ylcarbamoyl)-ethyl]-pyrrolidin-1-yl}-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-methylsulfanyl-N-naphthalen-2-yl-3-pyrrolidin-2-yl-propionamide.
$^1$H NMR (270 MHz, CDCl$_3$): δ0.52–1.50 (20H, m), 1.95–2.43 (12H, m), 2.17 (3H, s), 2.78 (3H, s), 2.95 (3H, s), 3.27 (3H, s), 3.45–4.08 (4H, m), 4.42 (1H, br s), 4.72 (2H, brs), 7.41–7.75 (7H, m), 8.33 (1H, brs), 8.93 (1H, brs). LC-MS: 726 (MH$^+$), HPLC-RT: 3.13 min.

Example 36

N-[-({1-sec-Butyl-4-[2-(2-cyclohexylcarbamoyl-1-methylsulfanyl-ethyl)-pyrrolidin-1-yl]-2-methoxy-4-oxo-butyl}-methyl-carbamoyl)-2-methyl-propyl]-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and N-cyclohexyl-3-methylsulfanyl-3-pyrrolidin-2-yl-propionamide.
$^1$H NMR (270 MHz, CDCl$_3$): δ0.82–1.33 (20H, m), 1.60–2.00 (15H, m), 2.10 (3H, s), 2.40–2.60 (5H, m), 2.99 (6H, s), 3.07 (3H, s), 3.32 (3H, s), 3.50–3.98 (7H, m), 4.29 (1H, brs), 4.73 (2H, brs), 6.08 (1H, brs), 7.77 (1H, brs). LC-MS: 682 (MH$^+$), HPLC-RT: 2.85 min.

Example 37

N-[1-({1-sec-Butyl-4-[2-(2-{[2-(3,4-dimethoxy-phenyl)-ethyl]-methyl-carbamoyl}-1-methylsulfanyl-ethyl)-pyrrolidin-1-yl]-2-methoxy-4-oxo-butyl}-methyl-carbamoyl)-2-methyl-propyl]-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and N-[2-(3,4-dimethoxy-phenyl)-ethyl]-N-methyl-3-methylsulfanyl-3-pyrrolidin-2-yl-propionamide.

¹H NMR (270 MHz, CDCl₃): δ0.81–1.11 (18H, m), 1.20–1.40 (2H, m), 1.65–1.94 (7H, m), 2.10 (3H, s), 2.02–2.51 (5H, m), 2.81 (2H, brs), 2.98 (9H, brs), 3.07 (3H, s), 3.31 (3H, s), 3.40–4.00 (6H, m), 3.87, 3.85 (6H, 2s), 4.31 (1H, m), 4.73 (2H, br s), 6.03–6.67 (3H, m,), 7.71 (1H, brs). LC-MS: 778 (MH⁺), HPLC-RT: 2.80 min.

Example 38

N-(1-{[1-sec-Butyl-4-(2-{2-[2-(3,4-dimethoxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and N-[2-(3,4-dimethoxy-phenyl)-ethyl]-3-methyl sulfanyl-3-pyrrolidin-2-yl-propionamide.

¹H NMR (270 MHz, CDCl₃): δ0.78–1.15 (18H, m), 1.20–1.40 (2H, m), 1.62–2.48 (12H, m), 2.06 (3H, s), 2.78 (2H, t, J=7.6 Hz), 2.96 (6H, s), 3.01 (3H, s,), 3.35–3.76 (5H, m), 3.86 (6H, s), 3.92–4.10 (1H, m), 4.15–4.30 (1H, m), 4.68–4.80 (1H, brs), 6.40 (1H, brs), 6.72–6.81 (3H, m), 7.42 (1H, brs). LC-MS: 764 (MH⁺), HPLC-RT: 2.69 min.

Example 39

N-[1-({1-sec-Butyl-2-methoxy-4-oxo-4-[2-(1-pentylsulfanyl-2-phenethylcarbamoyl-ethyl)-pyrrolidin-1-yl]-butyl}-methyl-carbamoyl)-2-methyl-propyl]-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-pentylsulfanyl-N-phenethyl-3-pyrrolidin-2-yl-propionamide.

¹H NMR (270 MHz, CDCl₃): δ0.81–1.62 (27H, m), 1.72–2.40 (12H, m), 2.44–2.59 (5H, m), 2.73–2.90 (2H, m), 2.95 (6H, s), 3.02 (3H, s), 3.30 (3H, s), 3.30–3.86 (4H, m), 4.01–4.20 (2H, m), 4.73 (2H, brs), 7.18–7.28 (5H, m). LC-MS: 760 (M⁺), HPLC-RT: 3.71 min (Waters).

Example 40

N-{1-[(1-sec-Butyl-2-methoxy-4-{2-[1-(naphthalen-2-ylsulfanyl)-2-phenethylcarbamoyl-ethyl]-pyrrolidin-1-yl}-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-(naphthalen-2-ylsulfanyl)-N-phenethyl-3-pyrrolidin-2-yl-propionamide.

¹H NMR (270 MHz, CDCl₃): δ0.70–1.20 (18H, m), 1.40–2.60 (15H, m), 2.77 (2H, t, J=5.0 Hz), 2.94 (6H, s), 2.96 (3H, s), 3.35 (3H, s), 3.50–3.80 (4H, m), 4.30–4.40 (2H,m), 4.65–4.75 (2H, m), 7.05–7.80 (12H, m). LC-MS: 816 (M⁺), 817 (M+H⁺), HPLC-RT: 3.90 min (Waters).

Example 41

N-{1-[(1-sec-Butyl-4-{2-[1-(4-fluoro-benzylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-(4-fluoro-benzylsulfanyl)-N-phenethyl-3-pyrrolidin-2-yl-propionamide.

¹H NMR (270 MHz, CDCl₃): δ0.80–1.20 (18H, m), 1.30–2.20 (12H, m), 2.30–2.70 (5H, m), 2.88 (2H, m), 2.96 (6H, s), 3.01 (3H, s), 3.27 (3H, s), 3.30–4.90 (4H, m), 4.00–4.25 (2H, m), 4.74 (2H, m), 6.92–7.32 (9H, m). LC-MS: 798 (M⁺), 799 (M+H⁺), HPLC-RT: 3.21 min.

Example 42

N-{1-[(1-sec-Butyl-4-{2-[1-(furan-2-ylmethylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-(furan-2-ylmethylsulfanyl)-N-phenethyl-3-pyrrolidin-2-yl-propionamide.

¹H NMR (270 MHz, CDCl₃): δ0.70–1.20 (18H, m), 1.20–1.90 (12H, m), 1.90–2.55 (5H, m), 2.82 (2H, t, 6.9 Hz), 2.96 (6H, s), 3.08 (3H, s), 3.26 (3H, s), 3.31–3.84 (4H, m), 4.05–4.27 (2H, m), 4.62–4.74 (2H, m), 6.18–6.55 (3H, m), 7.19–7.31 (5H, m). LC-MS: 770 (M⁺), 771 (M+H⁺), HPLC-RT: 3.42 min (Waters).

Example 43

N-(1-{[1-sec-Butyl-2-methoxy-4-(2-{2-[2-(4-methoxy-phenyl)-ethylcarbamoyl]-1-methylsulfanyl-ethyl}-pyrrolidin-1-yl)-4-oxo-butyl]-methyl-carbamoyl}-2-methyl-propyl)-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and N-[2-(4-methoxy-phenyl)-ethyl]-3-methylsulfanyl-3-pyrrolidin-2-yl-propionamide.

¹H NMR (270 MHz, CDCl₃): δ0.70–1.20 (18H, m), 1.20–1.90 (12H, m), 2.07 (3H, s), 2.30–2.70 (3H, t, J=7.3 Hz), 2.95 (6H, s), 3.01 (3H, s), 3.30 (3H, s), 3.40–3.70 (4H, m), 3.78 (3H, s), 4.00–4.30 (2H, m), 4.75 (2H, m), 6.82 (2H, d, J=8.6 Hz), 7.11 (2H, d, J=8.6 Hz). LC-MS: 734 (M⁺), 735 (M+H⁺), HPLC-RT: 2.88 min.

Example 44

N-{1-[(1-sec-Butyl-2-methoxy-4-{2-[1-methylsulfanyl-2-(4-[1,2,3]thiadiazol-4-yl-benzylcarbamoyl)-ethyl]-pyrrolidin-1-yl}-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and 3-methylsulfanyl-3-pyrrolidin-2-yl-N-(4-[1,2,3]thiadiazol-4-yl-benzyl)-propionamide.

¹H NMR (270 MHz, CDCl₃): δ0.70–1.10 (18H, m), 1.20–2.00 (12H, m), 2.10 (3H, s), 2.30–2.70 (3H, m), 2.95 (6H, s), 3.01 (3H, s), 3.31 (3H, s), 3.54 (2H, m), 3.70–4.20

(2H, m), 4.30–4.80 (4H, m), 7.43 (2H, d, J=7.9 Hz), 7.98 (2H, d, J=7.9 Hz), 8.69 (1H, J=5.3 Hz). LC-MS: 774 ($M^+$), 775 ($M+H^+$), HPLC-RT: 2.92 min.

Example 45

N-{1-[(4-{2-[2-(1-Benzyl-piperidin-4-ylcarbamoyl)-1-methylsulfanyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide In a similar manner to Example 1, the title compound was obtained from the condensation reaction of (3R*,4S*,5S*)-4-[N,N-dimethyl-L-valyl-(N-methyl-L-valinamido)]-3-methoxy-5-methylheptanoic acid and N-(1-benzyl-piperidin-4-yl)-3-methylsulfanyl-3-pyrrolidin-2-yl-propionamide.
$^1$H NMR (270 MHz, $CDCl_3$): δ0.70–1.20 (22H, in), 1.70–2.80 (15H, m), 2.06 (3H, s), 2.96 (9H, s), 3.33 (3H, s), 3.40–4.05 (6H, in), 4.20–4.40 (5H, in), 4.70 (2H, brs), 7.44 (5H, m). LC-MS: 773 ($M^{30}$), HPLC-RT: 2.33 min.

Example 46

N-[1-({1-sec-Butyl-4-[2-(1-methanesulfinyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide Preparation of 2-(methanesulfinyl-2-phenethylcarbamoyl-ethyl)-pyrrolidine-1-carboxylic acid tert-butyl ester To a stirred solution of 2-(methanesulfanyl-2-phenethylcarbamoyl-ethyl)-pyrrolidine-1-carboxylic acid tert-butyl ester (62 mg, 0.158 mmol) in $CH_2Cl_2$ (2 ml) wad added mCPBA (30 mg, 0.174 mmol) at 0° C. After being stirred at 0° C. for 1 hr, the mixture was quenched with 1N NaOHaq., extracted with AcOEt, washed with saturated NaClaq., dried ($MgSO_4$) and concentrated in vacuo. The resulting residue was purified by preparative TLC ($CH_2Cl_2$:MeOH=95:5) to give 2-(methanesulfinyl-2-phenethylcarbamoyl-ethyl)-pyrrolidine-1-carboxylic acid tert-butyl ester (39 mg, 61%) as colorless oil.
$^1$H NMR (270 MHz, $CDCl_3$): δ1.46(9H, s), 1.20–1.39(2H, in), 1.62–2.40 (6H, m), 2.47(3H, s), 2.83(2H, t, J=6.9 Hz), 3.13–3.33(1H, m), 3.35–3.70(3H, m), 3.75–3.95(1H, m), 3.95–4.15(1H, m), 7.10–7.38(5H, in). LC-MS: 409 ($MH^+$), HPLC-RT: 2.99 min.

The title compound was obtained in a manner analogous to that of Example 1 through the condensation of (3R*,4S*,5S*)-4-[N,N-dimethyl-L-valyl-(N-methyl-L-valinamido)]-3-methoxy-5-methylheptanoic acid and 3-methanesulfinyl-N-phenethyl-3-pyrrolidin-2-yl-propionamide.
$^1$H NMR (270 MHz, $CDCl_3$): δ0.65–1.09 (15H, m), 1.12 (3H, d, J=6.0 Hz), 1.27–2.72 (15H, m), 2.53 (3H, s), 2.82 (2H, t, J=6.9 Hz), 2.94 (6H, s,), 3.03 (3H, s,), 3.29 (3H, s), 3.25–3.65 (4H, m), 3.70–4.05 (1H, m), 4.30–4.50 (1H, m), 4.60–4.85 (2H, m), 6.95–7.37 (5H, m). LC-MS: 720 ($MH^+$), HPLC-RT: 2.50 min.

Example 47

N-[1-({1-sec-Butyl-4-[2-(1-methanesulfonyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide Preparation of 2-(methanesulfonyl-2-phenethylcarbamoyl-ethyl)-pyrrolidine-1-carboxylic acid tert-butyl ester To a stirred solution of 2-(methanesulfanyl-2-phenethylcarbamoyl-ethyl)-pyrrolidine-1-carboxylic acid tert-butyl ester (130 mg, 0.331 mmol) in $CH_2Cl_2$ (4 m) wad added mCPBA (286 mg, 1.66 mmol) at 0° C. After being stirred at RT for 2 hr, the mixture was quenched with 1N NaOHaq., extracted with AcOEt, washed with saturated NaClaq., dried ($MgSO_4$) and concentrated in vacuo. The resulting residue was purified with preparative TLC (n-Hex:AcOEt=1:3) to give 2-(methanesulfonyl-2-phenethylcarbamoyl-ethyl)-pyrrolidine-1-carboxylic acid tert-butyl ester (140 mg, quant) as colorless oil.
$^1$H NMR (270 MHz, $CDCl_3$): δ1.44(9H, s), 1.65–2.80 (6H, m), 2.82(2H, t, J=6.9 Hz), 2.90(3H, s), 3.00–4.00 (5H, m), 4.20–4.40(1H, m), 5.40–5.74(1H, m), 7.05–7.40(5H, m). LC-MS: 425 ($MH^+$), HPLC-RT: 3.45 min.

The title compound was obtained in a manner analogous to that of Example 1 through the condensation of (3R*,4s*,5S*)-4-[N,N-dimethyl-L-valyl-(N-methyl-L-valinamido)]-3-methoxy-5-methylheptanoic acid and 3-methanesulfonyl-N-phenethyl-3-pyrrolidin-2-yl-propionamide.
$^1$H NMR (270 MHz, $CDCl_3$): δ0.65–1.09 (15H, m), 1.14 (3H, d, J=6.3 Hz), 1.25–2.85 (17H, m), 2.94 (6H, s), 2.96 (3H, s), 2.99 (3H, s,), 3.30 (3H, s), 3.25–3.92 (5H, m), 4.00–4.25 (1H, m), 4.50–4.80 (2H, m), 7.05–7.38 (5H, m). LC-MS: 736 ($MH^+$), HPLC-RT: 2.67 min.

Example 48

N-[1-({1-sec-Butyl-2-methoxy-4-[2-(1-methylsulfanyl-2-phenethylcarbamoylethyl)pyrrolidin-1-yl]-4-oxo-butyl}-methyl-carbamoyl)-2-methyl-propyl]-3-methyl-2-methylamino-butyramide To a stirred solution of 2-(1-methylsulfanyl-2-phenethylcarbamoyl-ethyl)-pyrrolidine-1-carboxylic acid tert-butyl ester (1.15 g, 2.93 mmol) in $CH_2Cl_2$ (3 ml) was added TFA at 0° C. After being stirred at 0° C. for 30 min, the mixture was evaporated in vacuo to give 3-methylsulfanyl-N-phenethyl-3-pyrrolidin-2-yl-propionamide TFA salt as a crude oil (1.87 g), which was used without further purification in the next step [The diastereomers were separable by preparative HPLC (column: ODS-80Ts, eluent: 79/21 $H_2O$:$CH_3CN$/0.05% TFA)].

To a stirred solution of (3R*,4S*,5S*)-4-[N-benzyloxycarbonyl-N-methyl-L-valyl-(N-methyl-L-valinamido)]-3-methoxy-5-methylheptanoic acid (1.12 g, 2.05 mmol) which was prepared according to the literature method (Chem.Pharm.Bull, 43(10), 1706–1718, 1995) and the crude 3-methylsulfanyl-N-phenethyl-3-pyrrolidin-2-yl-propionamide TFA salt (1.31 g, 2.05 mmol) obtained above in $CH_2Cl_2$ (3 ml) were added diisopropylethylamine (3.58 mL, 20.5 mmol), WSCI monohydrochloric acid (511 mg, 2.67 mmol), HOBt monohydrate (408 mg, 2.67 mmol) at 0° C. After being stirred at room temperature for 16 hr, the mixture was evaporated in vacuo and dried under a vacuum to give {1-[1-({1-sec-butyl-2-methoxy-4-[2-(1-methylsulfanyl-2-phenethylcarbamoyl-ethyl)-pyrrolidin-1-yl]-4-oxo-butyl}-methyl-carbamoyl)-2-methyl-propylcarbamoyl]-2-methyl-propyl}-methyl-carbamic acid benzyl ester (2.19 g) as a crude oil, which was used without further purification in the next step.

To a stirred solution of {1-[1-({1-sec-butyl-2-methoxy-4-[2-(1-methylsulfanyl-2-phenethylcarbamoyl-ethyl)-pyrrolidin-1-yl]-4-oxo-butyl}-methyl-carbamoyl)-2-methyl-propylcarbamoyl]-2-methyl-propyl}-methyl-carbamic acid benzyl ester (1.1 g) obtained above in tBuOH (36 ml) and $H_2O$ (4 ml) was added Pd(OH)$_2$ on carbon (ca. 20 wt %, 1 g) at room temperature and then the mixture was set under $H_2$ atmosphere. After being stirred at room temperature for 14 hr, the mixture was filtrated through a pad of celite and washed with MeOH. The filtrate and washings were combined and concentrated in vacuo to give the crude gum (1.01 g), which was purified by preparative HPLC (column: ODS-80Ts, eluent: 57/43 $H_2O:CH_3CN/0.05\%$ TFA). The appropriate fractions were lyophilized to obtain the title compound as a white amorphous powder (388 mg, 47%).

$^1$H NMR (270 MHz, CDCl$_3$): δ0.81 (3H, t, J=6.93 Hz), 0.85–1.13(15H, m), 1.22–1.42(2H, m), 1.51–2.18(10H, m), 2.02(3H, s), 2.2–2.49(3H, m), 2.71(3H, s), 2.81(2H, t, J=6.6 Hz), 2.92(3H, s), 3.29(3H, s), 3.33–3.95(4H, m), 4.02–4.16(1H, m), 4.16–4.32(1H, m), 4.56–4.97(2H, m), 6.59(1H, brs), 7.07–7.38(5H, m), 7.60(1H, brs), LC-MS: 690 (MH$^+$), HPLC-RT: 2.76 min. (R-isomer)

The following compounds (Example 49–53) were obtained in a manner analogous to that of Example 48.

Example 49

N-[1-({1-sec-Butyl-4-[2-(1-ethylsulfanyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide In a similar manner to Example 48, the title compound was obtained starting from (3R*,4S*,5S*)-4-[N-benzyloxycarbonyl-N-methyl-L-valyl-(N-methyl-L-valinamido)]-3-methoxy-5-methylheptanoic acid and 3-ethylsulfanyl-N-phenethyl-3-pyrrolidin-2-yl-propionamide.

$^1$H NMR (270 MHz, CDCl$_3$): δ0.68–1.10 (18H, m), 1.16 (3H, t, J=7.3 Hz), 1.20–1.42 (2H, m), 1.55–2.18 (10H, m), 2.18–2.60(3H, m), 2.49 (2H, t, J=7.2 Hz), 2.71 (3H,s), 2.83 (2H, t, J=6.9 Hz), 3.03 (3H, s), 3.29 (3H, s), 3.20–3.78(4H, m), 3.97–4.12 (1H, m), 4.12–4.28(1H, m), 4.65–4.90 (2H, m), 7.08–7.32 (5H, m). LC-MS: 704 (MH$^+$), HPLC-RT: 2.87 min. (R-isomer)

Example 50

N-[-({1-sec-Butyl-2-methoxy-4-oxo-4-[2-(2-phenethylcarbamoyl-1-phenylsulfanyl-ethyl)-pyrrolidin-1-yl]-butyl}-methyl-carbamoyl)-2-methyl-propyl]-3-methyl-2-methylamino-butyramide In a similar manner to Example 48, the title compound was obtained starting from (3R*,4S*,5S*)-4-[N-benzyloxycarbonyl-N-methyl-L-valyl-(N-methyl-L-valinamido)]-3-methoxy-5-methylheptanoic acid and N-phenethyl-3-phenylsulfanyl-3-pyrrolidin-2-yl-propionamide.

$^1$H NMR (270 MHz, CDCl$_3$): δ0.65–1.15 (18H, m), 1.18–2.58 (15H, m), 2.71 (3H, s), 2.60–2.85 (2H, m), 3.03 (3H, s), 3.21 (3H, s), 3.22–3.95 (4H, m), 3.98–4.42 (2H, m), 4.50–4.85 (2H, m), 7.05–7.42 (10H, m). LC-MS: 752 (MH$^+$), HPLC-RT: 3.08 min. (R-isomer)

Example 51

N-[-({1-sec-Butyl-4-[2-(1-tert-butylsulfanyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide In a similar manner to Example 48, the title compound was obtained starting from (3R*,4S*,5S*)-4-[N-benzyloxycarbonyl-N-methyl-L-valyl-(N-methyl-L-valinamido)]-3-methoxy-5-methylheptanoic acid and 3-tert-butylsulfanyl-N-phenethyl-3-pyrrolidin-2-yl-propionamide.

$^1$H NMR (270 MHz, CDCl$_3$): δ0.65–1.40 (18H, m), 1.25 (9H, s), 1.50–2.65 (15H, m), 2.72 (3H, s), 2.75–2.95 (2H, m), 3.04 (3H, s), 3.28 (3H, s), 3.29–3.80 (4H, m), 3.92–4.22 (2H, m), 4.60–4.95 (2H, m), 7.00–7.40 (5H, m). LC-MS: 732 (MH$^+$), HPLC-RT: 3.25 min. (R-isomer)

Example 52

N-[1-({1-sec-Butyl-4-[2-(1-isopropylsulfanyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide In a similar manner to Example 48, the title compound was obtained starting from (3R*,4S*,5S*)-4-[N-benzyloxycarbonyl-N-methyl-L-valyl-(N-methyl-L-valinamido)]-3-methoxy-5-methylheptanoic acid and 3-isopropylsulfanyl-N-phenethyl-3-pyrrolidin-2-yl-propionamide.

$^1$H NMR (270 MHz, CDCl$_3$): δ0.81(3H, t, 6.92 Hz), 0.88–1.11(15H, m), 1.11–1.45(8H, m), 1.50–2.21(11H, m), 2.21–2.60(3H, m), 2.71(3H, s), 2.84(3H, t, J=6.93 Hz), 3.03(3H, s), 3.32(3H, s), 3.39–3.78(4H, m), 3.93–4.29(2H, m), 4.63–4.90(2H, m), 6.70(1H, brs,), 7.07–7.36(5H, m), 7.64(1H, brs). LC-MS: 718 (MH$^+$), HPLC-RT: 2.97 min. (R-isomer)

Example 53

N-{1-[(1-sec-Butyl-2-methoxy-4-oxo-4-{2-[2-phenethylcarbamoyl-1-(2-methyl-propane-2-sulfonyl)-ethyl]-pyrrolidin-1-yl}-butyl)-methyl-carbamoyl]-2-methyl-propyl}-3-methyl-2-methylamino-butyramide In a similar manner to Example 48, the title compound was obtained starting from (3R*,4S*,5S*)-4-[N-benzyloxycarbonyl-N-methyl-L-valyl-(N-methyl-L-valinamido)]-3-methoxy-5-methylheptanoic acid and 3-(2-methyl-propane-2-sulfonyl)-N-phenethyl-3-pyrrolidin-2-yl-propionamide.

$^1$H NMR (270 MHz, CDCl$_3$): δ0.81(3H, t, J=6.93 Hz), 0.85–1.17(15H, m), 1.17–1.52(2H, m), 1.18(9H, s), 1.52–2.59(13H, m), 2.71(3H, s), 2.79(2H, t, J=6.93 Hz), 2.92(3H, s), 3.10–3.76(4H, m), 3.29(3H, s), 3.85–4.41 (2H, m), 4.52–4.90(2H, m), 6.41(1H, brs), 7.00–7.36(5H, m), 7.51(1H, brs). LC-MS: 764 (MH$^+$), HPLC-RT: 2.81 min. (R-isomer)

Example 54

N-[1-({1-sec-Butyl-4-[2-(1-methanesulfonyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide To a stirred solution of {1-[1-({1-sec-butyl-2-methoxy-4-[2-(1-methylsulfanyl-2-phenethylcarbamoyl-ethyl)-pyrrolidin-1-yl]-4-oxo-butyl}-methyl-carbamoyl)-2-methyl-propylcarbamoyl]-2-methyl-propyl}-methyl-carbamic acid benzyl ester (0.35 g) in CH$_2$Cl$_2$ (3 ml) wad added mCPBA (80%: 356 mg, 1.65 mmol) at room temperature. After being stirred at room temperature for 4 hr, the mixture was quenched with 5N NaOH (10 ml), extracted with AcOEt, washed with H$_2$O, dried (MgSO$_4$) and concentrated in vacuo to give {1-[1-({1-sec-butyl-2-methoxy-4-[2-(1-methylsulfonyl-2-phenethylcarbamoyl-ethyl)-pyrrolidin-1-yl]-4-oxo-butyl}-methyl-carbamoyl)-2-methyl-propylcarbamoyl]-2-methyl-propyl}-methyl-carbamic acid benzyl ester (311 mg) as a crude oil, which was used without further purification in the next step.

To a stirred solution of the crude {1-[1-({1-sec-butyl-2-methoxy-4-[2-(1-methylsulfonyl-2-phenethylcarbamoyl-ethyl)-pyrrolidin-1-yl]-4-oxo-butyl}-methyl-carbamoyl)-2-methyl-propylcarbamoyl]-2-methyl-propyl}-methyl-carbamic acid benzyl ester (311 mg) obtained above in tBuOH (9 ml) and H$_2$O (1 ml) was added Pd(OH)$_2$ on carbon(ca. 20 wt %, 1 g) at room temperature and then the mixture was set under H$_2$ atmosphere. After being stirred at room temperature for 13.5 hr, the mixture was filtrated through a pad of celite and washed with MeOH. The filtrate and washings were combined and concentrated in vacuo to give the crude gum (285 mg), which was purified by preparative HPLC (column: ODS-80Ts, eluent: 40/30 H$_2$O:CH$_3$CN/0.05% TFA). The appropriate fractions were lyophilized to give the title compound as a white amorphous powder (160 mg, 58%).

$^1$H NMR (270 MHz, CDCl$_3$): δ0.49–1.14(18H, m), 1.20–1.39(2H, m), 1.48–2.59(13H, m), 2.71(3H, s), 2.77 (2H, d, J=6.6 Hz), 2.95(3H, s), 3.01(3H, s), 3.02–3.98(3H, s), 4.02–4.38(2H, m), 4.42–4.95(2H, m), 6.27(1H, brs), 7.02–7.40(5H, m), 7.81(1H, brs). LC-MS: 722 (MH$^+$), HPLC-RT: 2.61 min. (R-isomer)

The following compounds (Example 55–57) were obtained in a manner analogous to that of Example 54.

Example 55

N-[1-({1-sec-Butyl-4-[2-(1-ethanesulfonyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide In a similar manner to Example 54, the title compound was obtained starting from the oxidation of {1-[1-({1-sec-butyl-4-[2-(1-ethylsulfanyl-2-phenethylcarbamoyl-ethyl)-pyrrolidin-1-yl]-2-methoxy-4-oxo-butyl}-methyl-carbamoyl)-2-methyl-propylcarbamoyl]-2-methyl-propyl}-methyl-carbamic acid benzyl ester with mCPBA followed by hydrogenolysis.

$^1$H NMR (270 MHz, CDCl$_3$): δ0.70–1.18 (18H, m), 1.38 (3H, t, J=7.3 Hz), 1.20–1.43 (2H, m), 1.55–2.86 (13H, m), 2.71 (3H, s), 2.78 (2H, t, J=7.3 Hz), 3.00 (3H, s), 3.29 (3H, s), 3.02–3.81(6H, m), 3.81–3.97 (1H, m), 4.10–4.22 (1H, m), 4.55–4.88 (2H, m), 7.08–7.39 (5H, m). LC-MS: 736 (MH$^+$), HPLC-RT: 2.68 min. (R-isomer)

Example 56

N-[1-({4-[2-(1-Benzenesulfonyl-2-phenethylcarbamoyl-ethyl)-pyrrolidin-1-yl]-1-sec-butyl-2-methoxy-4-oxo-butyl}-methyl-carbamoyl)-2-methyl-propyl]-3-methyl-2-methylamino-butyramide In a similar manner to Example 54, the title compound was obtained starting from the oxidation of {1-[1-({1-sec-butyl-2-methoxy-4-oxo-4-[2-(2-phenethylcarbamoyl-1-phenylsulfanyl-ethyl)-pyrrolidin-1-yl]-butyl}-methyl-carbamoyl)-2-methyl-propylcarbamoyl]-2-methyl-propyl}-methyl-carbamic acid benzyl ester with mCPBA followed by hydrogenolysis.

$^1$H NMR (270 MHz, CDCl$_3$): δ0.65–1.18 (18H, m), 1.30–2.60 (15H, m), 2.71 (3H, s), 2.60–2.80 (2H, m), 2.99 (3H, s), 3.29 (3H, s), 3.10–3.75 (4H, m), 3.88–4.17 (2H, m), 4.60–4.88 (2H, m), 7.00–7.32 (5H, m), 7.40–7.75 (3H, m), 7.89 (1H, d, J=7.3 Hz). LC-MS: 784 (MH$^+$), HPLC-RT: 2.92 min. (R-isomer)

Example 57

N-{1-[(1-sec-Butyl-2-methoxy-4-oxo-4-{2-[2-phenethylcarbamoyl-1-(propane-2-sulfonyl)-ethyl]-pyrrolidin-1-yl}-butyl)-methyl-carbamoyl]-2-methyl-propyl}-3-methyl-2-methylamino-butyramide In a similar manner to Example 54, the title compound was obtained starting from the oxidation of {1-[1-({1-sec-butyl-4-[2-(1-isopropylsulfanyl-2-phenethylcarbamoyl-ethyl)-pyrrolidin-1-yl]-2-methoxy-4-oxo-butyl}-methyl-carbamoyl)-2-methyl-propylcarbamoyl]-2-methyl-propyl}-methyl-carbamic acid benzyl ester with mCPBA followed by hydrogenolysis.

$^1$H NMR (270 MHz, CDCl$_3$): δ0.81(3H, t, J=6.93 Hz), 0.85–1.15(15H, m), 1.15–1.49(8H, m), 1.50–2.67(13H, m), 2.71(3H, s), 2.78(2H, t, J=6.92 Hz), 3.00(3H, s), 3.10–3.79(4H, m), 3.28(3H, s), 3.95–4.37(2H, m), 4.45–4.98(2H, m), 6.31(1H, brs), 7.02–7.38(5H, m), 7.54 (1H, brs). LC-MS: 750 (MH$^+$), HPLC-RT: 2.72 min. (R-isomer)

Example 58

N-[1-({1-sec-Butyl-2-methoxy-4-[2-(1-methylsulfanyl-2-phenethylcarbamoyl-propyl)-pyrrolidin-1-yl]-4-oxo-butyl}-methyl-carbamoyl)-2-methyl-propyl]-2-dimethylamino-3-methyl-butyramide Preparation of 2-(1-methylsulfanyl-2-phenethylcarbamoyl-propyl)-pyrrolidine-1-carboxylic acid tert-butyl ester To a stirred solution of (S)-2-(2-ethoxycarbonyl-propenyl)-pyrrolidine-1-carboxylic acid tert-butyl ester (200 mg, 0.71 mmol) in THF (3 ml) wad added NaSMe (95%, 156 mg, 2.12 mmol) at room temperature. After being stirred in sealed tube at 150° C. for 14 hr, the mixture was cooled to room temperature and quenched with 1N HCl (20 ml), extracted with AcOEt, dried (MgSO$_4$) and concentrated in vacuo to give 2-(2-carboxy-1-methylsulfanyl-propyl)-pyrrolidine-1-carboxylic acid tert-butyl ester (223 mg) as a crude oil, which was used without further purification in the next step.

To a stirred solution of the crude 2-(2-carboxy-1-methylsulfanyl-propyl)-pyrrolidine-1-carboxylic acid tert-butyl ester (223 mg) obtained above in CH$_2$Cl$_2$ (3 ml) was added phenethylamine(0.18 ml, 1.41 mmol), WSCI monohydrochloride(203 mg, 1.06 mmol), HOBt monohydrate(162 mg, 1.06 mmol) and diisopropylethylamine(0.37 ml, 2.12 mmol) at room temperature. After being stirred at room temperature for 4.5 hr, the mixture was quenched with 1N HCl (20 ml), extracted with AcOEt, dried (MgSO$_4$) and concentrated in vacuo to give a crude oil, which was purified by flash column chromatography (hexane:AcOEt=3:1) to give 2-(1-methylsulfanyl-2-phenethylcarbamoyl-propyl)-pyrrolidine-1-carboxylic acid tert-butyl ester as an oil(123 mg, 43%).

The title compound was obtained in a manner analogous to that of Example 1 through condensation of (3R*,4S*,5S*)-4-[N,N-dimethyl-L-valyl-(N-methyl-L-valinamido)]-3-methoxy-5-methylheptanoic acid and 2-methyl-3-methylsulfanyl-N-phenethyl-3-pyrrolidin-2-yl-propionamide prepared from its N-Boc derivative obtained above.

$^1$H NMR (270 MHz, CDCl$_3$): δ1.27(6H, d, J=7.6 Hz), 1.45(9H, s), 1.58–2.25(4H, m), 2.26–2.45(4H, m), 2.84 (2H, t, J=6.93 Hz), 3.13–3.75(5H, m), 3.83–4.04(1H, m), 6.03(1H, brs), 7.08–7.40(5H, m). LC-MS: 407(MH$^+$), HPLC-RT: 4.06 min.

Example 59

N-[-({1-sec-Butyl-2-methoxy-4-[2-(1-methylsulfanyl-2-phenethylcarbamoyl-propyl)-pyrrolidin-1-yl]-4-oxo-butyl}-methyl-carbamoyl)-2-methyl-propyl]-2-methylamino-3 methyl-butyramide In a similar manner to Example 48, the title compound was obtained starting from (3R*,4S*,5S*)-4-[N-benzyloxycarbonyl-N-methyl-L-valyl-(N-methyl-L-valinamido)]-3-methoxy-5-methylheptanoic acid and 3-methylsulfanyl-N-phenethyl-3-pyrrolidin-2-yl-propionamide.

$^1$H NMR (270 MHz, CDCl$_3$): δ0.60–1.16 (18H, m), 1.16–1.42 (5H, m), 1.50–2.10 (9H, m), 2.07 (3H, s), 2.15–2.52 (3H, m), 2.72 (3H, s), 2.69–2.88 (2H, m), 3.01 (3H, s), 3.31 (3H, s), 3.26–3.77 (4H, m), 3.99–4.18 (1H, m), 4.18–4.30 (1H, m), 4.59–5.89 (2H, m), 7.02–7.36 (4H, m). LC-MS: 704 (MH$^+$), HPLC-RT: 2.88 min.

Example 60

N-(1-{[1-sec-Butyl-4-(2-{2-[2-(3-hydroxy-phenyl)-ethylcarbamoyl]-1-methylsulfanyl-propyl}-pyrrolidin-1-yl)-2-methoxy-4-oxo-butyl]-methyl-carbamoyl}-2-methyl-propyl)-2-dimethylamino-3-methyl-butyramide Preparation of (2S)-2-[(1R,2S)-2-benzyloxycarbonyl-1-methylsulfanyl-propyl]-pyrrolidine-1-carboxylic acid tert-butyl ester To a stirred solution of AcSMe (24.4 g, 0.27 mol) in THF (580 ml) cooled in an ice-bath was added KOEt (22.8 g, 0.27 mol). After stirring for 3.5 h at room temperature, phenol (11.9 ml, 0.14 mol) and a solution of (2S)-2-(2-benzyloxycarbonyl-propenyl)-pyrrolidine-1-carboxylic acid tert-butyl ester (15.6 g, 0.045 mol) in THF (50 ml) were successively added to the mixture. After 45 min, the mixture was quenched with saturated NH$_4$Cl aqueous solution and concentrated in vacuo. The residue was diluted with EtOAc (600 ml), and washed with 1N NaOH aqueous solution (300 ml×3) and saturated brine (200 ml). The organic layer was dried over anhydrous Na$_2$SO$_4$ and then concentrated in vacuo. The residue was purified by column chromatography on silica gel (hexane/EtOAc=9/1) to give (2S)-2-[(1R,2S)-2-benzyloxycarbonyl-1-methylsulfanyl-propyl]-pyrrolidine-1-carboxylic acid tert-butyl ester which was contaminated with PhOH. The collected fraction which included (2S)-2-[(1R,2S)-2-benzyloxycarbonyl-1-methylsulfanyl-propyl]-pyrrolidine-1-carboxylic acid tert-butyl ester was washed with 5N NaOH aqueous solution (300 ml) and H$_2$O (300 ml) to remove phenol, and dried over anhydrous MgSO$_4$. The organic layer was concentrated in vacuo to obtain (2S)-2-[(1R,2S)-2-benzyloxycarbonyl-1-methylsulfanyl-propyl]-pyrrolidine-1-carboxylic acid tert-butyl ester (12.5 g, 70%).

$^1$H NMR (400 MHz, CDCl3) δ1.10–1.39 (m, 3H), 1.46 (s, 9H), 1.64–1.76 (m, 1H), 1.81–1.97 (m, 3H), 2.06 (s, 3H), 2.52–2.68 (m, 1H), 3.12–3.25 (m, 1H+5/9H), 3.34–3.62 (m, 1H+4/9H), 3.82–4.04 (m, 1H), 5.04–5.26 (m, 2H), 7.26–7.40 (m, 5H) (two rotational isomeric mixture); MS (ES) m/z 416 (M$^+$+Na); HPLC (rt) 3.08 min.

Preparation of (2S)-2-[(1R,2S)-2-Carboxy-1-methylsulfanyl-propyl]-pyrrolidine-1-carboxylic acid tert-butyl ester A mixture of (2S)-2-[(1R,2S)-2-benzyloxycarbonyl-1-methylsulfanyl-propyl]-pyrrolidine-1-carboxylic acid tert-butyl ester (4.4 g, 11.2 mmol) and Pd(OH)$_2$ on carbon(ca.20 wt %, 2.0 g) in EtOH (50 mL) was stirred at room temperature under H$_2$ atmosphere. After being stirred at room temperature for 14 hr, the mixture was filtrated through a pad of celite and washed with MeOH. The filtrate and washings were combined and concentrated in vacuo to give a crude gum, which was purified by flush column chromatography (hexane:AcOEt=1:1) to give (2S)-2-[(R,2S)-2-carboxy-1-methylsulfanyl-propyl]-pyrrolidine-1-carboxylic acid tert-butyl ester as a gum (3.39 g, 98%).

$^1$H NMR (270 MHz, CDCl$_3$): δ1.39 (3H, d, J=5.94 Hz), 1.45 (9H, s), 1.58–2.01 (5H, m), 2.12 (3H, s), 2.47–2.69 (1H, m), 3.11–3.75 (2H, m), 3.92–4.16 (1H, m). LC-MS:304 (MH$^+$), HPLC-RT: 3.45 min.

Preparation of (2S)-2-{(1R,2S)-2-[2-(3-hydroxy-phenyl)-ethylcarbamoyl]-1-methylsulfanyl-propyl}-pyrrolidine-1-carboxylic acid tert-butyl ester To a stirred solution of (2S)-2-[(1R,2S)-2-carboxy-1-methylsulfanyl-propyl]-pyrrolidine-1-carboxylic acid tert-butyl ester (1.7 g, 5.6 mmol) in CH$_2$Cl$_2$ (20 mL) were added 3-hydroxyphenethylamine hydrobromide (2.44 g, 11.2 mmol), BOP(3.72 g, 8.4 mmol), HOBT (1.29 g, 8.4 mmol), and diisopropylethylamine (4.88 mL, 28.0 mmol) at room temperature. After being stirred at room temperature for 2 hr, the mixture was quenched with 1N HCl (80 mL×3), extracted with AcOEt, dried (MgSO$_4$) and concentrated in vacuo to give a crude oil, which was purified by flash column chromatography (hexane:AcOEt=1:1) to give (2S)-2-{(1R,2S)-2-[2-(3-hydroxy-phenyl)-ethylcarbamoyl]-1-methylsulfanyl-propyl}-pyrrolidine-1-carboxylic acid tert-butyl ester as a gum (2.07 g, 87%).

$^1$H NMR (270 MHz, CDCl$_3$) δ1.26–1.35 (m, 3H), 1.49 (s, 9H), 1.70–1.97 (m, 1H), 2.12 (s, 3H), 2.24–2.41 (m, 1H), 2.67–2.83 (m, 2H), 3.08–3.36 (m, 2H), 3.45–3.66 (m, 2H), 3.77–3.91 (m, 1H), 3.98–4.10 (m, 1H), 5.80 (br, 1H), 6.65–6.80 (m, 2H), 6.92 (brs, 1H), 7.18 (t,J=7.8 Hz, 1H), 7.86 (br, 1H); MS (ES) m/z 423 (M$^+$+1); HPLC-RT: 3.57 min.

Preparation of the Title Compound

In a similar manner to Example 1, the title compound was obtained as single stereoisomer from the condensation reaction of (3R*,4S*,5S*)-4-[N,N-dimethyl-L-valyl-(N-methyl-L-valinamido)]-3-methoxy-5-methylheptanoic acid and (2S)-2-{(1R,2S)-2-[2-(3-hydroxy-phenyl)-ethylcarbamoyl]-1-methylsulfanyl-propyl}-pyrrolidine-1-carboxylic acid tert-butyl ester. The stereochemistry of the product was retained as indicated in each component.

$^1$H NMR (270 MHz, CDCl$_3$): δ0.82 (3H, d, J=6.92 Hz), 0.81–1.17 (15H, m), 1.17–1.41 (8H, m), 150–210 (9H, m), 2.05 (3H, s). 2.10–2.65 (3H, m), 2.65–2.84 (2H, m), 2.99 (6H,s), 3.11 (3H, s), 3.32 (3H, s), 3.22–3.60 (4H, m), 3.62–3.92 (1H, m), 3.92–4.11 (1H, m), 4.55–4.81 (2H, m), 6.60–6.85 (3H, m), 7.14 (1H, t, J=7.59 Hz). LC-MS: 734 (MH$^+$), HPLC-RT: 2.62 min.

Example 61

N-[1-({1-sec-Butyl-4-[2-(2-{[2-(3-hydroxy-phenyl)-ethyl]-methyl-carbamoyl}-1-methylsulfanyl-propyl)-pyrrolidin-1-yl]-2-methoxy-4-oxo-butyl}-methyl-carbamoyl)-2-methyl-propyl]-2-dimethylamino-3-methyl-butyramide Preparation of (2S)-2-((1R,2S)-2-{[2-(3-hydroxy-phenyl)-ethyl]-methyl-carbamoyl}-1-methylsulfanyl-propyl)-pyrrolidine-1-carboxylic acid tert-butyl ester To a stirred solution of (2S)-2-[(1R,2S)-2-carboxy-1-methylsulfanyl-propyl]-pyrrolidine-1-carboxylic acid tert-butyl ester (1.70 g, 5.6 mmol) in CH$_2$Cl$_2$ (20 mL) were added N-methyl-3-hydroxyphenethylamine hydrobromide (2.44 g, 11.2 mmol), BOP (3.72 g, 8.4 mmol), HOBT (1.29 g, 8.4 mmol), and diisopropylethylamine (4.88 mL, 28.0 mmol) at room temperature. After being stirred at room temperature for 2 hr, the mixture was quenched with 1N HCl (80 mL×3), extracted with AcOEt, dried (MgSO$_4$) and concentrated in vacuo to give a crude oil (3.83 g), which was then purified by flash column chromatography (hexane:AcOEt=1:1) to give (2S)-2-((1R,2S)-2-{[2-(3-hydroxy-phenyl)-ethyl]-methyl-carbamoyl}-1-methylsulfanyl-propyl)-pyrrolidine-1-carboxylic acid tert-butyl ester as a gum (1.38 g, 56%).

$^1$H NMR (270 MHz, CDCl$_3$): δ1.27 (3H, d, J=7.26 Hz), 1.30–1.56 (9H, m), 1.5–2.1 (5H, m), 1.99∝2.33 (3H, m), 2.49–2.80 (1H, m), 1.90–2.88 (2H, m), 2.88–3.56 (3H, m), 3.56–4.15 (1H, m), 6.52–6.89 (3H, m), 7.00–7.21 (1H, m). LC-MS: 437 (MH$^+$), HPLC-RT: 3.90 min.

Preparation of the Title Compound

In a similar manner to Example 1, the title compound was obtained as single stereoisomer from the condensation reaction of (3R*,4S*,5S*)-4-[N,N-dimethyl-L-valyl-(N-methyl-L-valinamido)]-3-methoxy-5-methylheptanoic acid and (2S)-2-((1R,2S)-2-{[2-(3-hydroxy-phenyl)-ethyl]-methyl-carbamoyl}-1-methylsulfanyl-propyl)-pyrrolidine-1-carboxylic acid tert-butyl ester. The stereochemistry of the product was retained as indicated in each component.

$^1$H NMR (270 MHz, CDCl$_3$): δ0.62–1.17 (18H, m), 1.17–1.42 (5H, m), 1.45–2.10 (9H, m), 1.91–2.11 (3H, m), 211–2.62 (3H, m), 2.70–2.84 (2H, m), 2.99 (6H, s), 3.06 (3H, s), 3.30 (3H, s), 3.38 (3H, s), 3.20–3.65 (4H, m), 3.77–4.25 (2H, m), 4.40–4.95 (2H, m), 6.7.83 (3H, m), 6.92–7.18 (1H, m). LC-MS: 748 (MH$^+$), HPLC-RT: 2.78 min.

Example 62

N-[1-({1-sec-Butyl-4-[2-(1-ethylsulfanyl-2-{[2-(3-hydroxy-phenyl)-ethyl]-methyl-carbamoyl}-propyl)-pyrrolidin-1-yl]-2-methoxy-4-oxo-butyl}-methyl-carbamoyl)-2-methyl-propyl]-2-dimethylamino-3-methyl-butyramide Preparation of (2S)-2-[(1R,2S)-2-benzyloxycarbonyl-1-ethylsulfanyl-propyl]-pyrrolidine-1-carboxylic acid tert-butyl ester To a stirred suspension of t-BuOK (609 mg, 5.43 mmol) in THF (90 ml) was added EtSH (8.04 ml, 0.11 mol). After stirring for 30 min at room temperature, a solution of (2S)-2-(2-benzyloxycarbonyl-propenyl)-pyrrolidine-1-carboxylic acid tert-butyl ester (3.75 g, 10.8 mmol) in THF (75 ml) was added to the mixture. After 2.5 h, the mixture was quenched with saturated NH$_4$Cl aqueous solution, and then concentrated in vacuo. The residue was diluted with EtOAc (400 ml), and washed with saturated NH$_4$Cl aqueous solution (150 ml), saturated NaHCO$_3$ aqueous solution (150 ml) and H$_2$O (150 ml). The organic layer was dried over anhydrous Na$_2$SO$_4$, and then concentrated in vacuo. The residue was purified by column chromatography on silica gel (hexane/EtOAc=12/1 to 8/1) to give (2S)-2-[(1R,2S)-2-benzyloxycarbonyl-1-ethylsulfanyl-propyl]-pyrrolidine-1-carboxylic acid tert-butyl ester (3.66 g, 83%).

$^1$H NMR (400 MHz, CDCl$_3$) δ1.19 (t, J=7.4 Hz, 3H), 1.28–1.40 (m, 3H), 1.50 (s, 9H), 1.60–1.72 (m, 1H), 1.78–2.00 (m, 3H), 2.41–2.64 (m, 3H), 3.16–3.28 (m, 1H), 3.32–365 (m, 2H), 3.76–4.00 (m, 1H), 5.04–5.23 (m, 2H), 7.26–7.41 (m, 5H) (two rotational isomeric mixture); MS (ES) m/z 430 (M$^+$+Na); HPLC-RT: 3.20 min.

Preparation of (2S)-2-((1R,2S)-1-ethylsulfanyl-2-{[2-(3-hydroxy-phenyl)-ethyl]-carbamoyl}-propyl)-pyrrolidine-1-carboxylic acid tert-butyl ester In a similar manner to Example 61, (2S)-2-((1R,2S)-1-ethylsulfanyl-2-{[2-(3-hydroxy-phenyl)-ethyl]-methyl-carbamoyl}-propyl)-pyrrolidine-1-carboxylic acid tert-butyl ester was prepared from (2S)-2-[(1R,2S)-2-benzyloxycarbonyl-1-ethylsulfanyl-propyl]-pyrrolidine-1-carboxylic acid tert-butyl ester through hydrogenolysis followed by amidation with N-methyl-3-hydroxyphenethylamine hydrobromide.

$^1$H NMR (270 MHz, CDCl$_3$): δ1.05–1.55 (15H, m), 1.55–2.35 (5H, m), 2.38–2.70 (2H, m), 2.70–3.00 (5H, m), 3.05–4.28 (6H, m), 6.50–6.90 (3H, m), 7.00–7.23(1H, m); LC-MS: 451 (MH$^+$), HPLC-RT: 4.12 min.

Preparation of the Title Compound

In a similar manner to Example 1, the title compound was obtained as single stereoisomer from the condensation reaction of (3R*,4S*,5S*)-4-[N,N-dimethyl-L-valyl-(N-methyl-L-valinamido)]-3-methoxy-5-methylheptanoic acid and (2S)-2-((1R,2S)-1-ethylsulfanyl-2-{[2-(3-hydroxy-phenyl)-ethyl]-methyl-carbamoyl}-propyl)-pyrrolidine-1-carboxylic acid tert-butyl ester. The stereochemistry of the product was retained as indicated in each component.

$^1$H NMR (270 MHz, CD3OD): δ0.75–1.50 (26H, m), 1.55–2.85 (13H, m), 2.85–3.20 (12H, m), 3.25–4.25 (10H, m), 4.55–4.92 (2H, m), 6.48–6.78 (3H, m), 6.92–7.18 (1H, m); LC-MS: 762 (MH$^+$), HPLC-RT; 2.94 min.

Example 63

N-(1-{[1-sec-Butyl-4-(2-{1-ethylsulfanyl-2-[2-(3-hydroxy-phenyl)-ethylcarbamoyl]-propyl}-pyrrolidin-1-yl)-2-methoxy-4-oxo-butyl]-methyl-carbamoyl}-2-methyl-propyl)-2-dimethylamino-3-methyl-butyramide Preparation of (2S)-2-{(1R,2S)-1-ethylsulfanyl-2-[2-(3-hydroxy-phenyl)-ethylcarbamoyl]-propyl}-pyrrolidine-1-carboxylic acid tert-butyl ester In a similar manner to Example 62, (2S)-2-{(1R,2S)-1-ethylsulfanyl-2-[2-(3-hydroxy-phenyl)-ethylcarbamoyl]-propyl}-pyrrolidine-1-carboxylic acid tert-butyl ester was prepared from (2S)-2-[(1R,2S)-2-benzyloxycarbonyl-1-ethylsulfanyl-propyl]-pyrrolidine-1-carboxylic acid tert-butyl ester through hydrogenolysis followed by amidation with 3-hydroxyphenethylamine hydrobromide.

$^1$H NMR (270 MHz, CDCl$_3$): δ1.20 (3H, t, J=7.3 Hz), 1.31 (3H, d, 6.9 Hz), 1.48 (9H, s), 1.55–2.40 (5H, m), 2.42–2.65 (2H, m), 2.67–2.85 (2H, m), 3.18–3.40 (2H, m), 3.45–3.85 (3H, m), 3.90–4.05 (1H, m), 5.99 (1H, brs), 6.62–6.80 (2H, m), 6.90 (1H, brs), 7.17 (1H, t, J=7.6 Hz); LC-MS: 437 (MH$^+$), HPLC-RT: 3.77 min.

Preparation of the Title Compound

In a similar manner to Example 1, the title compound was obtained as single stereoisomer from the condensation reaction of (3R*,4S*,5S*)-4-[N,N-dimethyl-L-valyl-(N-methyl-L-valinamido)]-3-methoxy-5-methylheptanoic acid and (2S)-2-{(1R,2S)-1-ethylsulfanyl-2-[2-(3-hydroxy-phenyl)-ethylcarbamoyl]-propyl}-pyrrolidine-1-carboxylic acid tert-butyl ester. The stereochemistry of the product was retained as indicated in each component.

$^1$H NMR (270 MHz, CDCl$_3$): δ0.57–1.60 (26H, m), 1.60–2.30 (8H, m), 2.30–2.85 (7H, m), 2.95 (6H, s), 3.00–3.20 (3H, m), 3.27 (3H, s), 3.30–3.95 (5H, m), 3.95–4.30 (2H, m), 4.30–4.90 (2H, m), 6.40 (1H, brs), 6.58–6.78 (2H, m), 6.93 (1H, S), 7.12 (1H, t, J=7.6 Hz). 7.79(1H, brs); LC-MS: 748 (MH$^+$), HPLC-RT: 2.72 min.

Example 64

N-(1-{[1-sec-Butyl-4-(2-{1-dimethylcarbamoylmethylsulfanyl-2-[2-(3-hydroxy-phenyl)-ethylcarbamoyl]-ethyl}-pyrrolidin-1-yl)-2-methoxy-4-oxo-butyl]-methyl-carbamoyl}-2-methyl-propyl)-2-dimethylamino-3-methyl-butyramide In a similar manner to Example 1, the title compound was obtained starting from (3R*,4S*,5S*)-4-[N,N-dimethyl-L- valyl-(N-methyl-L-valinamido)]-3-methoxy-5-methylheptanoic acid and 2-{1-dimethylcarbamoylmethylsulfanyl-2-[2-(3-hydroxy-phenyl)-ethylcarbamoyl]-ethyl}-pyrrolidine-1-carboxylic acid tert-butyl ester.
$^1$H NMR (270 MHz, CD$_3$OD): δ0.75–1.18 (18H, m), 1.18–2.20 (11H, m), 2.21–2.81 (5H, m), 2.90 (6H, s), 3.00–3.20 (6H, m), 3.30 (3H, s), 3.25–3.90 (7H, m), 4.00–4.30 (2H, m), 4.60–5.00 (2H, m), 6.50–6.75 (3H, m), 6.98–7.15 (1H, m); LC-MS: 748 (MH$^+$), HPLC-RT: 2.41 min.

Example 65

Ethyl-carbamic acid 2-{1-[1-(4-{[2-(2-dimethylamino-3-methyl-butyrylamino)-3-methyl-butyryl]-methyl-amino}-3-methoxy-5-methyl-heptanoyl)-pyrrolidin-2-yl]-2-phenethylcarbamoyl-ethylsulfanyl}-ethyl ester To a stirred solution of N-{1-[(1-sec-butyl-4-{2-[1-(2-hydroxy-ethylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide (50 mg, 0.067 mmol) in CH$_2$Cl$_2$ (1 ml) was added N, N'-carbonyl diimidazole (33 mg, 0.204 mmol) and pyridine (0.020 ml, 0.202 mmol) at 0° C. After being stirred at room temperature for 24 hr, the mixture was concentrated in vacuo. The resulting crude oil was dissolved in CH$_3$CN (1 ml), and ethylamine hydrochloride (55 mg, 0.674 mmol) and pyridine (0.067 ml, 0.676 mmol) was added to the solution at 0° C. After being stirred at room temperature for 15 hr, the mixture was concentrated in vacuo to give a crude oil, which was purified by preparative HPLC (column: ODS-80TS, eluent: 38:32 H$_2$O:CH$_3$CN/0.05% TFA). The appropriate fractions were lyophilized to give the title compound as a white amorphos powder (46 mg, 84%).
$^1$H NMR (270 MHz, CD$_3$OD): δ0.57–1.18 (21H, m), 1.25–1.50 (2H, m), 1.60–2.21 (9H, m), 2.23–2.85 (9H, m), 2.86 (6H, s), 3.08 (2H, q), 3.14 (3H, s), 3.31(3H, s), 3.30–3.95 (5H, m), 3.95–4.25 (2H, m), 4.60–4.95 (2H, m), 7.10–7.35(5H, m); LC-MS: 805 (MH$^+$), HPLC-RT: 2.73 min.

Example 66

Ethyl-carbamic acid 3-(2-{3-[1-(4-{[2-(2-dimethylamino-3-methyl-butyrylamino)-3-methyl-butyryl]-methyl-amino}-3-methoxy-5-methyl-heptanoyl)-pyrrolidin-2-yl]-2-methyl-3-methylsulfanyl-propionylamino}-ethyl)-phenyl ester To a stirred solution of N-(1-{[1-sec-butyl-4-(2-{2-[2-(3-hydroxy-phenyl)-ethylcarbamoyl]-1-methylsulfanyl-propyl}-pyrrolidin-1-yl)-2-methoxy-4-oxo-butyl]-methyl-carbamoyl}-2-methyl-propyl)-2-dimethylamino-3-methyl-butyramide (30 mg, 0.035 mmol) in CH$_2$Cl$_2$ (0.5 mL) were added ethyl isocyanate (0.042 mL, 0.53 mmol) and diisopropylethylamine (0.062 mL, 0.35 mmol) at room temperature. After being stirred at room temperature for 13hr, the mixture was concentrated in vacuo to give a crude oil (58 mg), which was purified by preparative HPLC (column:ODS-8OTs, eluent: 35/35 H$_2$O:CH$_3$CN/0.05% TFA). The appropriate fractions were lyophilized to give the title compound as a white amorphous powder (13 mg, 39%).
$^1$H NMR (270 MHz, CDCl$_3$): δ0.68–1.19 (18H, m), 1.15–1.46 (8H, m), 1.50–2.10 (9H, m), 2.07 (3H, s), 2.10–2.68 (3H, m), 2.75–2.90 (2H, m), 2.94 (6H, s), 3.03 (3H, s), 3.32 (3H, s), 3.30–3.78 (4H, m), 3.95 (2H, q, J=6.93 Hz), 3.80–4.08 (1H, m), 4.08–4.37 (1H, m), 4.59–5.86 (2H, m), 6.81–7.09 (3H, m), 7.12–7.29 (1H, m); LC-MS: 805(MH$^+$), HPLC-RT: 2.70 min.

The following Examples illustrate pharmaceutical preparations containing a compound provided by the present invention.

Example 67

| Tablet formation | | | |
|---|---|---|---|
| Ingredients | | mg/tablet | |
| N-[1-({1-sec-Butyl-2-methoxy-4-[2-(1-methyl-sulfanyl-2-phenethylcarbamoyl-ethyl)-pyrrolidin-1-yl]-4-oxo-butyl}-methyl-carbamoyl)-2-methyl-propyl]-3-methyl-2-methylamino-butyramide | 5 | 25 | 100 |
| anhydrous lactose | 103 | 83 | 35 |
| croscarmellose sodium | 6 | 6 | 8 |
| povidone K30 | 5 | 5 | 6 |
| magnesium stearate | 1 | 1 | 1 |
| Total weight | 120 | 120 | 150 |

Interlocking gelatin capsules each containing the following ingredients were manufactured in a manner known to one skilled in the art.

Example 68

| Ingredients | | mg/tablet | |
|---|---|---|---|
| N-[1-({1-sec-Butyl-2-methoxy-4-[2-(1-methyl-sulfanyl-2-phenethylcarbamoyl-ethyl)-pyrrolidin-1-yl]-4-oxo-butyl}-methyl-carbamoyl)-2-methyl-propyl]-3-methyl-2-methylamino-butyramide | 5 | 25 | 100 |
| hydrous lactose | 159 | 123 | 148 |
| corn starch | 25 | 35 | 40 |
| talc | 10 | 15 | 10 |
| magnesium stearate | 11 | 2 | 2 |
| Total weight | 200 | 200 | 300 |

Example 69

| Injection solution/emulsion preparation | |
|---|---|
| ingredients | mg/ml |
| N-[1-({1-sec-Butyl-2-methoxy-4-[2-(1-methyl-sulfanyl-2-phenethylcarbamoyl-ethyl)-pyrrolidin-1-yl]-4-oxo-butyl}-methyl-carbamoyl)-2-methyl-propyl]-3-methyl-2-methylamino-butyramide | 1 mg |
| glycerol | 10–50 mg |
| lecithin | 20–50 mg |
| soy oil | 1.5 mg |
| glycerol | 8–12 mg |
| water | q.s. ml |

What is claimed is:
1. A compound of the formula,

(I)

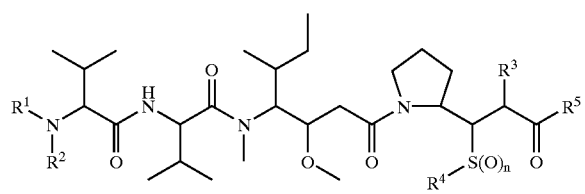

wherein
R$^1$, R$^2$ and R$^3$ are each independently hydrogen or (C$_1$–C$_4$)-alkyl;
R$^4$ is hydrogen;
  alkyl optionally substituted with one to three substituents selected from the group consisting of hydroxy, alkoxy, amino, mono- or di-alkylamino, carboxy alkoxycarbonyl, carbamoyl, alkylcarbonyloxy, carbamoyloxy and halogen;
  alkenyl;
  alkynyl;
  (C$_3$–C$_7$)-cycloalkyl;
  aryl optionally substituted with one to three substituents selected from the group consisting of halogen, alkoxycarbonyl, carbamoyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino and benzyl;
  aralkyl with the aryl group optionally substituted with one to three substituents selected from the group consisting of halogen, alkoxycarbonyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino and benzyl; or
  heterocyclylalkyl;
R$^5$ is (C$_1$–C$_6$)-alkylamino;
  hydroxy;
  (C$_3$–C$_7$)-cycloalkylamino optionally substituted by phenyl or benzyl;
  arylamino;
  aralkylamino having (C$_1$–C$_4$)-alkylene and the aryl group optionally substituted with one to three substituents selected from the group consisting of halogen, alkoxycarbonyl, sulfamoyl, alkylcarbonyloxy, carbamoyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino and benzyl;
  (C$_1$–C$_4$)-alkoxy;
  benzylhydrazino;
  heterocyclyl optionally substituted with one to three substituents selected from the group consisting of benzyl, benzhydryl, alkyl, hydroxy, alkoxy, alkylcarbamoyloxy, amino, mono- or di-alkylamino, acylamino, alkoxycarbonylamino, phenyl and halogen;
  heterocyclylamino;
  heterocycloalkylamino with the heterocyclyl group optionally substituted with one to three substituents selected from the group consisting of benzyl, benzhydryl, alkyl, hydroxy, alkoxy, alkylcarbamoyloxy, amino, dialkylamino, acylamino, alkoxycarbonylamino and halogen; and
  aralkyloxy and aralkyl both optionally substituted with one to three substituents from the group consisting of halogen, alkoxycarbonyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino, aminosulfonyl and benzyl; and
n is 0, 1 or 2;
or a pharmaceutically acceptable salt thereof.

2. The compound of claim 1 wherein R$^1$ is (C$_1$–C$_4$)-alkyl.
3. The compound of claim 1 wherein R$^1$ is methyl.
4. The compound of claim 2 wherein R$^2$ is (C$_1$–C$_4$)-alkyl.
5. The compound of claim 4 wherein R$^2$ is methyl.
6. The compound of claim 5 wherein R$^3$ is hydrogen or methyl.
7. The compound of claim 1 wherein R$^4$ is hydrogen; alkyl optionally substituted with one to three substituents selected from the group consisting of hydroxy, amino, mono- or di-alkylamino, carbamoyl, acetoxy, carbamoyloxy and carboxy; alkenyl; alkynyl; (C$_3$–C$_7$)-cycloalkyl; aryl optionally substituted with one to three substituents selected from the group consisting of alkyl, alkoxy, hydroxy, halogen, amino, mono- or di-alkylamino, alkylthio and alkylcarbonylamino; aralkyl with the aryl group optionally substituted with one to three substituents selected from the group consisting of alkyl, alkoxy, hydroxy, halogen, amino, mono- or di-alkylamino, and alkylthio; or heterocyclylalkyl.
8. The compound of claim 1 wherein
  R$^5$ is (C$_1$–C$_6$)-alkylamino;
  hydroxy;
  (C$_3$–C$_7$)-cycloalkylamino optionally substituted by phenyl or benzyl;
  arylamino;
  aralkylamino having (C$_1$–C$_4$)-alkylene and the aryl group optionally substituted with one to three substituents selected from the group consisting of H$_2$NSO$_2$—, hydroxy, alkyl, benzyl, alkoxy, carbamoyloxy and heterocyclyl;
  (C$_1$–C$_4$)-alkoxy;
  benzylhydrazino;
  heterocyclyl optionally substituted by benzyl or benzhydryl;
  heterocyclylamino;
  heterocycloalkyamino with the heterocyclyl group optionally substituted with one to three substituents selected from the group consisting of alkyl, hydroxy, alkoxy, alkylcarbamoyloxy, amino, dialkylamino, acylamino, alkoxycarbonylamino and halogen; or
  aralkyloxy and aralkyl both optionally substituted with one to three substituents from the group consisting of halogen, alkoxycarbonyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino, aminosulfonyl and benzyl.
9. The compound of claim 8 wherein R$^5$ is phenylethylamino; phenylethoxy; benzyloxy; 2-naphthylmethylamino; benzylpiperazino; 1,2,3,4-tetrahydroisoquinolino; t-butoxy; hydroxy; 4-H$_2$NSO$_2$PhCH$_2$CH$_2$; 2-, 3- or 4-hydroxyphenylethylamino; N-benzylphenethylamino; 4-t-butylbenzylamino; benzylamino; N-methylphenethylamino; 2-, 3- or 4-hydroxyphenylethyl-N-methylamino; 4-benzhydrylpiperazino; 2-phenylcyclopropylamino; thienylethylamino; 2-pyridylethylamino; 5-ethylpyrazol; 4,3-dimethoxyphenylethylamino; benzylhydrazino; benzothiazol-2-ylmethyl-amino; 2-pyridin-4-yl-amino; 3,4-dimethoxy-phenyl-ethyl-methyl-amino; benzothiazol-2-ylmethyl-amino; 2-pyridin-3-yl-ethylamino; pyridin-4-ylmethyl-amino; thiazol-2-ylamino; naphthalen-2-ylamino; 4-chloro-phenyl-ethylamino; 4-methoxy-phenyl-ethylamino; 4-(1,2,3)thiadiazol-4-yl-benzylamino; 2-cyclohexylamino or 1-benzyl-piperidin-4-ylamino.
10. The compound of claim 9 wherein n is 0.
11. The compound of claim 9 wherein R$^1$ and R$^2$ are methyl, R$^3$ is hydrogen and n is 0.

12. The compound of claim 1, wherein $R^1$ and $R^2$ are methyl, $R^3$ is hydrogen and n is 2.

13. The compound of claim 12 which is N-[1-({1-sec-Butyl-4-[2-(1-methanesulfonyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide.

14. The compound of claim 1 wherein $R^1$ is methyl, $R^2$ and $R^3$ are hydrogen and n is 0.

15. The compound of claim 14, which is selected from the group consisting of:
   a) N-[1-({1-sec-Butyl-4-[2-(1-ethylsulfanyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide,
   b) N-[1-({1-sec-Butyl-2-methoxy-4-oxo-4-[2-(2-phenethylcarbamoyl-1-phenylsulfanyl-ethyl)-pyrrolidin-1-yl]-butyl}-methyl-carbamoyl)-2-methyl-propyl]-3-methyl-2-methylamino-butyramide,
   c) N-[1-({1-sec-Butyl-4-[2-(1-tert-butylsulfanyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide,
   d) N-[1-({1-sec-Butyl-2-methoxy-4-[2-(1-methylsulfanyl-2-phenethylcarbamoyl-ethyl)-pyrrolidin-1-yl]-4-oxo-butyl}-methyl-carbamoyl)-2-methyl-propyl]-3-methyl-2-methylamino-butyramide,
   e) N-[1-({1-sec-Butyl-4-[2-(1-isopropylsulfanyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide,
   f) N-{1-[(1-sec-Butyl-2-methoxy-4-oxo-4-{2-[2-phenethylcarbamoyl-1-(2-methyl-propane-2-sulfonyl)-ethyl]-pyrrolidin-1-yl}-butyl)-methyl-carbamoyl]-2-methyl-propyl}-3-methyl-2-methylamino-butyramide,
   g) N-(1-{[1-sec-Butyl-4-(2-{2-[2-(3-hydroxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-3-methyl-2-methylamino-butyramide, and
   h) N-(1-{[1-sec-Butyl-4-(2-{1-tert-butylsulfanyl-2-[2-(3-hydroxy-phenyl)-ethylcarbamoyl]-ethyl}-pyrrolidin-1-yl)-2-methoxy-4-oxo-butyl]-methyl-carbamoyl}-2-methyl-propyl)-3-methyl-2-methylamino-butyramide.

16. The compound of claim 1 wherein $R^1$ is methyl, $R^2$ and $R^3$ are hydrogen and n is 2.

17. The compound of claim 16, which is selected from the group consisting of:
   a) N-[1-({1-sec-Butyl-4-[2-(1-ethanesulfonyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide,
   b) N-[1-({4-[2-(1-Benzenesulfonyl-2-phenethylcarbamoyl-ethyl)-pyrrolidin-1-yl]-1-sec-butyl-2-methoxy-4-oxo-butyl}-methyl-carbamoyl)-2-methyl-propyl]-3-methyl-2-methylamino-butyramide,
   c) N-[1-({1-sec-Butyl-4-[2-(1-methanesulfonyl-2-phenethylcarbamoyl-ethyl)-pyrrolidin-1-yl]-2-methoxy-4-oxo-butyl}-methyl-carbamoyl)-2-methyl-propyl]-3-methyl-2-methylamino-butyramide, and
   d) N-{1-[(1-sec-Butyl-2-methoxy-4-oxo-4-{2-[2-phenethylcarbamoyl-1-(propane-2-sulfonyl)-ethyl]-pyrrolidin-1-yl}-butyl)-methyl-carbamoyl]-2-methyl-propyl}-3-methyl-2-methylamino-butyramide.

18. The compound of claim 1 wherein $R^1$ and $R^3$ are methyl, $R^2$ is hydrogen, and n is 0.

19. The compound of claim 18, which is selected from the group consisting of,
   a) N-[1-({1-sec-Butyl-2-methoxy-4-[2-(1-methylsulfanyl-2-phenethylcarbamoyl-propyl)-pyrrolidin-1-yl]-4-oxo-butyl}-methyl-carbamoyl)-2-methyl-propyl]-2-methylamino-3-methyl-butyramide, and
   b) N-[1-({1-sec-Butyl-4-[2-(1-tert-butylsulfanyl-2-phenethylcarbamoyl-propyl)-pyrrolidin-1-yl]-2-methoxy-4-oxo-butyl}-methyl-carbamoyl)-2-methyl-propyl]-2-methylamino-3-methyl-butyramide.

20. The compound of claim 1 wherein $R^1$, $R^2$ and $R^3$ are methyl and n is 0.

21. The compound of claim 1 having the formula (I-I),

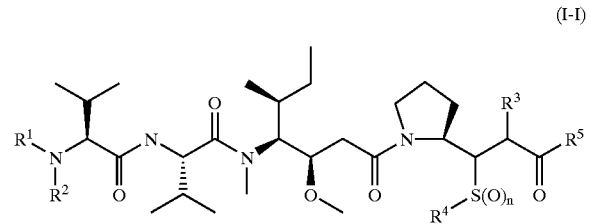

(I-I)

or a pharmaceutically acceptable salt thereof.

22. The compound of claim 21 wherein $R^1$ and $R^2$ are methyl, $R^3$ is hydrogen, and n is 2.

23. The compound of claim 21 wherein $R^1$ is methyl, $R^2$ and $R^3$ are hydrogen, and n is 0.

24. A pharmaceutical composition comprising a compound of claim 1 and a pharmaceutically acceptable carrier.

25. The pharmaceutical composition of claim 24 which is suitable for oral or parenteral administration.

26. A method of treating colorectal cancer, lung cancer, breast cancer, stomach cancer, cervical cancer or bladder cancer comprising administering to a patient in need of such treatment a therapeutically effective amount of at least one compound of claim 1.

27. A method of treating colorectal, lung or breast cancer comprising administering to a patient in need of such treatment a therapeutically effective amount of at least one compound of claim 21.

28. A process for the preparation of a compound of claim 1 comprising
condensing an acid of the formula (II),

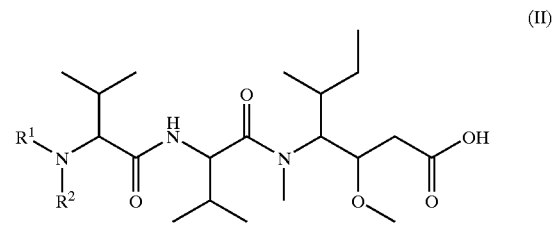

(II)

wherein $R^1$ and $R^2$ are as defined in claim 1, with a compound of the formula (III)

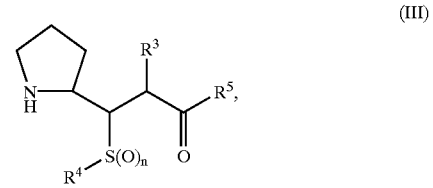

(III)

wherein $R^3$, $R^4$, $R^5$ and n are as defined in claim 1.

29. The compound N-[1-({1-sec-Butyl-4-[2-(2-{[2-(3-hydroxy-phenyl)-ethyl]-methyl-carbamoyl}-1-methylsulfanyl-propyl)-pyrrolidin-1-yl]-2-methoxy-4-oxo-butyl}-methyl-carbamoyl)-2-methyl-propyl]-2-dimethylamino-3-methyl-butyramide.

30. A process for the preparation of a compound of claim 1 comprising condensing an acid of the formula (IV)

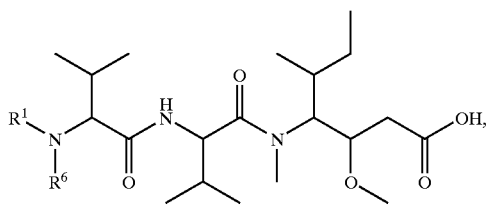

(IV)

wherein
$R^1$ is hydrogen or $(C_1-C_4)$-alkyl; and
$R^6$ is a protecting group;
with a compound of the formula (III)

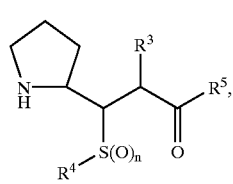

(III)

wherein $R^3$, $R^4$, $R^5$ and n are as defined in claim 1, in the presence of a condensing agent.

31. The method of claim 30 which is followed by removal of the protecting group.

32. A compound of formula

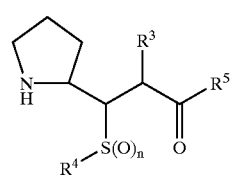

(III)

wherein
$R^3$ is hydrogen or $(C_1-C_4)$-alkyl;
$R^4$ is hydrogen;
  alkyl optionally substituted with one to three substituents selected from the group consisting of hydroxy, alkoxy, amino, mono- or di-alkylamino, carboxy, alkoxycarbonyl, carbamoyl, alkylcarbonyloxy and halogen;
  alkenyl;
  alkynyl;
  $(C_3-C_7)$-cycloalkyl;
  aryl optionally substituted with one to three substituents selected from the group consisting of halogen, alkoxycarbonyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino and benzyl;
  aralkyl with the aryl group optionally substituted with one to three substituents selected from the group consisting of halogen, alkoxycarbonyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino and benzyl; or
  heterocyclylalkyl;
$R^5$ is $(C_1-C_6)$-alkylamino;
  hydroxy;
  $(C_3-C_7)$-cycloalkylamino optionally substituted by phenyl or benzyl;
  arylamino;
  aralkylamino having $(C_1-C_4)$-alkylene and the aryl group optionally substituted with one to three substituents selected from the group consisting of halogen, alkoxycarbonyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino and benzyl;
  $(C_1-C_4)$-alkoxy;
  benzylhydrazino;
  heterocyclyl optionally substituted with one to three substituents selected from the group consisting of benzyl, benzhydryl, alkyl, hydroxy, alkoxy, alkylcarbamoyloxy, amino, mono- or di-alkylamino, acylamino, alkoxycarbonylamino, phenyl and halogen;
  heterocyclylamino;
  heterocycloalkylamino with the heterocyclyl group optionally substituted with one to three substituents selected from the group consisting of benzyl, benzhydryl, alkyl, hydroxy, alkoxy, alkylcarbamoyloxy, amino, dialkylamino, acylamino, alkoxycarbonylamino and halogen; or
  aralkyloxy and aralkyl both optionally substituted with one to three substituents from the group consisting of halogen, alkoxycarbonyl, sulfamoyl, alkylcarbonyloxy, cyano, mono- or di-alkylamino, alkyl, alkoxy, phenyl, phenoxy, trifluoromethyl, trifluoromethoxy, alkylthio, hydroxy, alkylcarbonylamino, heterocyclyl, 1,3-dioxolyl, 1,4-dioxolyl, amino, aminosulfonyl and benzyl; and
n is 0, 1 or 2.

33. A compound of the formula

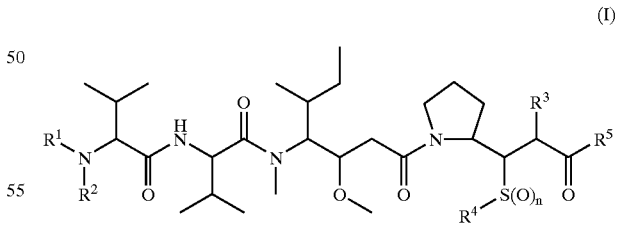

(I)

wherein
$R^1$, $R^2$ and $R^3$ are each independently or $(C_1-C_4)$-alkyl;
$R^4$ is phenyl; methyl; t-butyl; 4-t-butylphenyl; 4-methoxyphenyl; 2-aminoethyl; 2-dimethylaminoethyl; $ZHNCH_2CH_2$— wherein Z is benzyloxycarbonyl; 4-methylthiophenyl; cyclohexyl; 2-, 3-, or 4-hydroxyphenyl; 4-acetoaminophenyl; 4-fluorophenyl; ethyl; i-propyl; benzyl; 2-acetoxyethyl; 2-diethylcarbamoyloxyethyl; phenylethyl; allyl;

n-pentyl; 2-naphthyl; 4-flourobenzyl; 2-furylmethyl or 2-hydroxyethyl;

$R^5$ is $(C_1-C_6)$-alkylamino;

hydroxy;

$(C_3-C_7)$-cycloalkylamino optionally substituted by phenyl or benzyl;

arylamino;

aralkylamino having $(C_1-C_4)$-alkylene and the aryl group optionally substituted with one to three substituents selected from the group consisting of halogen, alkoxycarbonyl, sulfamoyl, alkylcarbonyloxy, carbamoyloxy, cyano, mono- or di-alkylamino, alkyl, alkoxy, phenyl, phenoxy, trifluoromethyl, trifluoromethoxy, alkylthio, hydroxy, alkylcarbonylamino, hetherocyclyl, 1,3-dioxolyl, 1,4-dioxolyl, amino and benzyl;

$(C_1-C_4)$-alkoxy;

benzhydrazino;

heterocyclyl optionally substituted with one to three substituents selected from the group consisting of benzyl, benzhydryl, alkyl, hydroxy, alkoxy, alkylcarbamoyloxy, amino, mono- or di-alkylamino, acylamino, alkoxycarbonylamino, phenyl and halogen;

heterocyclylamino;

heterocycloalkylamino with the heterocyclyl group optionally substituted with one to three substituents selected from the group consisting of benzyl, benzhydryl, alkyl, hydroxy, alkoxy, alkylcarbamoyloxy, amino, dialkylamino, acylamino, alkoxycrbonylamino and halogen; and aralyloxy and aralkyl both optionally substituted with one to three substituents from the group consisting of halogen, alakoxycarbonyl, sulfamoyl, alkylcarbonyloxy, cyano, mono- or di-alkylamino, alkyl, alkoxy, phenyl, phenoxy, trifluromethyl, trifluoromethoxy, alkylthio, hydroxy, alkylcarbonylamino, heterocyclyl, 1,3-dioxolyl, 1,4-dioxolyl, amino, aminosulfonyl and benzyl; and n is 0, 1 or 2.

or a pharmaceutically acceptable salt thereof.

34. A compound of the formula (I)

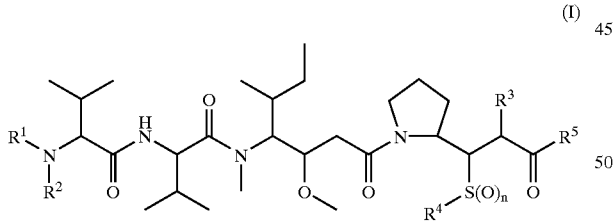

(I)

wherein $R^1$ and $R^2$ are methyl;

$R^3$ is hydrogen;

$R^4$ is phenyl; methyl; t-butyl; 4-t-butylphenyl; 4-methoxyphenyl; 2-aminoethyl; 2-dimethylaminoethyl; $ZHNCH_2CH_2$— wherein Z is benzyloxycarbonyl; 4-methylthiophenyl; cyclohexyl; 2-, 3-, or 4-hydroxyphenyl; 4-acetoaminophenyl; 4-fluorophenyl; ehtyl; i-propyl; benzyl; 2-acetoxyethyl; phenylethyl; allyl; n-pentyl; 2-naphthyl; 4fluorobenzyl; 2-furylmethyl or 2-hydroxyethyl;

$R^5$ is phenylethylamino; phenylethoxy; benzyloxy; 2-naphthylmethylamino; benzylpiperazino; 1,2,3,4-tetrahydroisoquinolino; t-butoxy; hydroxy; $4-H_2NSO_2PhCH_2CH_2$; 2-, 3- or 4-hydroxphenylethylamino; N-benzylphenethylamino; 4-t-butylbenzylamino; benzylamino; N-methylphenethylamino, 2-, 3- or 4-hydroxyphenylethyl-N-methylamino; 4-benzhydrylpiperazino; 2-phenylcyclopropylamino; thienylethylamino; 2-pyridylethylamino; 5-ethylpyrozol; 4,3-dimethoxyphenylethylamino; benzylhydrazino; benzothiazol-2-ylmethyl-amino; 2-pyridin-4-yl-amino; 3,4-dimethoxy-phenyl-ethyl-methyl-amino; benzothiazol-2-ylmethyl-amino; 2-pyridin-3-yl-ethylamino; pryidin-4-ylmethyl-amino; thiazol-2-ylamino; naphthalen-2-ylamino; 4-chloro-phenyl-ethylamino; 4-methoxy-phenyl-ethylamino; 4-(1,2,3) thiadiazol-4-yl-benzylamino; 2-cyclohexylamino or 1-benzyl-piperidin-4-ylamino; and n is 0, or a pharmaceutically acceptable salt thereof.

35. The compound of claim 34 selected from the group consisting of a) N-[1-({1-sec-Butyl-2-methoxy-4-oxo-4-[2-(2-phenethylcarbamoyl-1-phenylsulfanyl-ethyl)-pyrrolidin-1-yl]-butyl}-methyl-carbomoyl)-2-methyl-propyl]-2-dimethylamino-3-methyl-butyramide.

b) N-[1-({1-sec-Butyl-2-methoxy-4-[2-(1-methylsulfanyl-2-phenethylcarbamoyl-ethyl)-pyrrolidin-1-yl]-4-oxo-butyl}-methyl-carbamoyl)-2-methyl-propyl]-2-dimethylamino-3-methyl-butyramide, c) N-[1-({1-sec-Butyl-4-[2-(1-(S)-tert-butylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide, d) N-{1-[(1-sec-Butyl-4-{2-[1-(4-tert-butyl-phenylsulfanyl)-2-phenethylcarbamoyl-ethyl]-pyrrolidin-1-yl}-2-methyoxy-4-oxo-butyl)-methyl-carbamoyl]-2-methyl-propyl}-2-dimethylamino-3-methyl-butyramide, e) N-{1-[(1-sec-Butyl-2-methoxy-4-{2-[1-(4-methoxy-phenylsulfanyl)-2-phenethylcarbamoyl-ethyl]-pyrrolidin-1-yl}-4-oxo-butyl)-methyl-carbamoyl]-2-methyl-propyl}-2-dimethylamino-3-methyl-butyramide, f) 3-[1-(4-{[2-(2-Dimethylamino-3-methyl-butyrylamino)-3-methyl-butyryl]-methyl-amino}-3-methoxy-5-methyl-heptanoyl)-pyrrolidin-2-yl]-3-methylsulfanyl-propionic acid phenethyl ester, g) 3-[1-(4-{[2-(2-Dimethylamino-3-methyl-butyrylamino)-3-methyl-butyryl]-methyl-amino}-3-methoxy-5-methyl-heptanoyl)-pyrrolidin-2-yl]-3-methylsulfanyl-propionic acid benzyl ester, h) N-(1-{[1-sec-Butyl-2-methoxy-4-(2-{1-methylsulfanyl-2-[(naphthalen-2-ylmethyl)-carbamoyl]-ethyl}-pyrrolidin-1-yl)-4-oxo-butyl]-methyl-carbamoyl}-2-methyl-propyl)-2-dimethylamino-3-methyl-butyramide, and i) N-{1-[(4-{2-[1-(2-Amino-ethylsulfanyl)-2-phenethylcarbamoyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide.

36. The compound of claim 34 selected from the group consisting of j) N-{1-[(4-{2-[3-(4-Benzyl-piperazin-1-yl)-1-methylsulfanyl-3-oxo-propyl]-pyrrolidin-1-yl}-1-secbutyl-2-methoxy-4-oxo-butyl)-methyl-carbamoyl]-2-methyl-propyl}-2-dimethylamino-3-methyl-butyramide, k) N-{1-[(1-sec-Butyl-4-{2-[3-(3,4-dihydro-1H-isoquinolin-2-yl)-1-methylsulfanyl-3-oxo-propyl]-pyrrolidin-1-yl}-2-methoxy-4-oxo-butyl)-methyl-carbamoyl]-2-methyl-propyl}-2-dimethylamino-3-methyl-butyramide, l) N-{1-[(1-sec-Butyl-4-{2-[1-(2-dimethylamino-ethylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide, m) (2-{1-[1-(4-{[2-(2-Dimethylamino-3-methyl-butyrylamino)-3-methyl-butyryl]-methyl-amino}-3-methoxy-5-methyl-heptanoyl)-pyrrolidin-2-yl]-2-phenethylcarbamoyl-ethylsulfanyl}-ethyl)-carbamic acid benzyl ester, n) N-{1-[(1-sec-Butyl-2-methoxy-4-{2-[1-(4-methylsulfanyl-phenylsulfanyl)-2-phenethylcarbamoyl-ethyl]-pyrrolidin-1-yl}-4-oxo-butyl)-methyl-carbamoyl]-2-methyl-propyl}-2-dimethylamino-3-methyl-butyramide, o) N-[1-({1-sec-Butyl-4-[2-(1-cyclohexylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide, p) N-{1-[(1-sec-Butyl-4-{2-[1-(S)-(4-hydroxy-phenylsulfanyl)-2-phenethylcarbamoyl-ethyl]-pyrrolindin-1-yl}-2-methoxy-4-oxo-butyl)-methyl-carbamoyl]-2-methyl-propyl}-2-dimethylamino-3-methyl-butyramide, q) N-{1-[(1-sec-Butyl-4-{2-[1-(R)-(4-hydroxy-phenylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide, r) N-{1-[(4-{2-[1-(4-Acetylamino-phenylsulfanyl)-2-phenethylcarbamoyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide, and s) N-{1-[(1-sec-Butyl-4-{2-[1-(4-flouro-phenylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide.

37. The compound of claim 34 selected from the group consisting of t) N-[1-({1-sec-Butyl-4-[2-(1-(R)-tert-butylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide, u) N-[1-({1-sec-Butyl-4-[2-(1-ethylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide, v) N-[1-({1-sec-Butyl-4-[2-(1-isopropylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide, w) N-[1-({1-sec-Butyl-4-[2-(1-tert-butylsulfanyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide, x) N-[1-({4-[2-(1-Benzylsulfanyl-2-phenethylcarbamoyl-ethyl)-pyrrolidin-1-yl]-1-sec-butyl-2-methoxy-4-oxo-butyl}-methyl-carbamoyl)-2-methyl-propyl]-2-dimethylamino-3-methyl-butyramide, y) N-{1-[(1-sec-Butyl-4-{2-[1-(2-hydroxy-phenylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide, z) N-{1-[(1-sec-Butyl-4-{2-[1-(3-hydroxy-phenylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide, aa) N-{1-[(1-sec-Butyl-4-{2-[1-(2-hydroxy-ethylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide, bb) Acetic acid 2-{1-[1-(4-{[2-(2-(2-dimethylamino-3-methyl-butyrylamino)-3-methyl-butyryl]-methyl-amino}-3-methoxy-5-methyl-heptanoyl)-pyrrolidin-2-yl]-2-phenethylcarbamoyl-ethylsulfanyl}-ethyl ester, and cc) 3-[1-(4-{[2-(2-Dimethylamino-3-methyl-butyrylamino)-3-methyl-butyryl]-methyl-amino}-3-methoxy-5-methyl-heptanoyl)-pyrrolidin-2-yl]-3-methylsulfanyl-propionic acid tert-butyl ester.

38. The compound of claim 34 selected from the group consisting of dd) 3-[1-(4-{[2-(2-Dimethylamino-3-methyl-butyrylamino)-3-methyl-butyryl]-methyl-amino}-3-methoxy-5-methyl-heptanoyl)-pyrrolidin-2-yl]-3-methylsulfanyl-propionic acid, ee) N-(1-{[1-sec-Butyl-2-methoxy-4-(2-{1-methylsulfanyl-2-[2-(4-sulfamoyl-phenyl)-ethylcarbamoyl]-ethyl}-pyrrolidin-1-yl)-4-oxo-butyl]-methyl-carbamoyl}-2-methyl-propyl)-2-dimethylamino-3-methyl-butyramide, ff) N-(1-{[1-sec-Butyl-4-(2-{2-[2-(4-hydroxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide, gg) N-{1-[(1-sec-Butyl-2-methoxy-4-{2-[2-(methyl-phenethyl-carbamoyl)-1-methylsulfanyl-ethyl]-pyrrolidin-1-yl}-4-oxo-butyl)-methyl-carbamoyl]-2-methyl-propyl}-2-dimethylamino-3-methyl-butyramide, hh) N-{1-[(4-{2-3-(4-Benzhydryl-piperazin-1-yl)-1-methylsulfanyl-3-oxo-propyl]-pyrrolidin-1-yl}-1-sec-butyl-2-methoxy-4-oxo-butyl)-methyl-carbamoyl]-2-methyl-propyl}-2-dimethylamino-3-methyl-butyramide, ii) N-(1-{[1-sec-Butyl-4-(2-{2-[2-(2-hydroxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide, jj) N-(1-{[1-sec-Butyl-4-(2-{2-[2-(3-hydroxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide, kk) N-{1-[(4-{2-[2-(Benzyl-phenethyl-carbamoyl)-1-methylsulfanyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide, ll) N-{1-[(1-sec-Butyl-2-methoxy-4-{2-[1-methylsulfanyl-2-(2-phenyl-cyclopropylcarbamoyl)-ethyl]-pyrrolidin-1-yl}-4-oxo-butyl)-methyl-carbamoyl]-2-methyl-propyl}-2-dimethylamino-3-methyl-butyramide, and mm) N-{1-[(1-sec-Butyl-4-{2-[2-(4-tert-butyl-benzylcarbamoyl)-1-methylsulfanyl-ethyl]-pyrrolidin-1-yl}-2-methoxy-4-oxo-butyl)-methyl-carbamoyl]-2-methyl-propyl}-2-dimethylamino-3-methyl-butyramide.

39. The compound of claim 34 selected from the group consisting of nn) N-[1-({4-[2-(2-Benzylcarbamoyl-1-methylsulfanyl-ethyl)-pyrrolidin-1-yl]-1-sec-butyl-2-methoxy-4-oxo-butyl}-methyl-carbamoyl)-2-methyl-propyl]-2-dimethylamino-3-methyl-butyramide, oo) N-[1-({1-sec-Butyl-2-methoxy-4-oxo-4-[2-(2-phenethylcarbamoyl-1-phenethylsulfanyl-ethyl)-pyrrolidin-1-yl]-butytl}-methyl-carbamoyl)-2-methyl-propyl]-2-dimethylamino-3-methyl-butyramide, pp) N-[1-({4-[2-(1-Allylsulfanyl-2-phenethylcarbamoyl-ethyl)-pyrrolidin-1-yl]-1-sec-butyl-2-methoxy-4-oxo-butyl}-methyl-carbamoyl)-2-methyl-propyl]-2-dimethylamino-3-methyl-butyramide, qq) N-{1-[(4-{2-[2-(N'-Benzyl-hydrazinocarbonyl)-1-methylsulfanyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide, rr) N-{1-[(1-sec-Butyl-2-methoxy-4-{2-[1-methylsulfanyl-2-(2-pyridin-4-yl-ethylcarbamoyl)-ethyl]-pyrrolidin-1-yl}-4-oxo-butyl)-methyl-carbamoyl]-2-methyl-propyl}-2-dimethylamino-3-methyl-butyramide, ss) N-(1-{[4-(2-{2-[(Benzothiazol-2-ylmethyl)-carbamoyl]-1-methylsulfanyl-ethyl}-pyrrolidin-1-yl)-1-sec-butyl-2-methoxy-4-oxo-butyl]-methyl-carbamoyl}-2-methyl-propyl)-2-dimethylamino-3-methyl-butyramide, tt) N-{1-[(1-sec-Butyl-2-methoxy-4-{2-[1-methylsulfanyl-2-(2-thiophen-2-yl-ethylcarbamoyl)-ethyl]-pyrrolidin-1-yl}-4-oxo-butyl)-methyl-carbamoyl]-2-methyl-propyl}-2-dimethylamino-3-methyl-butyramide, uu) N-{1-[(1-sec-Butyl-2-methoxy-4-{2-[1-methylsulfanyl-2-(2-pyridin-3-yl-ethylcarbamoyl)-ethyl]-pyrrolidin-1-yl}-4-oxo-butyl)-methyl-carbamoyl]-2-methyl-propyl}-2-dimethylamino-3-methyl-butyramide, vv) N-{1-[(1-sec-Butyl-2-methoxy-4-{2-[1-methylsulfanyl-2-(2-pyridin-2-yl-ethylcarbamoyl)-ethyl]-pyrrolidin-1-yl}-4-oxo-butyl)-methyl-carbamoyl]-2-methyl-propyl}-2-dimethylamino-3-methyl-butyramide, and ww) N-(1-{[1-sec-Butyl-2-methoxy-4-(2-{1-methylsulfanyl-2-[(pyridin-4-ylmethyl)-carbamoyl]-ethyl}-pyrrolidin-1-yl)-4-oxo-butyl]-methyl-carbamoyl}-2-methyl-propyl)-2-dimethylamino-3-methyl-butyramide.

40. The compound of claim 34 selected from the group consisting of xx) N-(1-{[1-sec-Butyl-4-(2-{2-[2-(3H-imidazol-4-yl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamlno-3-methyl-butyramide, yy) N-{1-[(1-sec-Butyl-2-methoxy-4-{2-[1-methylsulfanyl-2-(thiazol-2-ylcarbamoyl)-ethyl]-pyrrolidin-1-yl}-4-oxo-butyl)-methyl-carbamoyl]-2-methyl-propyl}-2-dimethylamino-3-methyl-butyramide, zz) N-{1-[(1-sec-Butyl-2-methoxy-4-{2-[1-methylsulfanyl-2-(naphthalen-2-ylcarbamoyl)-ethyl]-pyrrolidin-1-yl}-4-oxo-butyl)-methyl-carbamoyl]-2-methyl-propyl}-2-dimethylamino-3-methyl-butyramide, aaa) N-[1-({1-sec-Butyl-4-[2-(2-cyclohexylcarbamoyl-1-methylsulfanyl-ethyl)-pyrrolidin-1-yl]-2-methoxy-4-oxo-butyl}-methyl-carbamoyl)-2-methyl-propyl]-2-dimethylamino-3-methyl-butyramide, bbb) N-[1-({1sec-Butyl-4-[2-(2-{[2-(3,4-dimethoxy-phenyl)-ethyl]-methyl-carbamoyl}-1-methylsulfanyl-ethyl)-pyrrolidin-1-yl]-2-methoxy-4-oxo-butyl}-methyl-carbamoyl)-2-methyl-propyl]-2-dimethylamino-3-methyl-butyramide, ccc) N-(1-{[1-sec-Butyl-4-(2-{2-[2-(3,4-dimethoxy-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide, ddd) N-(1-{[1sec-Butyl-4-(2-{2-[2-(4-chloro-phenyl)-ethylcarbamoyl]-1-methylsulfanyl-ethyl}-pyrrolidin-1-yl)-2-methoxy-4-oxo-butyl]-methyl-carbamoyl}-2-methyl-propyl)-2-dimethylamino-3-methyl-butyramide, eee) N-[1-({1-sec-Butyl-2-methoxy-4-oxo-4-[2-(1-pentylsulfanyl-2-phenethylcarbamoyl-ethyl)-pyrrolidin-1-yl]-butyl}-methyl-carbamoyl)-2-methyl-propyl]-2-dimethylamino-3-methyl-butyramide, fff) N-{1-[(1-sec-Butyl-2-methoxy-4-{2-[1-(naphthalen-2-ylsulfanyl)-2-phenethylcarbamoyl-ethyl]-pyrrolidin-1-yl}-4-oxo-butyl)-methyl-carbamoyl]-2-methyl-propyl}-2-dimethylamino-3-methyl-butyramide, and ggg) N-{1-[(1-sec-Butyl-4-{2-[1-(4-fluoro-benzylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide.

41. The compound of claim 34 selected from the group consisting of hhh) N-{1-[(1-sec-Butyl-4-{2-[1-(furan-2-ylmethylsulfanyl)-2-phenethylcarbamoyl-ethyl]-pyrrolidin-1-yl}-2-methoxy-4-oxo-butyl)-methyl-carbamoyl]-2-methyl-propyl}-2-dimethylamino-3-methyl-butyramide, iii) N-(1-{[1-sec-Butyl-2-methoxy-4-(2-{2-[2-(4-methoxy-phenyl)-ethylcarbamoyl]-1-methylsulfanyl-ethyl}-pyrrolidin-1-yl)-4-oxo-butyl]-methyl-carbamoyl}-2-methyl-propyl)-2-dimethylamino-3-methyl-butyramide, jjj) N-{1-[(1-sec-Butyl-2-methoxy-4-{2-[1-methylsulfanyl-2-(4-[1,2,3]thiadiazol-4-yl-benzylcarbamoyl)-ethyl]-pyrrolidin-1-yl}-4-oxo-butyl)-methyl-carbamoyl]-2-methyl-propyl}-2-dimethylamino-3-methyl-butyramide, kkk) N-{1-[(4-{2-[2-(1-Benzyl-piperidin-4-ylcarbamoyl)-1-methylsulfanyl-ethyl]-pyrrolidin-1-yl}-1-sec-butyl-2-methoxy-4-oxo-butyl)-methyl-carbamoyl]-2-methyl-propyl}-2-dimethylamino-3-methyl-butyramide, lll) N-(1-{[1-sec-Butyl-4-(2-{1-tert-butylsulfanyl-2-[2-(4-hydroxy-phenyl)-ethylcarbamoyl]-ethyl}- pyrrolidin-1-yl)-2-methoxy-4-oxo-butyl]-methyl-carbamoyl}-2-methyl-propyl)-2-dimethylamino-3-methyl-butyramide, mmm) N-(1-{[1-sec-Butyl-4-(2-{1-tert-butylsulfanyl-2-[2-(3-hydroxy-phenyl)-ethylcarbamoyl]-ethyl}-pyrrolidin-1-yl)-2-methoxy-4-oxo-butyl]-methyl-carbamoyl}-2-methyl-propyl)-2-dimethylamino-3-methyl-butyramide, nnn) N-(1-{[1-sec-Butyl-4-(2-{1-tert-butylsulfanyl-2-[2-(2hydroxy-phenyl)-ethylcarbamoyl]-ethyl}-pyrrolidin-1-yl)-2-methoxy-4-oxo-butyl]-methyl-carbamoyl}-2-methyl-propyl)-2-dimethylamino-3-methyl-butyramide, ooo) N-(1-{[1-sec-Butyl-4-(2-{1-dimethylcarbamoylmethylsulfanyl-2-[2-(3-hydroxy-phenyl)-ethylcarbamoyl]-ethyl}pyrrolidin-1-yl)-2-methoxy-4-oxo-butyl]-methyl-carbamoyl}-2-methyl-propyl)-2-dimethylamino-3-methyl-butyramide, ppp) N-[1-({1-sec-Butyl-4-[2-(1-dimethylcarbamoylmethylsulfanyl-2-phenethylcarbamoyl-ethyl)pyrrolidin-1-yl]-2-methoxy-4-oxo-butyl}-methyl-carbamoyl)-2-methyl-propyl]-2-dimethylamino-3-methyl-butyramide, and qqq) Ethyl-carbamic acid 2-{1-[1-(4-{[2-(2-dimethylamino-3-methyl-butyrylamino)-3-methyl-butyryl]-methyl-amino}-3-methoxy-5-methyl-heptanoyl)-pyrrolidin-2-yl]-2-phenethylcarbamoyl-ethylsulfanyl}-ethyl ester.

42. A compound of the formula (I)

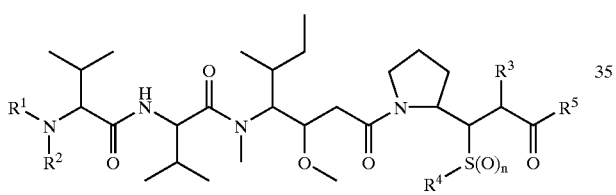

(I)

wherein

R$^1$ and R$^2$ are methyl;

R$^3$ is hydrogen;

R$^4$ is phenyl; methyl; t-butyl; 4-t-butylphenyl; 4-methoxyphenyl; 2-aminoethyl; 2-dimethylaminoethyl; ZHNCH$_2$CH$_2$— wherein Z is benzyloxycarbonyl; 4-methylthiophenyl; cyclohexyl; 2-, 3-, or 4-hydroxyphenyl; 4-acetoaminophenyl; 4-fluorophenyl; ethyl; i-propyl; benzyl; 2-acetoxyethyl; phenylethyl; allyl; n-pentyl; 2-naphthyl; 4-fluorobenzyl; 2-furylmethyl or 2-hydroxyethyl;

R$^5$ is phenylethylamino; phenylethoxy; benzyloxy; 2-naphthylmethylamino; benzylpiperazino; 1,2,3,4-tetrahydroisoquinolino; t-butoxy; hydroxy; 4-H$_2$NSO$_2$PhCH$_2$CH$_2$; 2-, 3- or 4-hydroxyphenylethylamino; N-benzylphenethylamino; 4-t-butylbenzylamino; benzylamino; N-methylphenethylamino; 2-, 3- or 4-hydroxyphenylethyl-N-methylamino; 4-benzhydrylpiperazino; 2-phenylcyclopropylamino; thienylethylamino; 2-pyridylethylamino; 5-ethylpyrazol; 4,3-dimethoxyphenylethylamino; benzyl-hydrazino; benzothiazol-2-ylmethyl-amino; 2-pyridin-4-yl-amino; 3,4-dimethoxy-phenyl-ethyl-methyl-amino; benzothiazol-2-ylmethyl-amimo; 2-pyridin-3-yl-ethylamino; pyridin-4-ylmethyl-amino; thiazol-2-ylamino; naphthalen-2-ylamino; 4-chloro-phenyl-ethylamino; 4-methoxy-phenyl-ethylamino; 4-(1,2,3)thiadiazol-4-yl-benzylamino; 2-cyclohexylamino or 1-benzyl-piperidin-4-ylamino; and n is 1;

or a pharmaceutically acceptable salt thereof.

43. The compound of claim 42 which is N-[1-({1-sec-Butyl-4-[2-(1-methanesulfinyl-2-phenethylcarbamoyl-ethyl)-pyrrolidin-1-yl]-2-methoxy-4-oxo-butyl}-methyl-carbamoyl)-2-methyl-propyl]-2-dimethylamino-3-methyl-butyramide.

44. The compound of claim 20, which is selected from the group consisting of a) N-[1-({1-sec-Butyl-2-methoxy-4-[2-(1-methylsulfanyl-2-phenethylcarbamoyl-propyl)-pyrrolidin-1-yl]-4-oxo-butyl}-methyl-carbamoyl)-2-methyl-propyl]-2-dimethylamino-3-methyl-butyramide, b) N-[1-({1-sec-Butyl-4-[2-(1-tert-butylsulfanyl-2-phenethylcarbamoyl-propyl)-pyrrolidin-1-yl]-2-methoxy-4-oxo-butyl}-methyl-carbamoyl)-2-methyl-propyl]-2-dimethylamino-3-methyl-butyramide, c) N-{1-[(1-sec-Butyl-4-{2-[1-(2-hydroxy-ethylsulfanyl)-2-phenethylcarbamoyl-propyl]-pyrrolidin-1-yl}-2-methoxy-4-oxo-butyl)-methyl-carbamoyl]-2-methyl-propyl}-2-dimethylamino-3-methyl-butyramide, d) N-{1-[(1-sec-Butyl-4-{2-[1-(4-hydroxy-phenylsulfanyl)-2-phenethylcarbamoyl-propyl]-pyrrolidin-1-yl}-2-methoxy-4-oxo-butyl)-methyl-carbamoyl]-2-methyl-propyl}-2-dimethylamino-3-methyl-butyramide, e) N-{1-[(1-sec-Butyl-4-{2-[1-(3-hydroxy-phenylsulfanyl)-2-phenethylcarbamoyl-propyl]-pyrrolidin-1-yl}-2-methoxy-4-oxo-butyl)-methyl-carbamoyl]-2-methyl-propyl}-2-dimethylamino-3-methyl-butyramide, f) N-{1-[(1-sec-Butyl-4-{2-[1-(2-hydroxy-phenylsulfanyl)-2-phenethylcarbamoyl-propyl]-pyrrolidin-1-yl}-2-methoxy-4-oxo-butyl)-methyl-carbamoyl]-2-methyl-propyl}-2-dimethylamino-3-methyl-butyramide, g) N-(1-{[1-sec-Butyl-4-(2-{2-[2-(4-hydroxy-phenyl)-ethylcarbamoyl]-1-t-butylsulfanyl-propyl}-pyrrolidin-1-yl)-2-methoxy-4-oxo-butyl]-methyl-carbamoyl}-2-methyl-propyl)-2-dimethylamino-3-methyl-butyramide, and h) N-(1-{[1-sec-Butyl-4-(2-{2-[2-(3-hydroxy-phenyl)-ethylcarbamoyl]-1-t-butylsulfanyl-propyl}-pyrrolidin-1-yl)-2-methoxy-4-oxo-butyl]-methyl-carbamoyl}-2-methyl-propyl)-2-dimethylamino-3-methyl-butyramide.

45. The compound of claim 20, which is selected from the group consisting of i) N-(1-{[1-sec-Butyl-4-(2-{2-[2-(2-hydroxy-phenyl)-ethylcarbamoyl]-1-t-butylsulfanyl-propyl}-pyrrolidin-1-yl)-2-methoxy-4-oxo-butyl]-methyl-carbamoyl}-2-methyl-propyl)-2-dimethylamino-3-methyl-butyramide, j) N-(1-{[1-sec-Butyl-4-(2-{2-[2-(4-hydroxy-phenyl)-ethylcarbamoyl]-1-methylsulfanyl-propyl}-pyrrolidin-1-yl)-2-methoxy-4-oxo-butyl]-methyl-carbamoyl}-2-methyl-propyl)-2-dimethylamino-3-methyl-butyramide, k) N-(1-{[1-sec-Butyl-4-(2-{2-[2-(3-hydroxy-phenyl)-ethylcarbamoyl]-1-methylsulfanyl-propyl}-pyrrolidin-1-yl)-2-methoxy-4-oxo-butyl]-methyl-carbamoyl}-2-methyl-propyl)-2-dimethylamino-3-methyl-butyramide, i) N-(1-{[1-sec-Butyl-4-(2-{2-[2-(2-hydroxy-phenyl)-ethylcarbamoyl]-1-methylsulfanyl-propyl}-pyrrolidin-1-yl)-2-methoxy-4-oxo-butyl]-methyl-carbamoyl}-2-methyl-propyl)-2-dimethylamino-3-methyl-butyramide, m) N-(1-{[1-sec-Butyl-4-(2-{2-[2-(3-hydroxy-phenyl)-ethylcarbamoyl]-1-pentylsulfanyl-propyl}-pyrrolidin-1-yl)-2-methoxy-4-oxo-butyl]-methyl-carbamoyl}-2-methyl-propyl)-2-dimethylamino-3-methyl-butyramide, n) N-[1-({1-sec-Butyl-4-[2-(2-{[2-(3-hydroxy-phenyl)-ethyl]-methyl-carbamoyl}-1-methylsulfanyl-propyl)-pyrrolidin-1-yl]-2-methoxy-4-oxo-butyl}-methyl-carbamoyl)-2-methyl-propyl]-2-dimethylamino-3-methyl-butyramide, o) N-[1-({1-sec-Butyl-4-[2-(1-ethylsulfanyl-2-{[2-(3-hydroxy-phenyl)-ethyl]-methyl-carbamoyl}-propyl)-pyrrolidin-1-yl]-2-methoxy-4-oxo-butyl}-methyl-carbamoyl)-2-methyl-propyl]-2-dimethylamino-3-methyl-butyramide, p) N-(1-{[1-sec-Butyl-4-(2-{1-ethylsulfanyl-2-[2-(3-hydroxy-phenyl)-ethylcarbamoyl]-propyl}-pyrrolidin-1-yl)-2-methoxy-4-oxo-butyl]-methyl-carbamoyl}-2-methyl-propyl)-2-dimethylamino-3-methyl-butyramide, and q) Ethyl-carbamic acid 3-(2-{3-[1-(4-{[2-(2-dimethylamino-3-methyl-butyrylamino)-3-methyl-butyryl]-methyl-amino}-3-methoxy-5-methyl-heptanoyl)-pyrrolidin-2-yl]-2-methyl-3-methylsulfanyl-propionylamino}-ethyl)-phenyl ester.

46. A compound of formula (I-I),

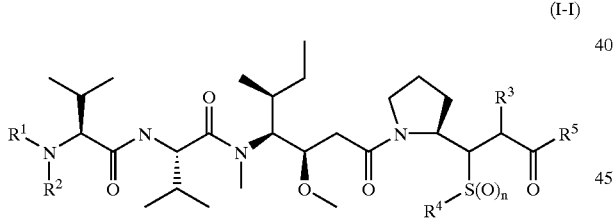

(I-I)

wherein $R^1$ and $R^2$ are methyl;

$R^3$ is hydrogen;

$R^4$ is selected from phenyl, methyl, t-butyl, 4-t-butylphenyl, 4-methoxyphenyl, 2-aminoethyl, 2-dimethylaminoethyl, ZHNCH$_2$CH$_2$— wherein Z is benzyloxycarbonyl, 4-methylthiophenyl, cyclohexyl, 2-, 3-, or 4-hydroxyphenyl, 4-acetoaminophenyl, 4-fluorophenyl, ethyl, i-propyl, benzyl, 2-acetoxyethyl, phenylethyl, allyl, n-pentyl, 2-naphthyl, 4-fluoro-benzyl, 2-furylmethyl or 2-hydroxyethyl;

$R^5$ is phenylethylamino, phenylethoxy, benzyloxy, 2-naphthylmethylamino, benzylpiperazino, 1,2,3,4-tetrahydroisoquinolino, t-butoxy, hydroxy, 4-H$_2$NSO$_2$PhCH$_2$CH$_2$, 2-, 3- or 4-hydroxyphenylethylamino, N-benzylphenethylamino, 4-t-butylbenzylamino, benzylamino, N-methylphenethylamino, 4-benzhydrylpiperazino, 2-phenylcyclopropylamino, thienylethylamino, 2-pyridylethylamino, 5-ethylpyrazol, 4,3-dimethoxyphenylethylamino, benzylhydrazino, benzothiazol-2-ylmethyl-amino, 2-pyridin-4-yl-amino, 3,4-dimethoxy-phenyl-ethyl-methyl-amino, benzothiazol-2-ylmethyl-amino, 2-pyridin-3-yl-ethylamino, pyridin-4-ylmethyl-amino, thiazol-2-ylamino, naphthalen-2-ylamino, 4-chloro-phenyl-ethylamino, 4-methoxy-phenyl-ethylamino, 4-(1,2,3)thiadiazol-4-yl-benzylamino, 2-cyclohexylamino or 1-benzyl-piperidin-4-ylamino; and n is 0;

or a pharmaceutically acceptable salt thereof.

47. A compound of formula (I-I),

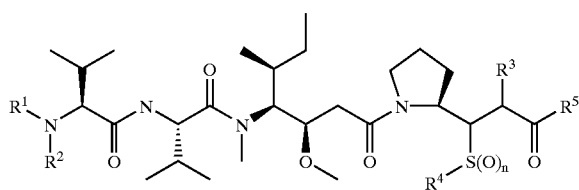

(I-I)

wherein $R^1$ and $R^2$ are methyl;

$R^3$ is hydrogen;

$R^4$ is selected from phenyl, methyl, t-butyl, 4-t-butylphenyl, 4-methoxyphenyl, 2-aminoethyl, 2-dimethylaminoethyl, ZHNCH$_2$CH$_2$— wherein Z is benzyloxycarbonyl, 4-methylthiophenyl, cyclohexyl, 2-, 3-, or 4-hydroxyphenyl, 4-acetoaminophenyl, 4-fluorophenyl, ethyl, i-propyl, benzyl, 2-acetoxyethyl, phenylethyl, allyl, n-pentyl, 2-naphthyl, 4-fluoro-benzyl, 2-furylmethyl or 2-hydroxyethyl;

$R^5$ is selected from phenylethylamino, phenylethoxy, benzyloxy, 2-naphthylmethylamino, benzylpiperazino, 1,2,3,4-tetrahydroisoquinolino, t-butoxy, hydroxy, 4-H$_2$NSO$_2$PhCH$_2$CH$_2$, 2-, 3- or 4-hydroxy-phenylethylamino, N-benzyl-phenethylamino, 4-t-butylbenzylamino, benzylamino, N-methylphenethylamino, 4-benzhydrylpiperazino, 2-phenylcyclopropylamino, thienylethylamino, 2-pyridylethylamino, 5-ethylpyrazol, 4,3-dimethoxyphenylethylamino, benzylhydrazino, benzothiazol-2-ylmethyl-amino, 2-pyridin-4-yl-amino, 3,4-dimethoxy-phenyl-ethyl-methyl-amino, benzothiazol-2-ylmethyl-amino, 2-pyridin-3-yl-ethylamino, pyridin-4-ylmethyl-amino, thiazol-2-ylamino, naphthalen-2-ylamino, 4-chloro-phenyl-ethylamino, 4-methoxy-phenyl-ethylamino, 4-(1,2,3)thiadiazol-4-yl-benzylamino, 2-cyclohexylamino or 1-benzyl-piperidin-4-ylamino; and n is 1;

or a pharmaceutically acceptable salt thereof.

48. The compound N-(1-{[1-sec-Butyl-4-(2-{2-[2-(3-hydroxy-phenyl)-ethylcarbamoyl]-1-methylsulfanyl-propyl}-pyrrolidin-1-yl)-2-methoxy-4-oxo-butyl]-methyl-carbamoyl}-2-methyl-propyl)-2-dimethylamino-3-methyl-butyramide.

49. The compound N-[1-({1-sec-Butyl-4-[2-(1-ethylsulfanyl-2-{[2-(3-hydroxy-phenyl)-ethyl]-methyl-carbamoyl}-propyl)-pyrrolidin-1-yl]-2-methoxy-4-oxo-butyl}-methyl-carbamoyl)-2-methyl-propyl]-2-dimethylamino-3-methyl-butyramide.

50. The compound N-(1-{[1-sec-Butyl-4-(2-{1-ethylsulfanyl-2-[2-(3-hydroxy-phenyl)-ethylcarbamoyl]- propyl}-pyrrolidin-1-yl)-2-methoxy-4-oxo-butyl]-methyl-carbamoyl}-2-methyl-propyl)-2-dimethylamino-3-methyl-butyramide.

51. A pharmaceutical composition comprising a pharmaceutically acceptable carrier and at least one compound selected from N-[1-({1-sec-Butyl-4-[2-(2-{[2-(3-hydroxy-phenyl)-ethyl]-methyl-carbamoyl}-1-methylsulfanyl-propyl)-pyrrolidin-1-yl]-2-methoxy-4-oxo-butyl}-methyl-carbamoyl)-2-methyl-propyl]-2-dimethylamino-3-methyl-butyramide, N-(1-{[1-sec-Butyl-4-(2-{2-[2-(3-hydroxy-phenyl)-ethylcarbamoyl]-1-methylsulfanyl-propyl}-pyrrolidin-1-yl)-2-methoxy-4-oxo-butyl]-methyl-carbamoyl}-2-methyl-propyl)-2-dimethylamino-3-methyl-butyramide, N-[1-({1-sec-Butyl-4-[2-(1-ethylsulfanyl-2-{[2-(3-hydroxy-phenyl)-ethyl]-methyl-carbamoyl}-propyl)-pyrrolidin-1-yl]-2-methoxy-4-oxo-butyl}-methyl-carbamoyl)-2-methyl-propyl]-2-dimethylamino-3-methyl-butyramide, or N-(1-{[1-sec-Butyl-4-(2-{1-ethylsulfanyl-2-[2-(3-hydroxy-phenyl)-ethylcarbamoyl]-propyl}-pyrrolidin-1-yl)-2-methoxy-4-oxo-butyl]-methyl-carbamoyl}-2-methyl-propyl)-2-dimethylamino-3-methyl-butyramide.

52. A method of treating colorectal, lung or breast cancer comprising administering to a patient in need of such treatment a therapeutically effective amount of a least one compound selected from N-[1-({1-sec-Butyl-4-[2-(2-{[2-(3-hydroxy-phenyl)-ethyl]-methyl-carbamoyl}-1-methylsulfanyl-propyl)-pyrrolidin-1-yl]-2-methoxy-4-oxo-butyl}-methyl-carbamoyl)-2-methyl-propyl]-2-dimethylamino-3-methyl-butyramide, N-(1-{[1-sec-Butyl-4-(2-{2-[2-(3-hydroxy-phenyl)-ethylcarbamoyl]-1-methylsulfanyl-propyl}-pyrrolidin-1-yl)-2-methoxy-4-oxo-butyl]-methyl-carbamoyl}-2-methyl-propyl)-2-dimethylamino-3-methyl-butyramide, N-[1-({1-sec-Butyl-4-[2-(1-ethylsulfanyl-2-{[2-(3-hydroxy-phenyl)-ethyl]-methyl-carbamoyl}-propyl)-pyrrolidin-1-yl]-2-methoxy-4-oxo-butyl}-methyl-carbamoyl)-2-methyl-propyl]-2-dimethylamino-3-methyl-butyramide, or N-(1-{[1-sec-Butyl-4-(2-{1-ethylsulfanyl-2-[2-(3-hydroxy-phenyl)-ethylcarbamoyl]-propyl}-pyrrolidin-1-yl)-2-methoxy-4-oxo-butyl]-methyl-carbamoyl}-2-methyl-propyl)-2-dimethylamino-3-methyl-butyramide.

* * * * *

UNITED STATES PATENT AND TRADEMARK OFFICE
CERTIFICATE OF CORRECTION

PATENT NO.      : 6,737,409 B2
DATED           : May 18, 2004
INVENTOR(S)     : Toshihiko Fujii et al.

It is certified that error appears in the above-identified patent and that said Letters Patent is hereby corrected as shown below:

<u>Title page,</u>
Item [75], Inventors, should read:
-- Toshihiko Fujii, Yokohama-shi (JP); Takehiro Okada, Fujisawa-shi (JP); Mikio Taniguchi, Fujisawa-shi (JP); Fumio Watanabe, Kamakura-shi (JP). --

<u>Column 54,</u>
Line 35, "heterocycloalkyamino" should read -- heterocycloalkylamino --.

<u>Column 58,</u>
Line 23, "benzylhydrazino" should read -- benzhydrazino --

Signed and Sealed this

Twenty-third Day of November, 2004

JON W. DUDAS
*Director of the United States Patent and Trademark Office*